United States Patent
Aoki et al.

(10) Patent No.: US 8,632,459 B2
(45) Date of Patent: Jan. 21, 2014

(54) INTRA-SUBJECT OBSERVATION SYSTEM AND INTRA-SUBJECT OBSERVATION METHOD

(75) Inventors: Isao Aoki, Sagamihara (JP); Katsumi Hirakawa, Sagamihara (JP); Hironobu Takizawa, Hachioji (JP); Hidetake Segawa, Hachioji (JP); Hironao Kawano, Hino (JP); Hideo Ito, Akishima (JP); Hideki Shimonaka, Hachioji (JP)

(73) Assignee: Olympus Medical Sytems Corp., Tokyo (JP)

( * ) Notice: Subject to any disclaimer, the term of this patent is extended or adjusted under 35 U.S.C. 154(b) by 1336 days.

(21) Appl. No.: 12/146,905

(22) Filed: Jun. 26, 2008

(65) Prior Publication Data
US 2008/0300453 A1 Dec. 4, 2008

Related U.S. Application Data

(63) Continuation of application No. PCT/JP2006/325639, filed on Dec. 22, 2006.

(30) Foreign Application Priority Data

| Dec. 28, 2005 | (JP) | 2005-380452 |
| Dec. 28, 2005 | (JP) | 2005-380453 |
| Dec. 28, 2005 | (JP) | 2005-380455 |

(51) Int. Cl.
*A61B 1/00* (2006.01)
*A61B 1/04* (2006.01)

(52) U.S. Cl.
USPC .................................... 600/117

(58) Field of Classification Search
USPC ................................. 600/109, 160, 178, 180
See application file for complete search history.

(56) References Cited

U.S. PATENT DOCUMENTS

| 2003/0018280 | A1  | 1/2003 | Lewkowicz et al. | |
| 2006/0155174 | A1* | 7/2006 | Glukhovsky et al. | 600/301 |
| 2007/0129624 | A1* | 6/2007 | Gilad et al. | 600/407 |
| 2008/0199065 | A1* | 8/2008 | Swain | 382/133 |
| 2010/0010300 | A1* | 1/2010 | Gilad | 600/109 |
| 2011/0034795 | A9* | 2/2011 | Gilad et al. | 600/407 |
| 2011/0060189 | A1* | 3/2011 | Belson | 600/117 |

FOREIGN PATENT DOCUMENTS

| JP | 2003-210395 A | 7/2003 |
| JP | 2003-325438 A | 11/2003 |
| JP | 2005198879 A | 7/2005 |
| WO | WO 02/095351 A3 | 11/2002 |

(Continued)

OTHER PUBLICATIONS

Japanese Office Action dated Jun. 7, 2011 together with English translation.

(Continued)

*Primary Examiner* — Philip R Smith
(74) *Attorney, Agent, or Firm* — Scully, Scott, Murphy & Presser, P.C.

(57) ABSTRACT

An intra-subject observation system includes a first liquid inserted into a desired organ of a subject; and a second liquid inserted into the organ without being mixed with the first liquid due to a specific gravity lighter than that of the first liquid. The system also includes a capsule medical apparatus inserted into the organ with an intermediate specific gravity between the specific gravity of the first liquid and that of the second liquid to acquire intra-subject information, which is output out of the subject by radio.

40 Claims, 51 Drawing Sheets

(56) References Cited

FOREIGN PATENT DOCUMENTS

| | | |
|---|---|---|
| WO | WO 2005/032370 A1 | 4/2005 |
| WO | WO 2005/060348 A2 | 7/2005 |
| WO | WO 2005/062717 A2 | 7/2005 |

OTHER PUBLICATIONS

Extended Supplementary European Search Report dated Oct. 19, 2010.

* cited by examiner

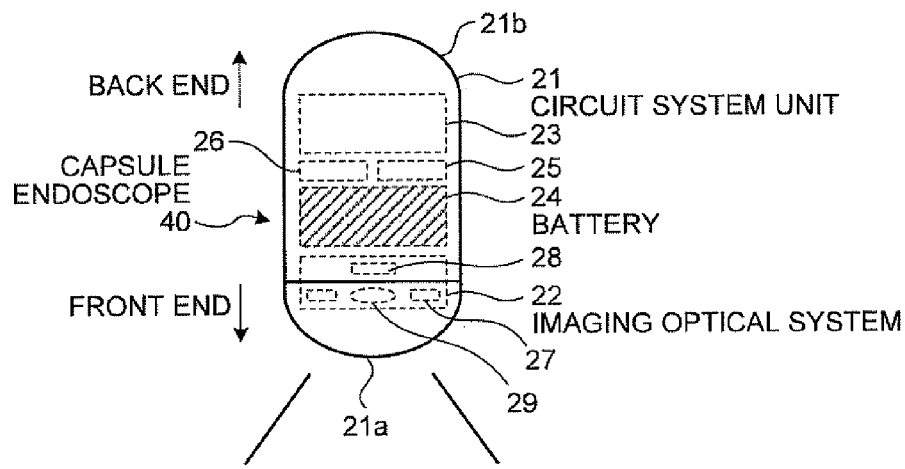
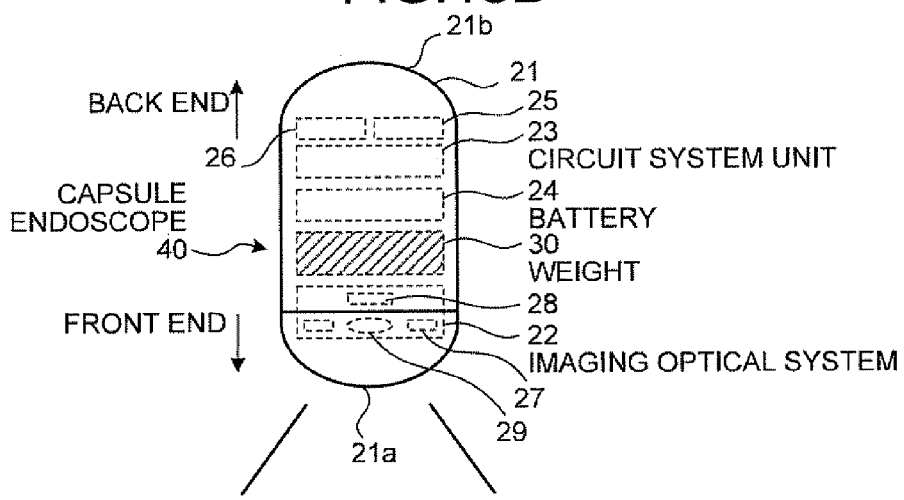
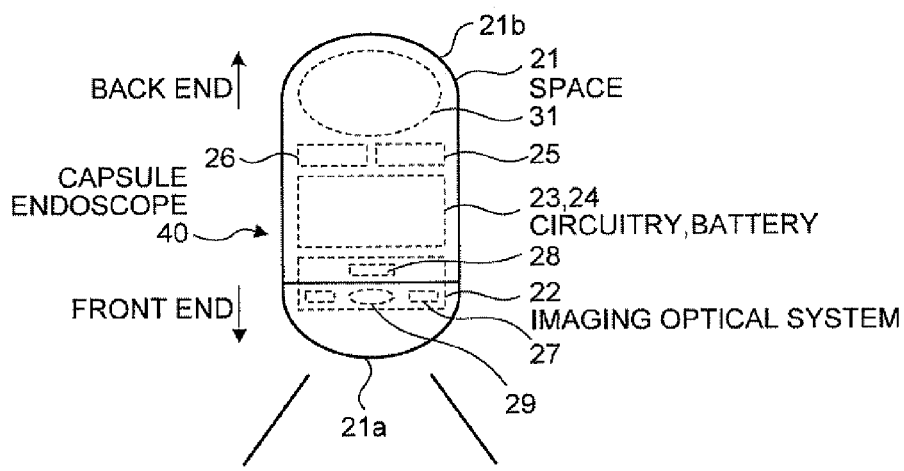

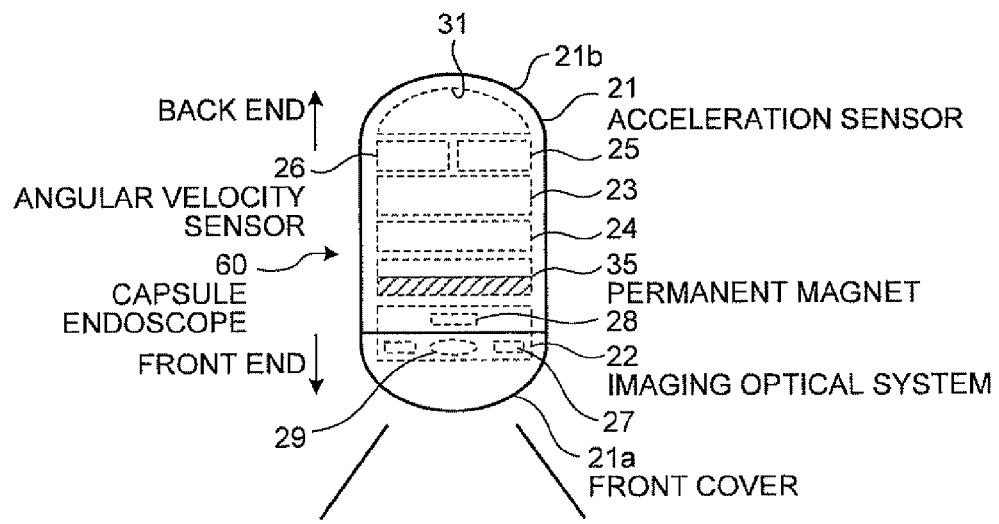
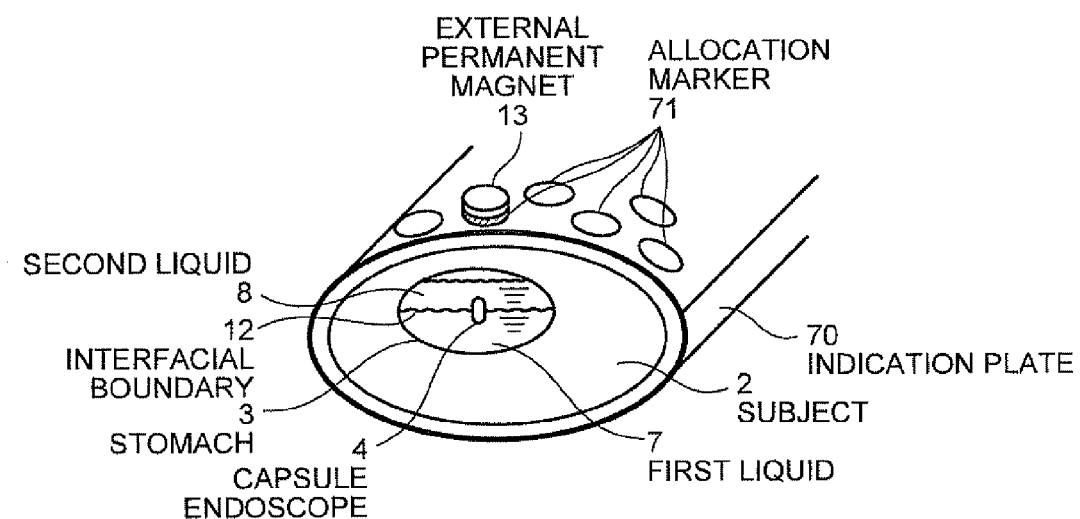

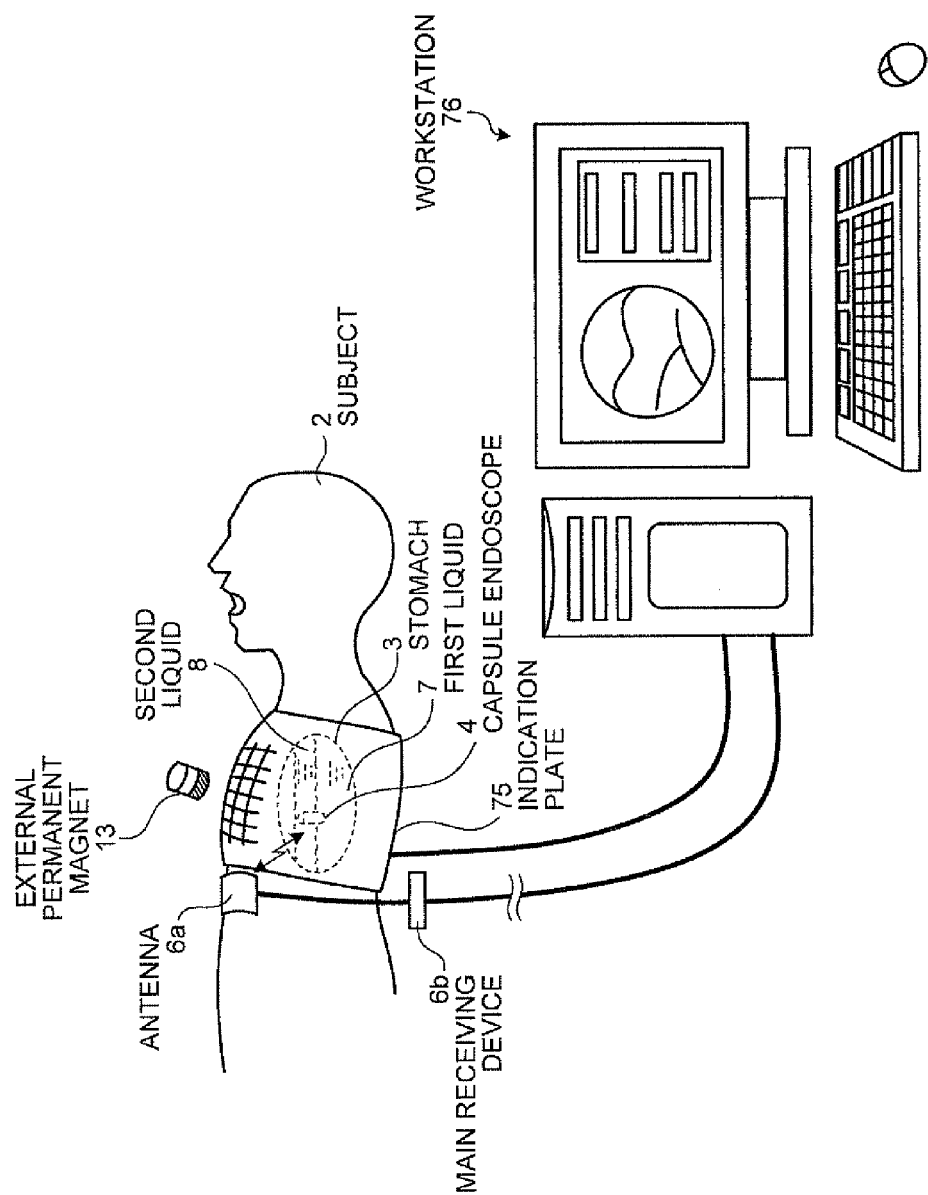

INTRA-SUBJECT OBSERVATION SYSTEM AND INTRA-SUBJECT OBSERVATION METHOD

CROSS-REFERENCE TO RELATED APPLICATIONS

This application is a continuation of PCT international application Ser. No. PCT/JP2006/325639 filed Dec. 22, 2006 which designates the United States, incorporated herein by reference, and which claims the benefit of priority from Japanese Patent Application Nos. 2005-380452, 2005-380453, and 2005-380455, all filed Dec. 28, 2005, incorporated herein by reference.

BACKGROUND OF THE INVENTION

1. Field of the Invention

The present invention relates to an intra-subject observation system and an intra-subject observation method for making an intra-subject observation by having a capsule medical apparatus inserted into a subject.

2. Description of the Related Art

Recent years saw the advent of a capsule endoscope equipped with an imaging function and a radio communication function in the field of endoscope. The capsule endoscope is constructed to successively pick up images using the imaging function while moving through organs (inside body cavity) such as the esophagus, stomach, and small intestine accompanying peristaltic movement in an observation period after being swallowed through the mouth of a subject, which is a body (human body), for observation (examination) until the capsule endoscope is naturally discharged from the subject.

Here, International Publication No. WO02/95351 discloses a technology appropriate for observation of the large intestine by setting the specific gravity of a capsule endoscope to that of a liquid around the capsule endoscope or to about 1, which is equal to that of water, so that the capsule endoscope floating in the liquid can move quickly through body cavity after being swallowed together with the liquid to reach the large intestine. Moreover, while a capsule endoscope can observe only portions nearby when stuck to the surface of a body cavity wall, according to Patent Document 1, the field of view for observation is secured so that observations can be made exhaustively by floating a capsule endoscope in a liquid for observation.

SUMMARY OF THE INVENTION

An intra-subject observation system according to an aspect of the present invention includes a first liquid inserted into a desired organ of a subject; a second liquid inserted into the organ without being mixed with the first liquid due to a specific gravity lighter than that of the first liquid; and a capsule medical apparatus inserted into the organ with an intermediate specific gravity between the specific gravity of the first liquid and that of the second liquid to acquire intra-subject information, which is output out of the subject by radio.

An intra-subject observation method according to another aspect of the present invention includes inserting a first liquid into a desired organ of a subject; inserting a second liquid, which does not mix with the first liquid due to a specific gravity lighter than that of the first liquid, into the organ; inserting a capsule medical apparatus, which has an intermediate specific gravity between the specific gravity of the first liquid and that of the second liquid, into the organ; and acquiring intra-subject information by the capsule medical apparatus inserted into the organ and floating at an interfacial boundary between the first liquid and the second liquid to output the intra-subject information out of the subject by radio.

An intra-subject observation system according to still another aspect of the present invention includes a first liquid inserted into a desired organ of a subject; a second liquid inserted into the organ without being mixed with the first liquid due to a specific gravity lighter than that of the first liquid; a capsule medical apparatus inserted into the organ with an intermediate specific gravity between the specific gravity of the first liquid and that of the second liquid and floating at an interfacial boundary between the first liquid and the second liquid in the organ to acquire intra-subject information, which is output out of the subject by radio; a receiving apparatus arranged outside the subject to receive the intra-subject information transmitted from the capsule medical apparatus inside the subject by radio; and a capsule displacement driving device for changing a floating position and/or floating posture of the capsule medical apparatus at the interfacial boundary.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13A is a side view showing the outline configuration of a third modification of the capsule endoscope whose front-end side is relatively heavier;

FIG. 13B is a side view showing the outline configuration of another third modification of the capsule endoscope whose front-end side is relatively heavier;

FIG. 13C is a side view showing the outline configuration of still another third modification of the capsule endoscope whose front-end side is relatively heavier;

FIG. 20 is a side view showing the outline configuration of a monocular capsule endoscope in a fourth modification with a weight balance in which the front-end side is relatively heavier;

FIG. 21 is a perspective view schematically exemplifying usage of an indication plate in a fifth modification;

FIG. 23 is a schematic diagram showing the overall configuration of an intra-subject observation system in a sixth modification having a magnified observation function for real-time observation;

DETAILED DESCRIPTION OF THE PREFERRED EMBODIMENTS

Embodiments of an intra-subject observation system and an intra-subject observation method according to the present invention will be described in detail below based on drawings. However, the present invention is not limited to embodiments shown below and can variously be modified within the scope of the present invention.

First Embodiment

Figure 1:
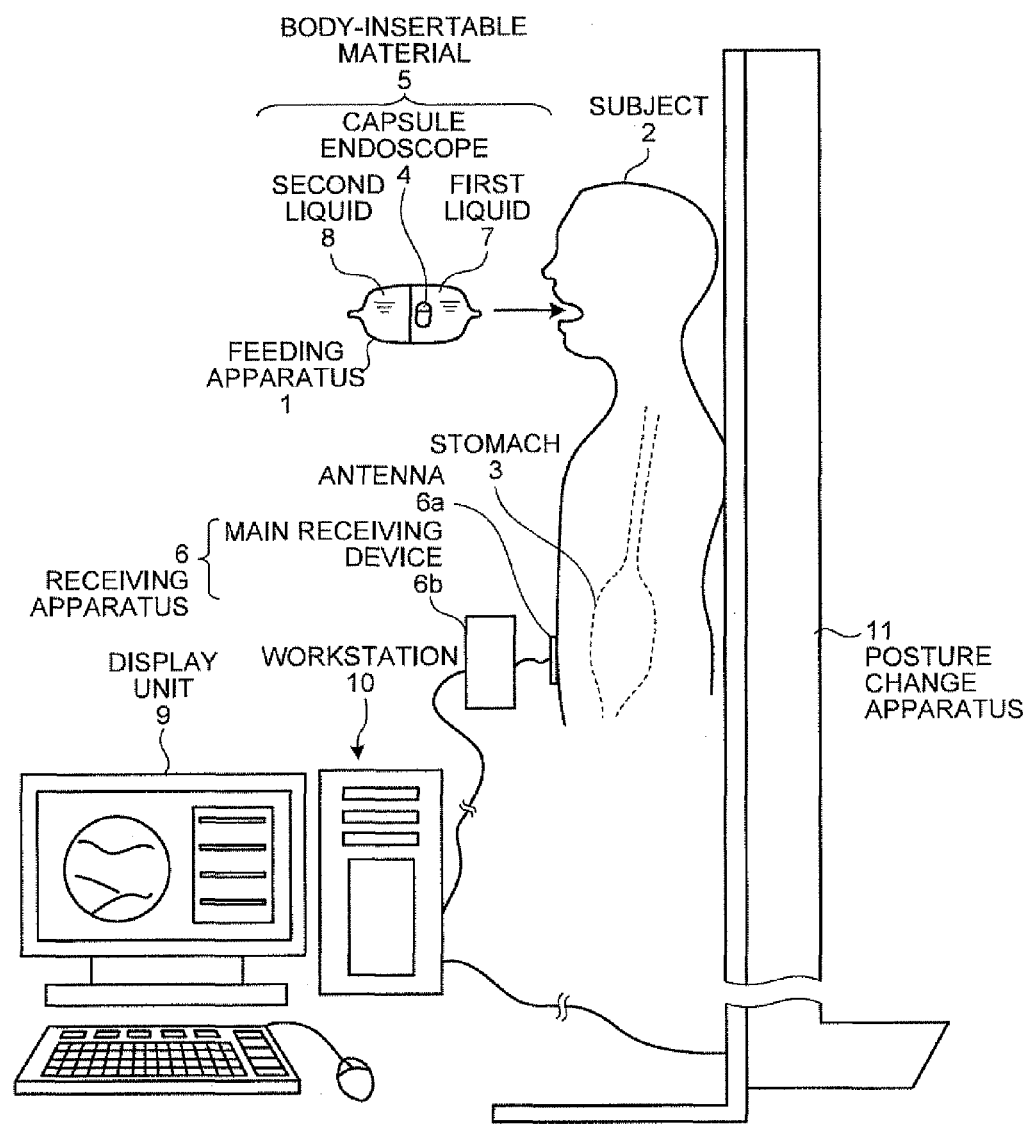
FIG. 1 is a schematic diagram showing an overall configuration of a radio intra-subject observation system in a preferred first embodiment of an intra-subject observation system according to the present invention.

FIG. 1 is a schematic diagram showing an overall configuration of a radio intra-subject observation system in a preferred first embodiment of the intra-subject observation system according to the present invention. The intra-subject observation system uses a capsule endoscope as an example of a capsule medical apparatus. In FIG. 1, the intra-subject observation system comprises a body-inserted material 5 including a capsule endoscope 4 for pickling up images inside a body cavity to transmit data such as a video signal and the like after being inserted into a desired organ such as a stomach 3 of a subject 2 by a feeding apparatus 1, which is a liquid insertion apparatus, and a receiving apparatus 6 used for reception processing of a radio signal transmitted from the capsule endoscope 4 inserted into the stomach 3. The receiving apparatus 6 is used while disposed near the subject 2 to perform reception processing of a radio signal received from the capsule endoscope 4. The body-inserted material 5 consists of the capsule endoscope 4, a first liquid 7, and a second liquid 8 prepared inside the feeding apparatus 1.

The intra-subject observation system in the first embodiment also comprises a display unit 9 for displaying images inside the body cavity based on a video signal received by the receiving apparatus 6 and a workstation 10 controlling the whole system. The receiving apparatus 6 comprises one or a plurality of antennas 6a attached to the body surface outside the subject 2 and near the stomach 3 and a main receiving unit 6b connected to the antenna 6a to perform reception processing of a radio signal received via the antenna 6a. The antenna 6a may also be fixed, for example, to a receiving jacket wearable by the subject 2 so that the subject 2 mounts the antenna 6a by wearing the receiving jacket. In this case, the antenna 6a may be freely removable from the jacket.

The workstation 10 is connected to the receiving apparatus 6 via a wire and configured so that data can be passed to the receiving apparatus 6. The display unit 9 is used to display images inside the body cavity or the like picked up by the capsule endoscope 4 and more specifically, may has a configuration to directly display an image such as a CRT display and a liquid crystal display or that to output an image to another medium such as a printer. For passing of data between the receiving apparatus 6 and the workstation 10, a built-in recorder such as a hard disk in the receiving apparatus 6 may be used to connect the receiving apparatus 6 and the workstation 10 by radio. Further, the workstation 10 itself may be configured to be used as a receiving apparatus by providing only the antenna 6a on the subject 2 side and making a signal received by the antenna 6a directly receivable by the workstation 10 through communication.

The intra-subject observation system in the first embodiment also comprises a posture change apparatus 11 for changing the posture of the subject 2 to be observed. The posture change apparatus 11 is used, based on a bed structure, to appropriately change the posture of the subject 2 to a standing position, a face-up position, or a lateral position by freely undergoing rotational displacement three-dimensionally caused by a motor-driven mechanism (not shown).

Figure 2:
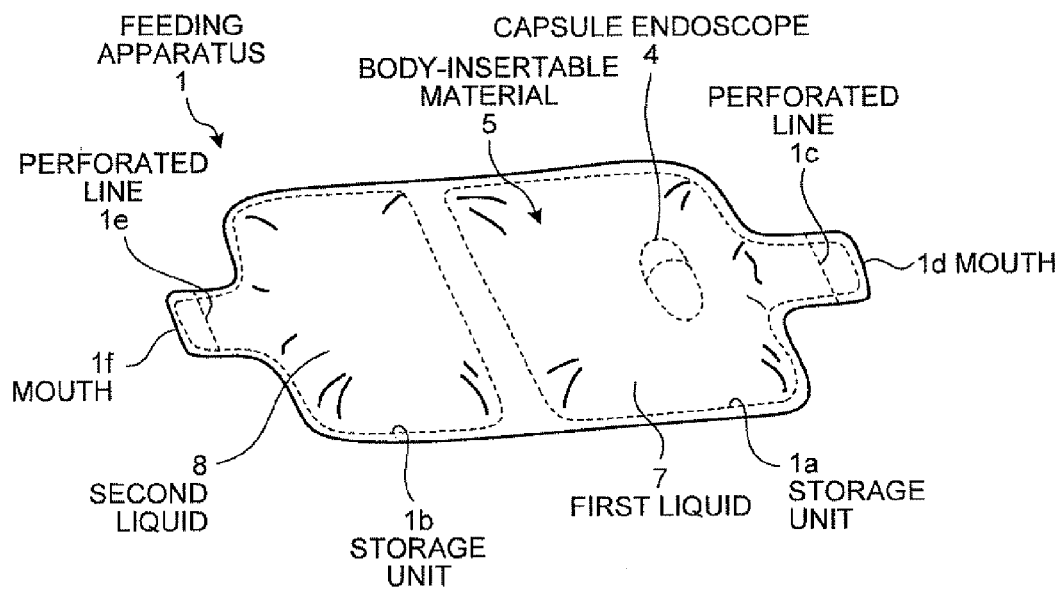
FIG. 2 is a schematic perspective view showing a feeding apparatus including body-inserted materials.

Here, the body-inserted material 5 will be described with reference to FIG. 2. FIG. 2 is a schematic perspective view showing the feeding apparatus 1 including the body-inserted material 5. The feeding apparatus 1 in the first embodiment is formed of a resin package structure having two storage units 1a and 1b separated by a partition wall and integrally storing the body-inserted material 5. The storage unit 1a stores the first liquid 7 and the capsule endoscope 4 together and is configured in such a way that the first liquid 7 and the capsule endoscope 4 are orally insertable into the stomach 3 of the subject 2 from a mouth 1d at one end opened by cutting along a perforated line 1c. The storage unit 1b stores the second liquid 8 and is configured in such a way that the second liquid 8 is orally insertable into the stomach 3 of the subject 2 from a mouth 1f at the other end opened by cutting along a perforated line 1e. Volumes of the storage units 1a and 1b are suitably set in accordance with the liquid insertion amount to be inserted into the stomach 3 and are set, for example, to about several hundred ml.

The capsule endoscope 4, the first liquid 7, and the second liquid 8 constituting the body-inserted material 5 by being stored in the feeding apparatus 1 each have a specific gravity of 1 or so, but have mutually different specific gravities and specific gravities are set so that (the first liquid 7)>(the capsule endoscope 4)>(the second liquid 8) are satisfied. The first liquid 7 and the second liquid 8 are both drinkable from an oral cavity of the subject 2, and liquids that do not mix together and are transparent to a wavelength of the imaging optical system of the capsule endoscope 4 are used. In the first embodiment, for example, the first liquid 7 is drinking water whose specific gravity is close to 1 and the second liquid 8 is edible oil such as olive oil whose specific gravity is less than 1. Further in the first embodiment, the first liquid 7 and the second liquid 8 are intended to be caused to remain in the stomach 3 in a period of observation and therefore, the temperature thereof is preferably 20° C. or higher when drunk. This is because drinking water and sport drinks are said to be absorbed fastest by the stomach when the temperature thereof is 5 to 15° C. and thus, if the temperature is somewhat higher, for example, 20° C. or higher, absorption is delayed to ensure a time in which liquids remain in the stomach 3.

Figure 3:
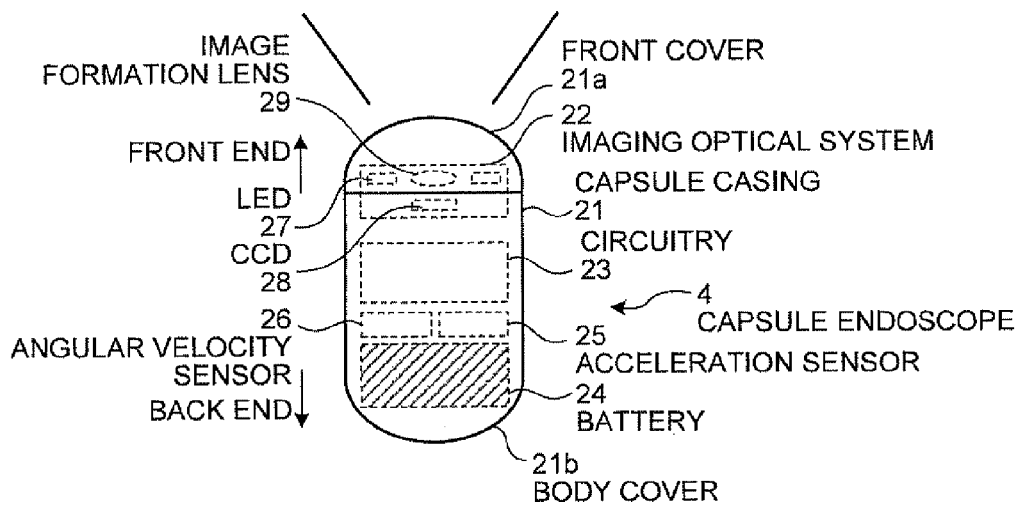
FIG. 3 is a side view showing an outline configuration of a capsule endoscope.

The capsule endoscope 4 will be described with reference to FIG. 3. FIG. 3 is a side view showing an outline configuration of the capsule endoscope 4. The capsule endoscope 4 in the first embodiment is, as shown in FIG. 3, a monocular capsule endoscope having a capsule casing 21 insertable into the body cavity of the subject 2 and an imaging optical system 22 contained in the capsule casing 21 and capable of imaging in a front-end direction. The capsule endoscope 4 also comprises a circuitry 23 including a board, circuit components, and a transmitting antenna and a battery 24, and also an acceleration sensor 25 and an angular velocity sensor (gyro) 26.

The capsule casing 21 has a size that can be swallowed into the body from the oral cavity of the subject 2 and an exterior case thereof fluid-tightly sealing the inside is formed by elastically fitting a front cover 21a in an approximately hemispherical shape having transparency or translucency and a body cover 21b in a closed-end cylindrical shape made of colored material to which visible light is opaque.

The imaging optical system 22 is inside the capsule casing 21 and comprises, for example, a plurality of light-emitting devices 27 (hereinafter, referred to the "LED 27") such as LEDs emitting illumination light for illuminating an imaging region inside the body cavity via the front cover 21a portion, an imaging device 28 (hereinafter, referred to representatively as the "CCD 28") such as a CCD and CMOS imaging an imaging region inside the body cavity by receiving a reflected light from an illumination light, and an image formation lens 29 forming an image of an object on the CCD 28, and is capable of imaging in the front-end direction on the front cover 21a side.

The battery 24 is a heavy component among components contained in the capsule endoscope 4 and is disposed on the back-end side inside the capsule casing 21. Accordingly, the center of gravity of the capsule endoscope 4 in the first embodiment is decentered toward the back-end side from the center by changing the weight balance in a front-back direction so that the front-end side becomes relatively lighter.

The acceleration sensor 25 is used to detect an acceleration of the capsule endoscope 4 inside the capsule casing 21 and also to detect a movement magnitude of the capsule endoscope 4 by integrating detection results. In the present embodiment, detection of acceleration in three axes (a longitudinal direction Z and diameter directions X and Y of the capsule endoscope 4) is enabled. The angular velocity sensor (gyro) 26 is used to detect an angle of oscillation of the capsule endoscope 4 inside the capsule casing 21. A detection signal from the angular velocity sensor 26 serves to detect the direction (posture) in which the capsule endoscope 4 is currently oriented. With the acceleration sensor 25 and the angular velocity sensor 26 provided, the position and orientation (including an up-and-down direction of the CCD 29) of the capsule endoscope 4 can be detected. The acceleration sensor 25 and the angular velocity sensor 26 are each constructed as a micro-sensor using a HEMS (Micro Electro Mechanical Systems) technology and, as described later, implement a detector for detecting a floating position and a floating posture of the capsule endoscope 4 floating at an interfacial boundary 12 between the first liquid 7 and the second liquid 8. If detection of the floating position of the capsule endoscope 4 is sufficient, only the acceleration sensor 25 needs to be provided and, if detection of the floating posture is sufficient, only the angular velocity sensor 26 needs to be provided. As a means for detecting the position or posture, a system in which a magnetic field or radio wave emitted by a capsule is received by an apparatus outside the body may also be adopted.

Figure 4:
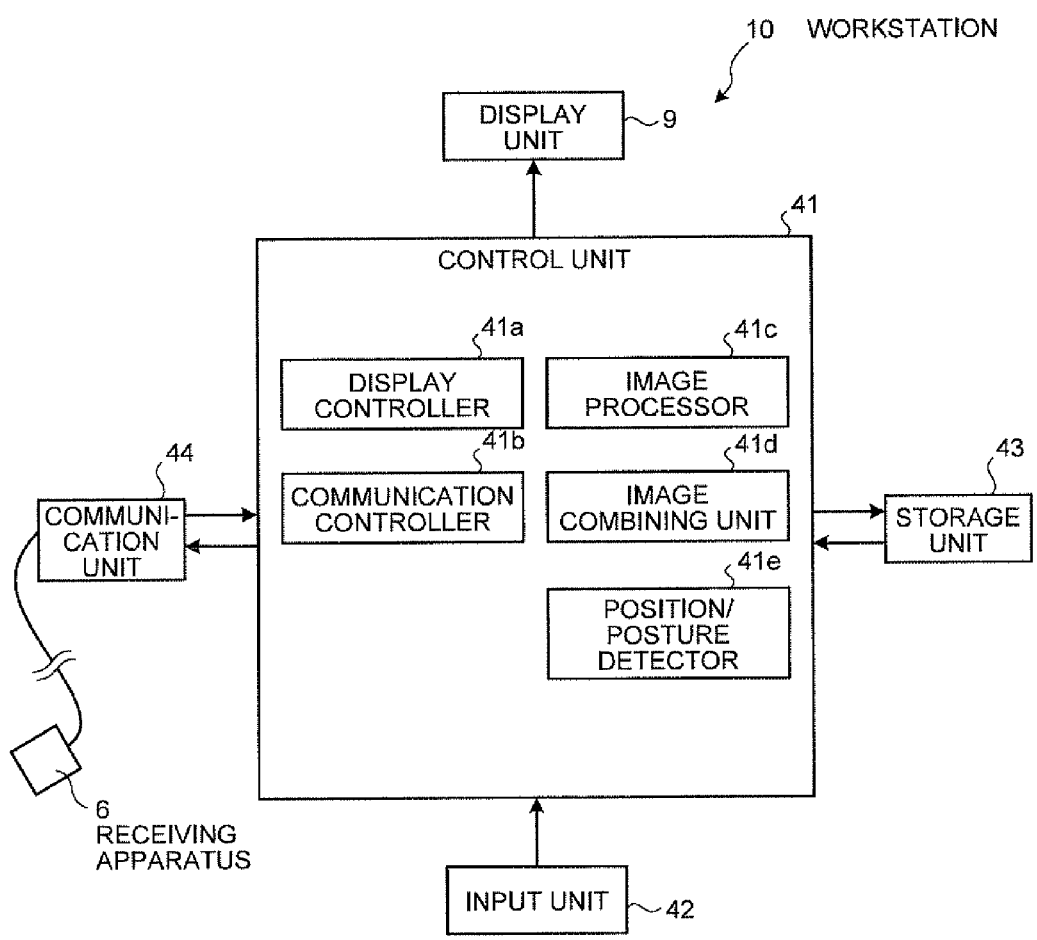
FIG. 4 is a schematic block diagram exemplifying the configuration of a workstation.

Here, an example of the configuration of the above workstation 10 will be described with reference to FIG. 4. FIG. 4 is a schematic block diagram exemplifying the configuration of the workstation 10. The workstation 10 in the first embodiment comprises a control unit 41, an input unit 42 connected to the control unit 41, the display unit 9, a storage unit 43, and a communication unit 44. The input unit 42 is comprised of a keyboard, a mouse, or the like and is used to automatically input information necessary for the control unit 41 or to input information based on manual operations. The storage unit 43 is used to store various kinds of information acquired from the capsule endoscope 4 and other information and is formed of a hard disk device or the like. The communication unit 44 is in charge of transmitting and receiving information between the receiving apparatus 6 and the workstation 10.

The control unit 41 is constructed of a computer configuration such as a CPU, ROM, and RAM and comprises execution units of various functions such as a display controller 41a, a communication controller 41b, an image processor 41c, an image combining unit 41d, a position/posture detector 41e, and a state determining unit 41f. The display controller 41a is used to perform display control of images inside the body cavity acquired from the capsule endoscope 4 via the receiving apparatus 6 to the display unit 9. The communication controller 41b is used to control transmission/reception operations performed by the communication unit 44 between the receiving apparatus 6 and the workstation 10. The image processor 41c is used to perform various kinds of image processing necessary for image data inside the body cavity acquired from the capsule endoscope 4 via the receiving apparatus 6. The position/posture detector 41e is used to detect the floating position or floating posture of the capsule endoscope 4 based on information of the position or orientation thereof detected by the acceleration sensor 25 or the angular velocity sensor 26. The image combining unit 41d is used to perform combination processing to link and combine a plurality of images from a plurality of pieces of image data inside the stomach 3 picked up by the capsule endoscope 4 by extracting common portions in image data with reference to information of the floating position and floating posture of the capsule endoscope 4 detected by the position/posture detector 41e.

Figure 5:
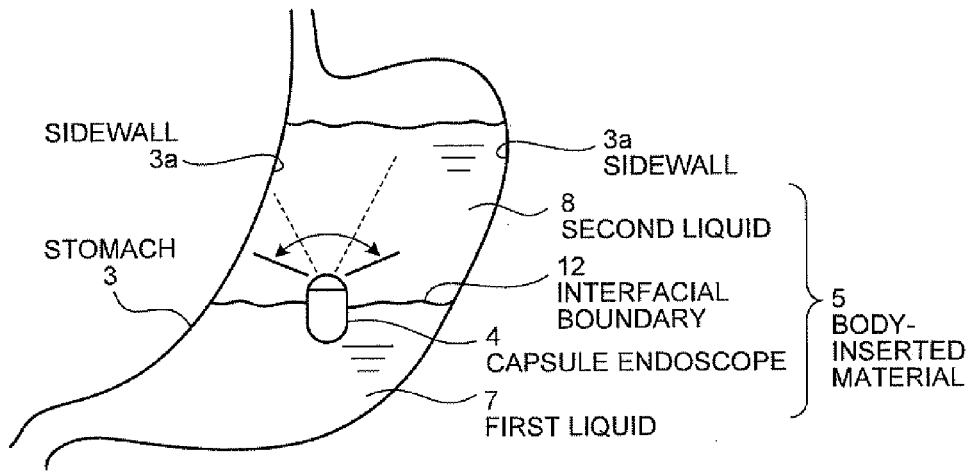
FIG. 5 is a schematic front view showing an appearance inside the stomach during observation.

Next, an observation method of the stomach 3 in the first embodiment will be described with reference to FIG. 5 to FIG. 8. FIG. 5 is a schematic front view showing an appearance inside the stomach 3 during observation. Before the observation, the capsule endoscope 4 is orally inserted into the stomach 3 together with the first liquid 7 and the second liquid 8 from the feeding apparatus 1. When the capsule endoscope 4, the first liquid 7, and the second liquid 8 constituting the body-inserted material 5 are inserted into the stomach 3, as shown in FIG. 5, a laminated state in which the second liquid 8 forms the interfacial boundary 12 above the first liquid 7 is brought about due to differences in specific gravity, with the capsule endoscope 4 having an intermediate specific gravity positioned at the interfacial boundary 12 to float there.

Here, as described with reference to FIG. 3, the center of gravity of the capsule endoscope 4 is decentered toward the back-end side and therefore, the capsule endoscope 4 floats in a standing state (vertical state) with the front-end side to be the imaging direction directed upward at the interfacial boundary 12. While the standing state can be secured to some degree with the first liquid 7 only, in the first embodiment, the interfacial boundary 12 is formed by liquids and viscosity becomes stronger in the presence of the second liquid 8 with a smaller difference in specific gravity compared with a case of air above the interfacial boundary 12 and therefore, the capsule endoscope 4 floats with stability at the interfacial boundary 12 in a standing state in accordance with the arrangement of the center of gravity because the capsule endoscope 4 moves (falls) only slowly even if the interfacial boundary 12 fluctuates. In an upward stable state described above, inner wall images can be obtained by imaging the upper side inside the stomach 3 by the capsule endoscope 4 before being transmitted to the receiving apparatus 6.

If the second liquid 8 is not inserted and thus air space remains when imaging the inner wall of the stomach 3, a sidewall 3a region of the stomach 3 above the interfacial boundary 12 shrinks and extension/dilatation will be insufficient. In the first embodiment, however, the sidewall 3a region of the stomach 3 above the interfacial boundary 12 can also be sufficiently extended/dilated by causing the second liquid 8 to be inserted into the stomach 3 in addition to the first liquid 7 and therefore, satisfactory observations can be made by securing a sufficient field of view inside the stomach 3, which is a wide organ. The imaging direction of the capsule endoscope 4 is directed upward and, instead of the air space, the second liquid 8 fills a space around the front cover 21a and therefore, satisfactory images can be obtained even if the surface of the front cover 21a is scratched or dirty because such a scratch or dirt becomes inconspicuous.

At this point, the imaging region by the capsule endoscope 4 can be changed only by changing the position of the interfacial boundary 12 inside the stomach 3 in combination with a slight posture change of the subject 2 itself so that observations of the stomach 3 can be made exhaustively without omission. By using the capsule endoscope 4 provided with the imaging optical system 22 having a wider angle shown by solid lines instead of dotted lines shown in FIG. 5, observations inside the stomach 3 in a wider range can be made with a smaller posture change.

Figure 6:
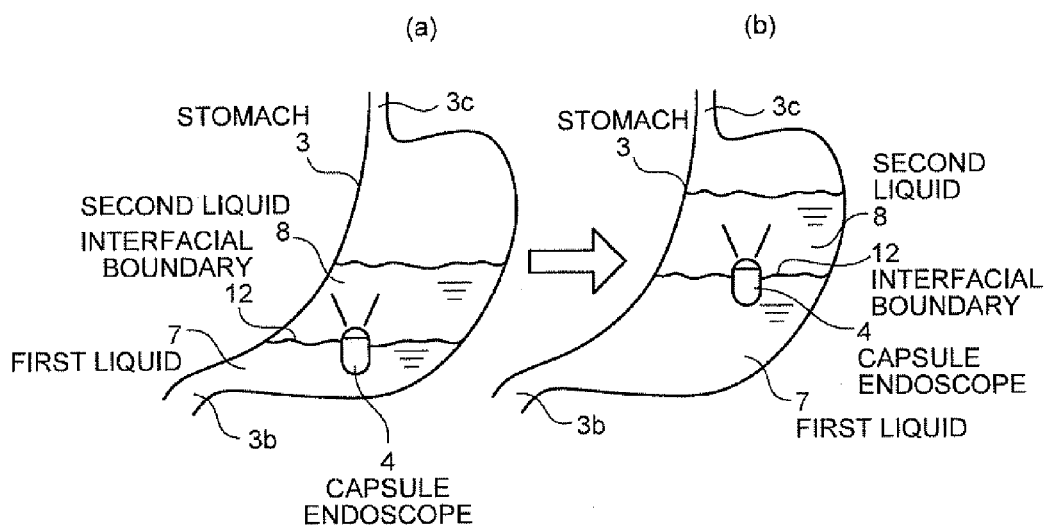
FIG. 6 is a schematic front view showing the appearance inside the stomach before and after increasing an insertion amount of a first liquid.

In the first embodiment, observations inside the stomach 3 can be caused to be made with the floating position in a gravity direction of the capsule endoscope 4 inside the stomach 3 set at an arbitrary position by causing the height position of the interfacial boundary 12 to change by changing insertion amounts of the first liquid 7 and the second liquid 8 into the stomach 3. FIG. 6 is a schematic front view showing the appearance inside the stomach 3 before and after increasing the insertion amount of the first liquid 7. That is, as shown in FIG. 6(a), after starting an observation by swallowing the capsule endoscope 4 together with predetermined amounts of the first liquid 7 and the second liquid 8, as shown in FIG. 6(b), the inner wall can be observed successively from a lower part (pyloric part of stomach) 3b toward an upper part (cardiac part of stomach) 3c of the stomach 3 by the first liquid 7 additionally being drunk if necessary to successively increase the insertion amount of the first liquid 7 inside the stomach 3 so that the position of the interfacial boundary 12 gradually rises. Also in this case, the imaging region by the capsule endoscope 4 can be changed only by changing the position of the interfacial boundary 12 inside the stomach 3 in combination with a slight posture change of the subject 2 itself each time the first liquid 7 is added so that observations inside the stomach 3 can be made without omission.

Figure 7:
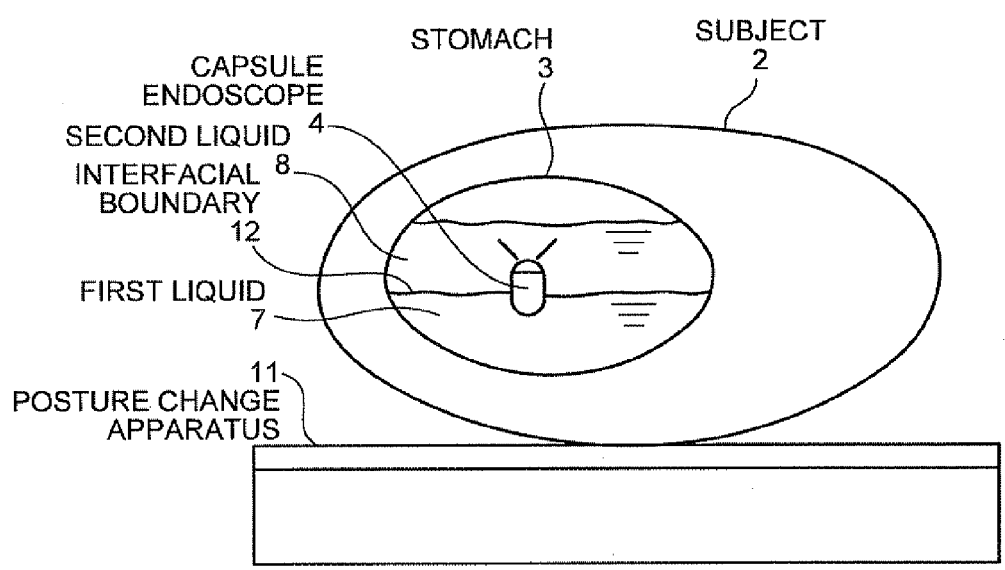
FIG. 7 is a schematic diagram sectionally showing the appearance inside the stomach during observation when a posture is changed to a face-up position.

Further, the imaging region by the capsule endoscope 4 can considerably be changed by significantly changing the position of the interfacial boundary 12 inside the stomach 3 in combination with a considerable posture change of the subject 2 by means of the posture change apparatus 11 so that observations inside the whole stomach 3 can be made more thoroughly without omission. FIG. 7 is a schematic diagram sectionally showing the appearance inside the stomach 3 during observation when the posture of the subject 2 is changed from a standing position to a face-up position by, for example, rotating the posture change apparatus 11 by 90 degrees to move down the posture change apparatus 11. That is, while the capsule endoscope 4 imaging upward images and observes upward inside the stomach 3 in a standing position, the capsule endoscope 4 can image and observe a front-side inner wall (or a back-side inner wall) in a face-up position shown in FIG. 7. Further, the posture may be changed to a lateral position.

Next, an example of processing by the control unit 41 of image data inside the stomach 3 picked up by the capsule endoscope 4 while the floating position or floating posture of the capsule endoscope 4 at the interfacial boundary 12 being changed accompanied by appropriate height adjustments of the interfacial boundary 12 position or a posture change will be described with reference to FIG. 8 and FIG. 9. In the first embodiment, the capsule endoscope 4 contains the acceleration sensor 25 or the angular velocity sensor 26 and thus, when the capsule endoscope 4 continuously picks up images containing a common portion while changing the floating position or floating posture, a relative movement magnitude about how much the capsule endoscope 4 can be understood. Therefore, a panorama image can be created by combining together images in such a way that a common portion of an image is superimposed on that of another image by using technologies such as epipolar geometry and template matching.

Figure 8:
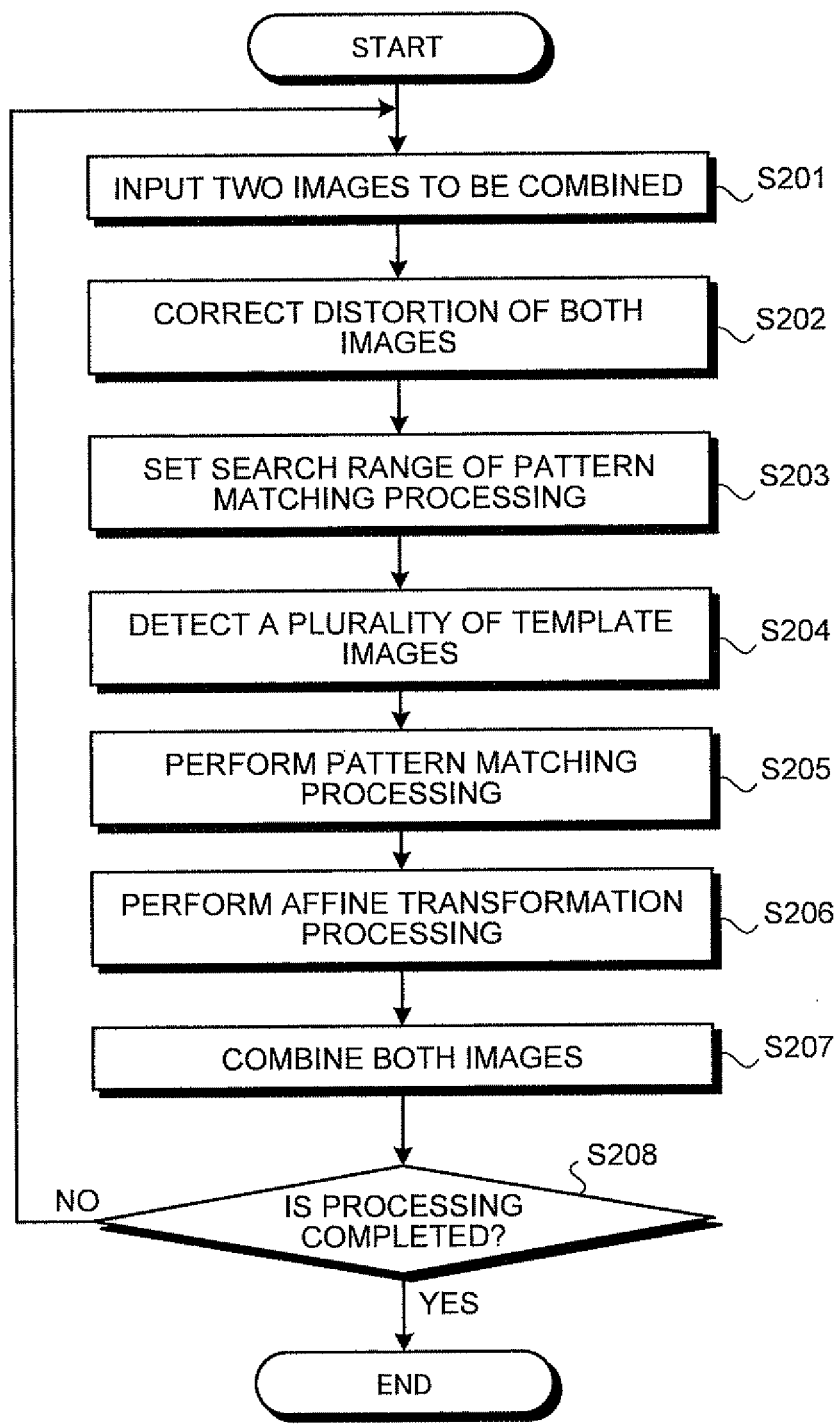
FIG. 8 is an outline flow chart exemplifying image combination processing.
Figure 9:
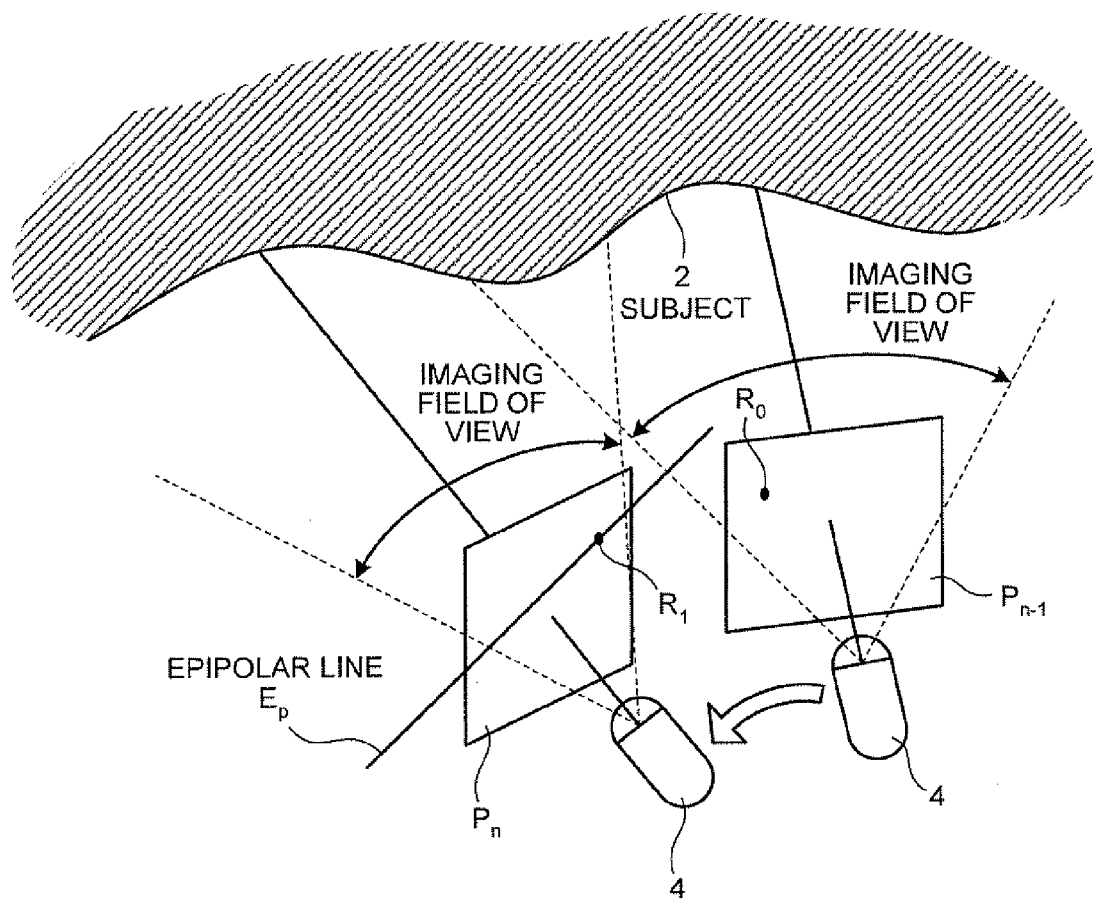
FIG. 9 is an explanatory diagram exemplifying a search range setting using epipolar geometry.

FIG. 8 is an outline flow chart exemplifying image combination processing performed by the image combining unit 41d in the control unit 41. Roughly, epipolar geometry is used to decide a search range of template matching and then, a plurality of images are combined together by template matching. First, two continuous images $P_n$, $P_{n-1}$ to be combined are input (step S201). Then, distortion corrections of these two images $P_n$, $P_{n-1}$ are made to superimpose them exactly (step S202). Further, the search range to limit the range in which pattern-matching processing is performed is calculated and set (step S203).

A decision of the search range is intended to increase the processing speed by roughly detecting an overlapping portion of imaging regions when the capsule endoscope 4 is displaced, thereby limiting the range of image synthesis thereafter, and epipolar geometry is used in the first embodiment to decide the search range. FIG. 9 is an explanatory diagram exemplifying a search range setting using epipolar geometry. That is, if the capsule endoscope 4 is displaced from a position where the image $P_{n-1}$ is picked up to that where the image $P_n$ is picked up, while a point on the image $P_n$ after the movement corresponding to a reference point $R_0$ on the image $P_{n-1}$ before the movement is not determined as a single point because the depth of imaging region is not known, but epipolar geometry can be used to limit a point $R_1$ corresponding to the reference point $R_0$ before the movement to an epipolar line Ep on the image $P_n$ after the movement. The amount of change of position information or posture information based on an acceleration or angular velocity detected by the acceleration sensor 25 or the angular velocity sensor 26 is referenced as a relative movement magnitude in this case of how much the capsule endoscope 4 has moved between $P_n$ and $P_{n-1}$. Thus, an overlapping portion of the images $P_n$, $P_{n-1}$ is decided by determining the epipolar line Ep on the image $P_n$ after the movement and deciding a spatial relationship between endpoints (for example, an upper left endpoint and a lower right endpoint) of the image $P_n$ and the epipolar line Ep to decide the search range.

Next, a plurality of template images is detected (step S204) and pattern-matching processing is performed (step S205). That is, a plurality of template images is created from within the image $P_n$ within the set search range and a plurality of template images is cut out from the image $P_{n-1}$ to be synthesized to find corresponding points by pattern matching of these. Here, since the number of unknown parameters of affine transformation described later is 6, six or more template images are used to find six or more corresponding points. Then, affine transformation processing in which a relationship between both images $P_n$, $P_{n-1}$ to be synthesized is defined as affine transformations of rotation and translation is performed (step S206). In this processing, six affine parameters are calculated by the method of least squares. Then, the determined six affine parameters are used to convert the image $P_{n-1}$ to be synthesized into x, y coordinates in the Cartesian coordinate system for synthesis with the image $P_n$ (step S207). The above processing is repeated for all images to be processed (step S208).

With the above image combination processing, a plurality of images can be recognized as a continuous image with common portions of one image superimposed on those of another image and therefore, a diagnosis inside the stomach 3 imaged while changing the floating position or floating posture of the capsule endoscope 4 is made easier.

The processing at step S207 is simple synthesis processing and a flat synthesized image is produced. Thus, if the horizontal size of the synthesized image synthesized as described above is L and the vertical size is H, cylindrical mapping in which the synthesized image is pasted to a cylinder of the diameter $R=L/\pi$ and the height H may be performed so that transformations between the cylindrical coordinate system and the Cartesian coordinate system are performed. If such a synthesized image is caused to be displayed in the display unit 9, the inside of the cylinder can be observed from a virtual viewpoint as if to view the inside of the stomach 3 from the capsule endoscope 4, making a diagnosis inside the stomach 3 still easier.

Figure 10:
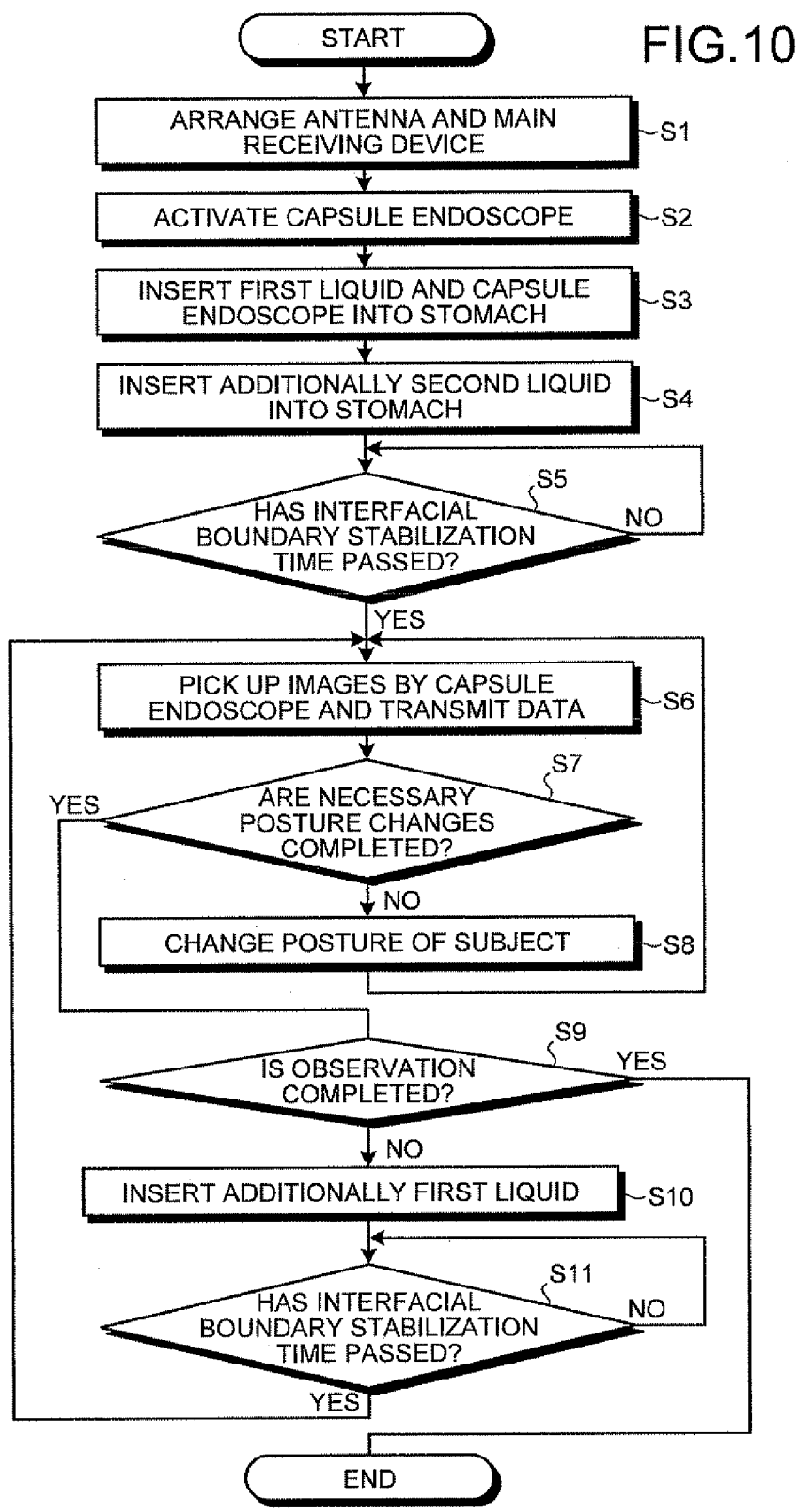
FIG. 10 is an outline flow chart showing a procedure for an intra-stomach observation method in the first embodiment.

Next, the procedure for the intra-stomach observation method (intra-subject observation method) according to the first embodiment described above is summarized in FIG. 10. FIG. 10 is an outline flow chart showing the procedure for the intra-stomach observation method in the first embodiment. First, before starting an observation, the antenna 6a for receiving a signal from the capsule endoscope 4 is arranged at a predetermined position of the subject 2 and also the main receiving device 6b is arranged near the subject 2 (step S1). Next, the capsule endoscope 4 stored inside the feeding apparatus 1 is activated by a separate magnet or the like (step S2).

Then, the first liquid 7 is inserted into the stomach 3 together with the enclosed capsule endoscope 4 by being swallowed from the mouth 1d of the feeding apparatus 1 (step S3). At this point, the subject 2 shall be in a standing position (or a sitting position) to make swallowing easier. Next, the second liquid 8 is inserted into the stomach 3 by being swallowed from the mouth 1f of the feeding apparatus 1 (step S4). At this point, the capsule endoscope 4 is not required to be swallowed simultaneously with the first liquid 7, but the capsule endoscope 4 is made easier to swallow by the capsule endoscope 4 being swallowed together with the first liquid 7. The capsule endoscope 4, the first liquid 7, and the second liquid 8 may be swallowed in any order and thus, they may be swallowed in order of ease of swallowing. Then, it is necessary to wait for several minutes until the interfacial boundary 12 inside the stomach 3 stabilizes (step S5).

Accordingly, an observable state as shown, for example, in FIG. 5 or FIG. 6(a) is created, the capsule endoscope 4 is caused in this state to transmit intra-subject image data acquired by the capsule endoscope 4 through image pick-up out of the subject 2, and the receiving apparatus 6 is caused to receive the intra-subject image data (step S6). Subsequently, before the required number of times of posture change is completed (step S7: Yes), the posture of the subject 2 is changed at appropriate timing (step S8) to repeat the imaging processing at step S6 in the changed posture. If the observation of the stomach 3 for the subject 2 is not completed (step S9: No), the first liquid 7 is additionally inserted into the stomach 3 at appropriate timing (step S10). Then, it is necessary to wait for several minutes until the interfacial boundary 12 inside the stomach 3 stabilizes (step S11: Yes) before repeating processing at step S6 and thereafter. If the observation of the stomach 3 for the subject 2 is completed (step S9: Yes), observation processing is terminated. At this point, it is desirable that the posture of the subject 2 be changed to a right lateral position to promote movement of the capsule endoscope 4 inserted into the stomach 3 together with the first liquid 7 and the second liquid 8 toward the pyloric part of stomach 3b.

First Modification

Figure 11:
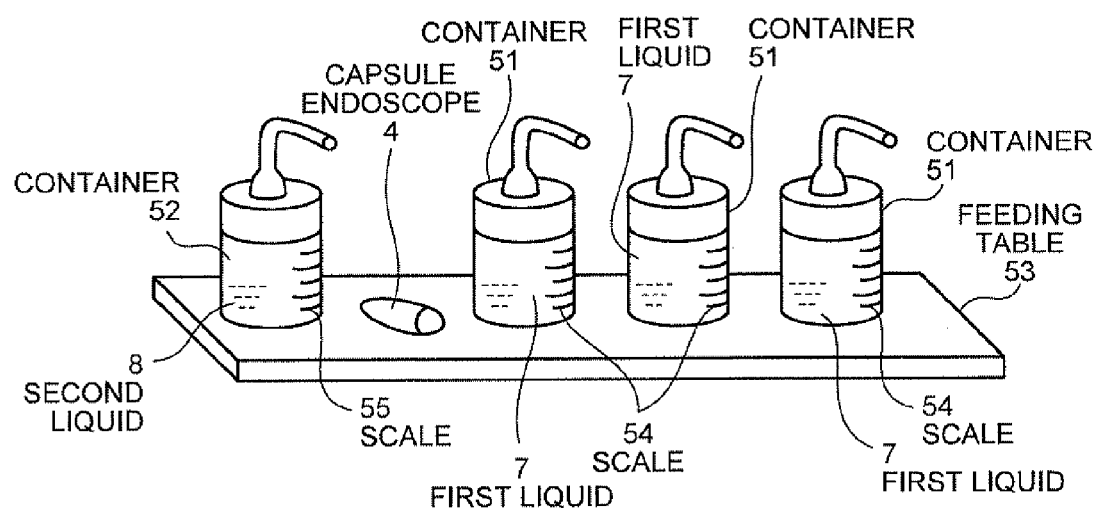
FIG. 11 is a schematic perspective view showing a first modification of a feeding method of the body-inserted materials.

While the body-inserted material 5 formed of the capsule endoscope 4, the first liquid 7, and the second liquid 8 is caused to be inserted into the subject 2 together from the packaged feeding apparatus 1 in the first embodiment, the present invention is not limited to the packaged feeding apparatus 1 and any feeding method of the body-inserted material 5 may be used. FIG. 11 is a schematic perspective view showing a modification of the feeding method of the body-inserted material 5. One or additional several bottle-shaped containers 51 storing the first liquid 7 and one (or several) bottle-shaped container 52 storing the capsule endoscope 4 and the second liquid 8 may be prepared on a feeding table 53 attached to the posture change apparatus 11 before being fed to the subject 2. In this case, it is preferable that the containers 51 and 52 have scales 54 and 55 respectively to make insertion amounts easier to understand. Or, instead of the bottle-shaped containers 51 and 52, containers such as cups may be used.

Second Modification

Figure 12A:
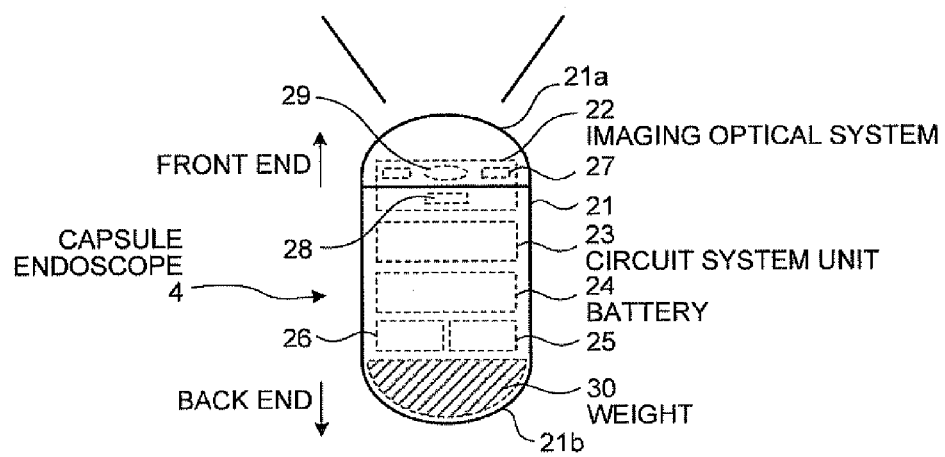
FIG. 12A is a side view showing the outline configuration of a second modification of the capsule endoscope whose front-end side is relatively lighter.
Figure 12B:
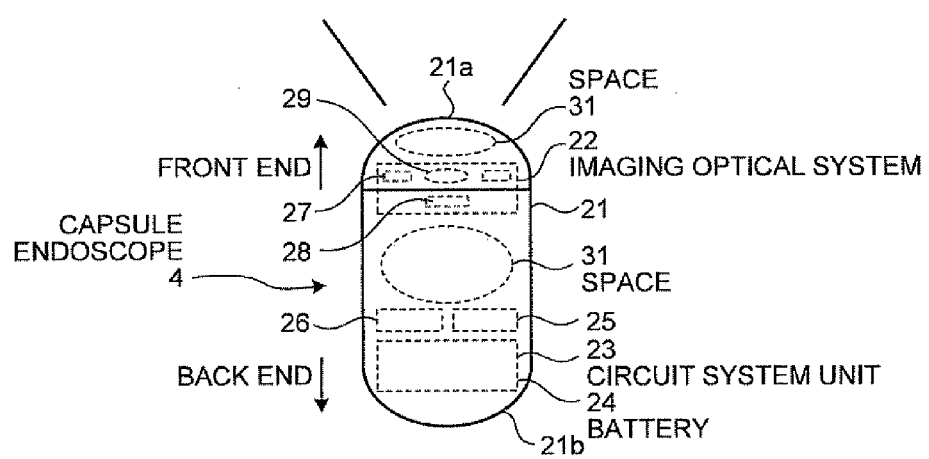
FIG. 12B is a side view showing the outline configuration of another second modification of the capsule endoscope whose front-end side is relatively lighter.

The capsule endoscope 4 in which the battery 24 is disposed on the back-end side is used in the first embodiment to create a weight balance in which the front-end side is relatively lighter, but the present invention is not limited to such an arrangement example and any capsule endoscope having a weight balance in which the front-end side is relatively lighter may be used. For example, as shown in FIG. 12A, the capsule endoscope 4 in which, instead of the battery 24, a weight 30 is disposed on the back-end side or, as shown in FIG. 12B, the capsule endoscope 4 in which a space 31 is secured on the front-end side to make the front-end side lighter may be used.

Third Modification

Further, the first embodiment is described by taking the capsule endoscope 4 imaging upward with a weight balance in which the front-end side is relatively lighter as an example, but if downward imaging is intended, a monocular capsule endoscope with a weight balance in which the front-end side is relatively heavier may be used. FIG. 13A to FIG. 13C are each a side view showing the outline configuration of a monocular capsule endoscope 40 with a weight balance in which the front-end side is relatively heavier. FIG. 13A shows a configuration example in which a heavy component such as the battery 24 is disposed on the front-end side, FIG. 13B shows an example in which the weight 30 is disposed on the front-end side, and FIG. 13C shows an example in which the space 31 is provided on the back-end side.

Incidentally, the monocular capsule endoscope 40 with a weight balance in which the front-end side is relatively heavier, as exemplified in FIG. 13A to FIG. 13C, floats at the interfacial boundary 12 between the first liquid 7 and the second liquid 8 in a standing position to image the inner wall of the stomach 3 in a downward direction through the first liquid 7 always positioned on the lower side. Thus, the first liquid 7, instead of air space, fills a space around the front cover 21a and therefore, even if the surface of the front cover 21a is scratched or dirty, more satisfactory images can be obtained than when imaged via the air space because such a scratch or dirt becomes inconspicuous. Moreover, even for downward imaging by the capsule endoscope 40 floating at the interfacial boundary 12 in a stage in which the amount of the first liquid 7 is small, as shown, for example, in FIG. 6(a), images are picked up in a state in which the inner wall on the lower side of the stomach 3 is extended/dilated in a wide range with more liquids inserted into the stomach 3 after, in addition to the first liquid 7, the second liquid 8 being inserted, so that satisfactory observations can be made by securing a sufficient field of view inside the stomach 3, which is a wide organ. That is, though the same state can be secured by one liquid if the first liquid of an amount equal to that of (first liquid+second liquid) is inserted into the stomach and control to cause a capsule endoscope to sink to a desired position in the liquid is performed in a state as shown in FIG. 6(a), according to the present invention, the state can easily be realized only by controlling the position of the interfacial boundary 12 without performing control to cause the capsule endoscope to sink.

Moreover, as described in examples of the monocular capsule endoscopes 4, 40 capable of imaging only in the front-end direction, a monocular capsule endoscope in the first embodiment may be capable of imaging, in addition to the front-end direction only, for example, only in a perspective direction on the front-end side or a circumferential direction on the front-end side. Further, the capsule endoscope is not limited to the monocular one and may be a binocular capsule endoscope capable of imaging both in the front-end direction and the back-end direction. The imaging direction of a binocular capsule endoscope can also be made always constant with respect to the gravity direction by changing the balance of the center of gravity in the front-back direction to be decentered the center of gravity so that the binocular capsule endoscope floats at the interfacial boundary 12 always in a standing position, allowing stable imaging. Imaging in this case may be in both front and back directions or in one desired direction.

Though the first embodiment is described by taking the stomach 3 as a desired organ of the subject 2 as an observation example, the present embodiment is applicable also to observation of organs having a relatively wide lumen such as the large intestine.

Second Embodiment

Figure 14:
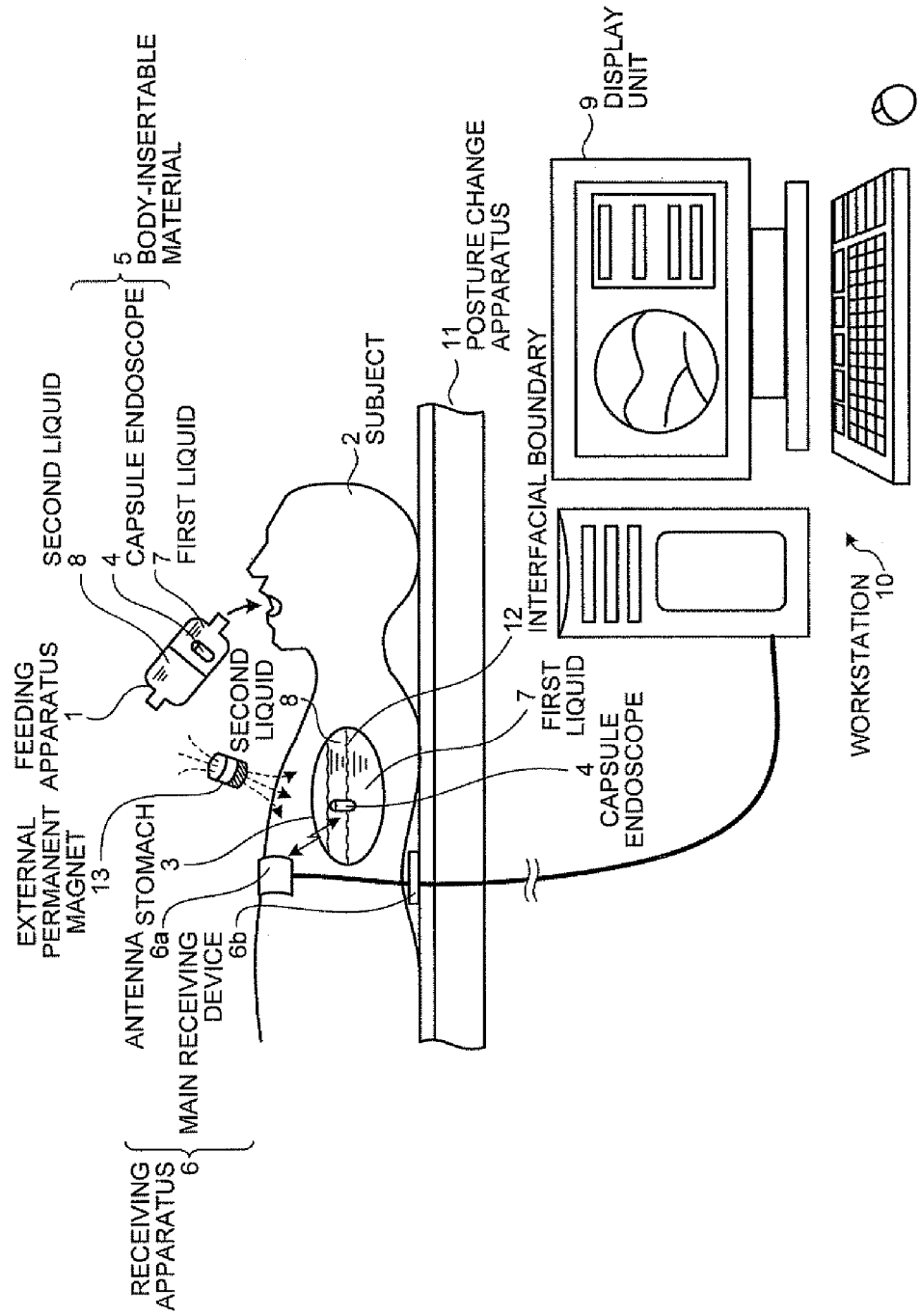
FIG. 14 is a schematic diagram showing the overall configuration of a radio intra-subject observation system in a preferred second embodiment of the intra-subject observation system according to the present invention.

Next, a second embodiment of the present invention will be described with reference to FIG. 14. The same reference numerals are attached to the same components as those shown in FIG. 1 to FIG. 13 and a description thereof will not be repeated here. FIG. 14 is a schematic diagram showing the overall configuration of a radio intra-subject observation system in the preferred second embodiment of the intra-subject observation system according to the present invention. The intra-subject observation system uses a capsule endoscope as an example of the capsule medical apparatus. In FIG. 14, like in FIG. 1, the intra-subject observation system comprises the body-inserted material 5 including the capsule endoscope 4 for picking up images inside a body cavity to transmit data such as a video signal and the like after being inserted into a desired organ such as the stomach 3 of the subject 2 by the feeding apparatus 1, and the receiving apparatus 6 used for reception processing of a radio signal transmitted from the capsule endoscope 4 inserted into the stomach 3. The receiving apparatus 6 is used while disposed near the subject 2 to perform reception processing of a radio signal received from the capsule endoscope 4. The body-inserted material 5 is comprised of, as described with reference to FIG. 2, the capsule endoscope 4, the first liquid 7, and the second liquid 8 prepared inside the feeding apparatus 1. The intra-subject observation system in the second embodiment also comprises the display unit 9 for displaying images inside the body cavity based on a video signal received by the receiving apparatus 6 and the workstation 10 controlling the whole system.

Moreover, the intra-subject observation system in the second embodiment comprises an external permanent magnet 13, which is a capsule displacement driving device serving as a magnetic field applicator for changing the floating position or floating posture of the capsule endoscope 4 floating at the interfacial boundary 12 between the first liquid 7 and the second liquid 8, which are inserted into the stomach 3 together with the first liquid 7 and the second liquid 8, and the posture change apparatus 11 for changing the posture of the subject 2 to be observed. The external permanent magnet 13 is provided freely disposably at an arbitrary and desired position on the body surface of the subject 2 by being held by the hand of a health care professional such as a physician.

Figure 15:
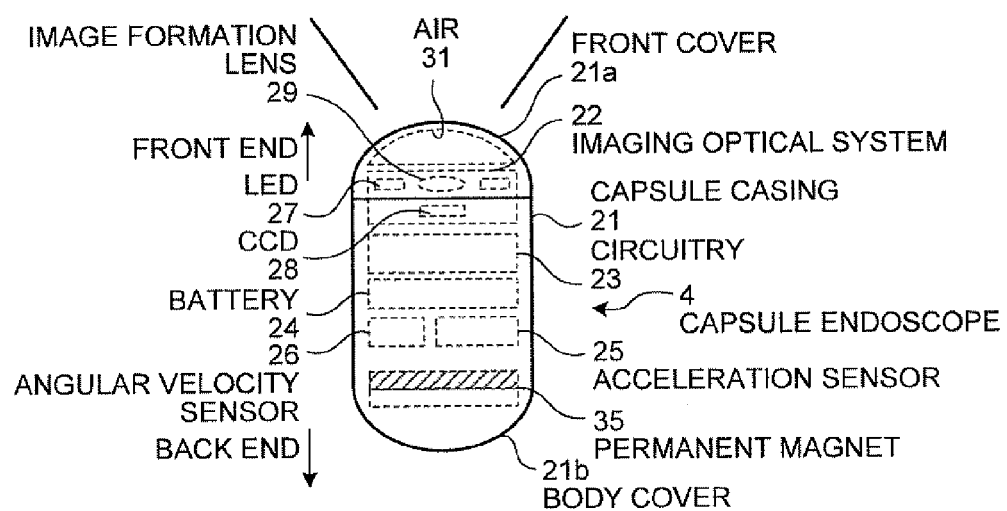
FIG. 15 is a side view showing the outline configuration of a capsule endoscope.

The capsule endoscope 4 will be described with reference to FIG. 15. FIG. 15 is a side view showing the outline configuration of the capsule endoscope 4. Capsule endoscope 4 in the second embodiment is, like one shown, for example, in FIG. 3, a monocular capsule endoscope having the capsule casing 21 and the imaging optical system 22 and comprises, inside the capsule casing 21, the circuitry 23 including a board, circuit components, and a transmitting antenna, the battery 24, the acceleration sensor 25, the angular velocity sensor 26 and also a magnetic body such as a permanent magnet 35.

The capsule casing 21, the imaging optical system 22, the acceleration sensor 25, and the angular velocity sensor 26 are as described with reference to FIG. 3 or the like. The permanent magnet 35 provided as an example of magnetic body is magnetized in such a way that N and S poles thereof are positioned in the longitudinal direction of the capsule endoscope 4. The permanent magnet 35 is a heavy component inside the capsule endoscope 4 and the center of gravity of the capsule endoscope 4 in the second embodiment is decentered toward the back-end side by allocating the permanent magnet 35 on the back-end side inside the capsule casing 21 and securing the space 31 inside the front cover 21a on the front-end side to change the weight balance in the front-back direction so that the front-end side becomes relatively lighter. To create such a weight balance, the battery 24 or a heavy component of a different member such as a weight may be provided on the back-end side. A magnetic body contained in the capsule endoscope 4 is not limited to the permanent magnet 35 and a coil or electromagnet may also be used.

Figure 16:
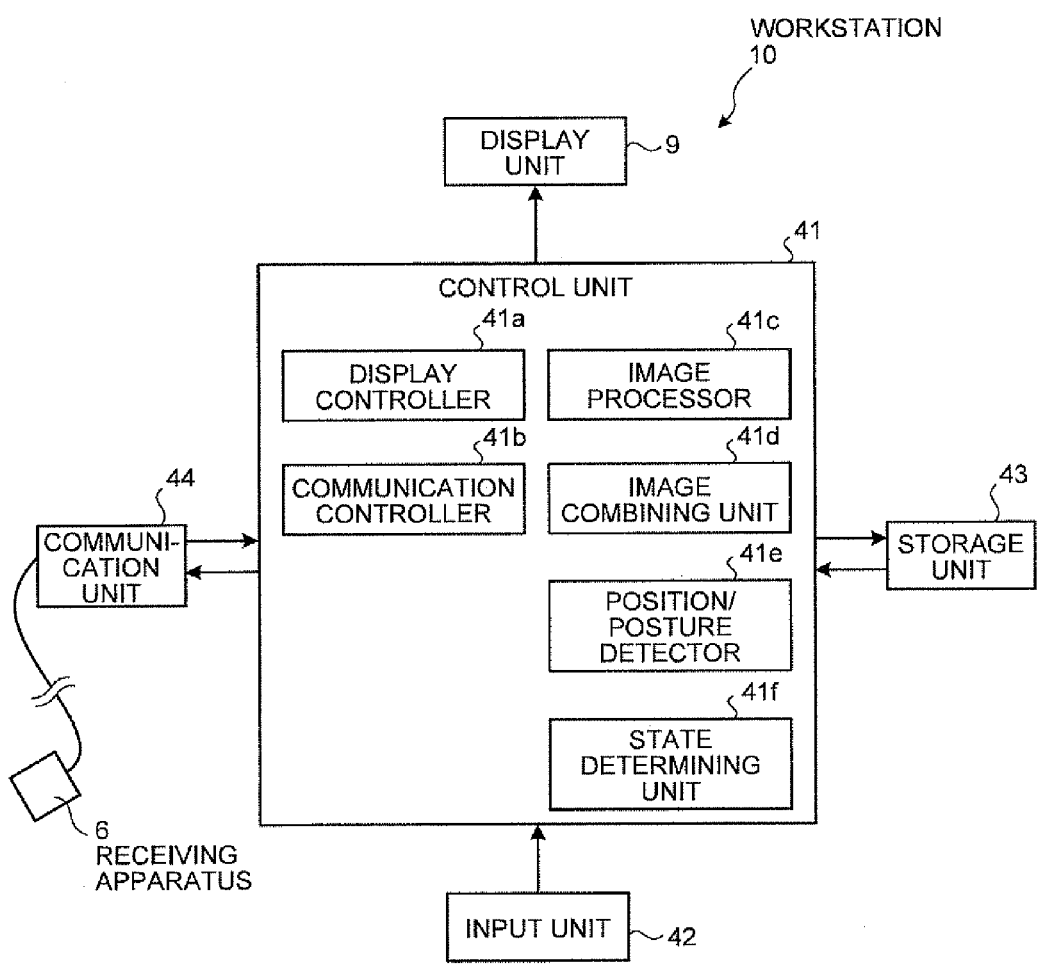
FIG. 16 is a schematic block diagram exemplifying the configuration of a workstation.

Here, a configuration example of the above-described workstation 10 will be described with reference to FIG. 16. FIG. 16 is a schematic block diagram exemplifying the configuration of the workstation 10. The workstation 10 in the second embodiment comprises, similarly as described with reference to FIG. 4, the control unit 41, the input unit 42 connected to the control unit 41, the display unit 9, the storage unit 43, and the communication unit 44. The control unit 41 is constructed of a computer configuration such as a CPU, ROM, and RAM and comprises the state determining unit 41f, in addition to execution units of various functions such as the display controller 41a, the communication controller 41b, the image processor 41c, the image combining unit 41d, and the position/posture detector 41e. The state determining unit 41f is used to determine the status of the capsule endoscope 4 whether the position or posture of the capsule endoscope 4 is displaced in response to an applied external magnetic field when the external permanent magnet 13 is brought closer to the capsule endoscope 4 based on detection output from the acceleration sensor 25.

Figure 17:
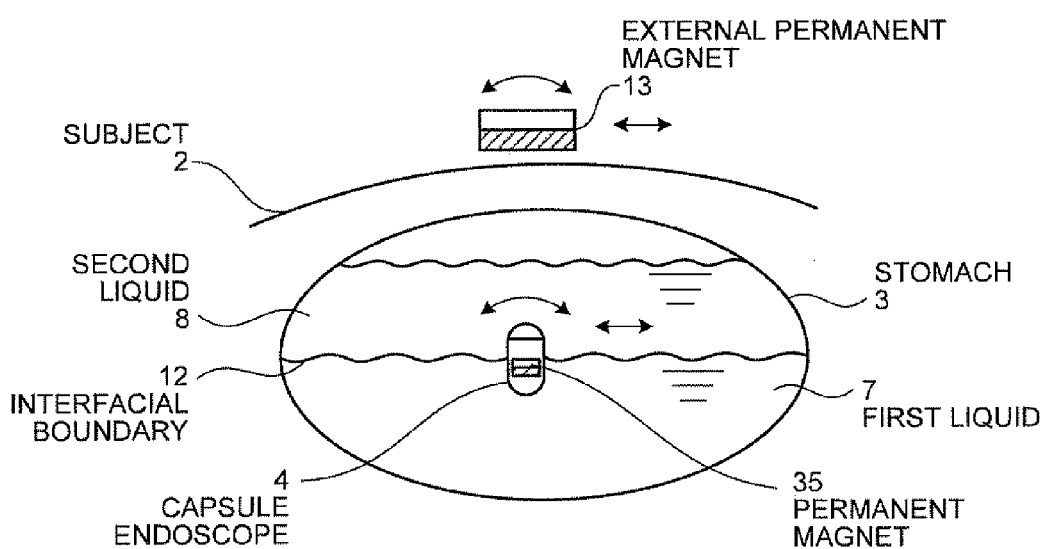
FIG. 17 is a schematic diagram sectionally showing the appearance of observation inside the stomach of a subject in the face-up position.

The observation method inside the stomach 3 according to the second embodiment is the same as that described with reference to FIG. 5 to FIG. 8. Next, an observation method inside the stomach 3 using the external permanent magnet 13 will be described with reference to FIG. 14 and FIG. 17. FIG. 17 is a schematic diagram sectionally showing the appearance of observation inside the stomach 3 of the subject 2 in the face-up position. As described above, the capsule endoscope 4 images the inner wall while floating at the interfacial boundary 12 between the first liquid 7 and the second liquid 8 inside the stomach 3. Here, in the second embodiment, the external permanent magnet 13 held by a medical worker is allocated outside the subject 2 so that an external magnetic field can be applied to the permanent magnet 35 inside the capsule endoscope 4. The permanent magnet 35 is magnetized in the longitudinal direction of the capsule endoscope 4 and, the floating position at the interfacial boundary 12 of the capsule endoscope 4 can be forced to be displaced in a horizontal plane by selecting polarity of the external permanent magnet 13 and allocating the external permanent magnet 13 opposite to the permanent magnet 35, and then moving the allocation position of the external permanent magnet 13 in the horizontal plane as indicated by an arrow in the horizontal direction in FIG. 17 while applying an external magnetic field in a direction of attraction. If the external permanent magnet 13 is displaced by rotation as indicated by an arrow in a rotational movement direction in FIG. 17 at the allocation position of the external permanent magnet 13, the direction of the external magnetic field applied to the permanent magnet 35 is also tilted from the vertical direction, thereby forcing the floating posture at the interfacial boundary 12 of the capsule endoscope 4 to be displaced in the horizontal plane.

Accordingly, the imaging position and imaging direction inside the stomach 3 by the capsule endoscope 4 can be changed by arbitrarily and forcibly displacing the floating position or floating posture of the capsule endoscope 4 at the interfacial boundary 12 by the external permanent magnet 13 and therefore, observations inside the stomach 3 can be made exhaustively in a short time and an observation of a region desired by a physician or the like can easily be realized. The position control of the capsule endoscope 4 in the gravity direction in this case can easily be realized by gradually increasing the above-described amount of the first liquid 7 inserted into the stomach 3. Further, observations inside the stomach 3 can be made more thoroughly without omission by making observations while combining posture changes of the subject 2 described above and forcing the floating position or floating posture of the capsule endoscope 4 to be displaced for each desired posture. Particularly in the second embodiment, the floating position or floating posture of the capsule endoscope 4 is forced to change and thus, the whole stomach 3 can be observed exhaustively with less posture change.

Such changes of the floating position or floating posture of the capsule endoscope 4 are relative to the capsule endoscope 4 floating at the interfacial boundary 12 between liquids and can be controlled with a small magnetic force because resistance to change of the position or posture is small. Particularly the capsule endoscope 4 in the second embodiment is constructed on the basis of a standing position with the arrangement of the center of gravity decentered toward the back-end side and therefore, the floating posture while maintaining an upward direction can easily be changed with stability like an oscillating operation. Thus, the permanent magnet 35 and the external permanent magnet 13 that are small in size may be used to realize the second embodiment.

If the arrangement of the center of gravity of the capsule endoscope 4 is the center thereof or near the center and the polarity of an external magnetic field applied to the permanent magnet 35 by the external permanent magnet 13 is the direction of attraction, control of the floating position or floating posture described above can be realized. If the polarity of the applied magnetic field is switched to a direction of repulsion, after the capsule endoscope 4 is flipped from top to bottom (the polarity of the permanent magnet 35 is flipped from top to bottom), control of the floating position or floating posture described above becomes realizable and, in the end, the capsule endoscope 4 can be caused to make a turn vertically.

Incidentally, the capsule endoscope 4 in the second embodiment contains the acceleration sensor 25 and the position of the capsule endoscope 4 can be grasped. Thus, whether the capsule endoscope 4 reacts to an external magnetic field when the external permanent magnet 13 is brought closer to the capsule endoscope 4, that is, the status whether the position is displaced can be confirmed. The state determining unit 41f in the control unit 41 performs processing of the status determination whether the capsule endoscope 4 is guided as desired and causes the display unit 9 to display a determination result whether the capsule endoscope 4 reacted to the external magnetic field. Accordingly, whether the external permanent magnet 13 in use has sufficient magnetic field strength and how strong the external permanent magnet 13 is pressed against the body surface can be confirmed so that omission due to excessive or insufficient applied magnetic field strength can be prevented.

The component used to determine whether the capsule endoscope 4 reacted to an external magnetic field is not limited to the acceleration sensor 25 and a sensor, a magnetic sensor or the like having a position detection function may also be used. Concerning the external permanent magnet 13, it is preferable to freely selectably prepare a plurality of types of permanent magnets having different magnetic field strengths and selectively use the permanent magnet in accordance with a result of such a status determination (an excessive or insufficient applied external magnetic field). The field strength of the external permanent magnet 13 to be used may also be decided by fitting to the physique of the subject 2. That is, the magnetic field strength of the external permanent magnet 13 to be used is decided in accordance with the weight, height, waist measurement and the like of the subject 2. If, at this point, a sheet to decide the external permanent magnet 13 to be used based on values of the weight, height, waist measurement and the like of the subject 2 is prepared in advance, the selection is made appropriate and easier. Accordingly, more correct and efficient examinations can be made by absorbing individual differences due to the physique of the subject 2. Also, a program to decide the external permanent magnet 13 to be used by inputting the values of the weight, height, waist measurement of the subject 2 may be prepared. Or, instead of data such as the weight, height, and waist measurement, CT data acquired in advance by a CT scan or the like may be used.

Figure 18:
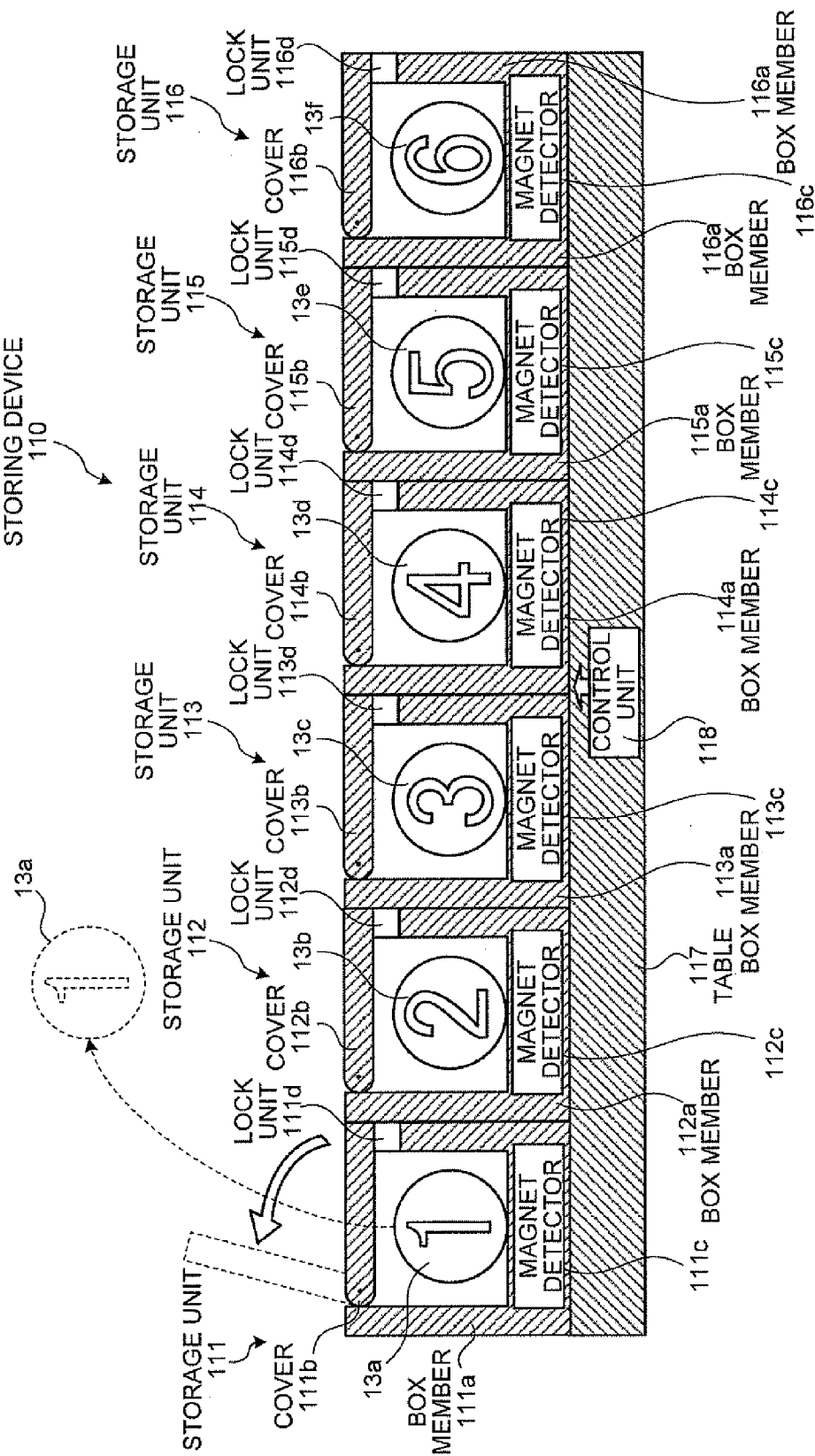
FIG. 18 is a schematic sectional view exemplifying the configuration of a storing device of a plurality of types of external permanent magnets.

When the plurality of types of the external permanent magnets 13 having different magnetic field strengths are used, it is preferable to provide a storing device for storage so that only one desired external permanent magnets 13 can be extracted. FIG. 18 is a schematic sectional view exemplifying the configuration of a storing device of a plurality of types of the external permanent magnets 13. Here, a storing device for storage of six types of external permanent magnets 13a to 13f will be exemplified.

As shown in FIG. 18, a storing device 110 has six storing units 111 to 116 for storing the external permanent magnets 13a to 13f separately, a table 117 for integrally connecting the storing units 111 to 116, and a control unit 118 for controlling each drive of opening and closing of the storing units 111 to 116. The external permanent magnets 13a to 13f shall be marked by magnet numbers 1 to 6 for specifying each. The external permanent magnets 13a to 13f shall have a stronger magnetic force with the increasing magnet number.

The storing unit 111 is used to store the external permanent magnet 13a of the magnet number 1. More specifically, the storing unit 111 has a box member 111a for storing the external permanent magnet 13a, a cover 111b for opening and closing an open end of the box member 111a, a magnet detector 111c for detecting the external permanent magnet 13a stored in the box member 111a, and a lock unit 111d for locking the cover 111b. The box member 111a is, for example, a member whose sectional view has a concave shape and the cover 111b is freely rotatably provided near the open end. The external permanent magnet 13a stored in the box member 111a is taken out and put in by opening/closing the cover 111b. When the external permanent magnet 13a is stored in the box member 111a, the magnet detector 111c detects a magnetic field or the weight of the external permanent magnet 13a and, based on a detection result, detects presence/absence of the external permanent magnet 13a in the box member 111a, The magnet detector 111c notifies the control unit 118 of the detection result of the external permanent magnet 13a. The lock unit 111d locks the cover 111b or unlocks the cover 111b based on control of the control unit 118.

Also, the storing units 112 to 116 are used to store the external permanent magnets 13b to 13f of the magnet numbers 2 to 6 respectively and have almost the same configuration and functions as those of the above storing unit 111. That is, the storing units 112 to 116 have box members 112a to 116a for storing the external permanent magnets 13b to 13f separately, covers 112b to 116b for opening and closing each open end of the box members 112a to 116a respectively, magnet detectors 112c to 116c for detecting the external permanent magnets 13b to 13f stored in the box members 112a to 116a respectively, and lock units 112d to 116d for locking the covers 112b to 116b respectively. In this case, the box members 112a to 116a have almost the same function as that of the box member 111a of the storing unit 111, and the covers 112b to 116b have almost the same function as that of the cover 111b of the storing unit 111. The magnet detectors 112c to 116c have almost the same function as that of the magnet detector 111c of the storing unit 111, and the lock units 112d to 116d have almost the same function as that of the lock unit 111d of the storing chamber 111.

The control unit 118 is on the table 117 to control each drive of the above magnet detectors 111c to 116c and the lock units 111d to 116d. More specifically, the control unit 118 acquires each detection result of the external permanent magnets 13a to 13f from the magnet detectors 111c to 116c and, based on each acquired detection result of the external permanent magnets 13a to 13f, control each drive of the lock units 111d to 116d. In this case, if the control unit 118 acquires detection results indicating presence of magnet from all the magnet detectors 111c to 116c, the control unit 118 performs drive control to unlock the lock units 111d to 116d.

If, on the other hand, the control unit 118 acquires a detection result indicating absence of magnet from one of the magnet detectors 111c to 116c, the control unit 118 performs drive control to unlock the storing unit having the magnet detector that provided notification of the detection result of absence of magnet, that is, the lock unit (one of the lock units 111d to 116d) of the storing unit from which an external permanent magnet has been taken out. At the same time, the control unit 118 performs drive control to lock the cover to each remaining storing unit having the magnet detector that provided notification of the detection result of presence of magnet, that is, the lock unit (one of the lock units 111d to 116d) of each storing unit storing an external permanent magnet.

The control unit 118 performs drive control to so that one of the external permanent magnets 13a to 13f stored in the storing units 111 to 116 respectively can be taken out and at the same time, a plurality of the external permanent magnets cannot be taken out. If, for example, as shown in FIG. 18, an examiner takes out the external permanent magnet 13a from the external permanent magnets 13a to 13f, the control unit 118 acquires a detection result of absence of magnet from the magnet detector 111c and also detection results of presence of magnet from the remaining magnet detectors 112c to 116c. In this case, the control unit 118 performs drive control to unlock the cover 116b to the lock unit 111d and also drive control to lock the covers 112b to 116b to the remaining lock units 112d to 116d. Accordingly, the examiner can take out only a needed external permanent magnet from the storing device 110 and, for example, a situation in which a plurality of external permanent magnets are unintentionally brought closer to the subject 2 into which the capsule endoscope 4 has been inserted can be prevented so that observations inside the subject 2 can be made more safely.

An example of processing by the control unit 41 of image data inside the stomach 3 picked up by the capsule endoscope 4 while the floating position or floating posture of the capsule endoscope 4 at the interfacial boundary 12 being forced to change successively accompanied by appropriate height adjustments of the interfacial boundary 12 position and a posture change is also as described with reference to FIG. 8 and FIG. 9 for the second embodiment.

Figure 19:
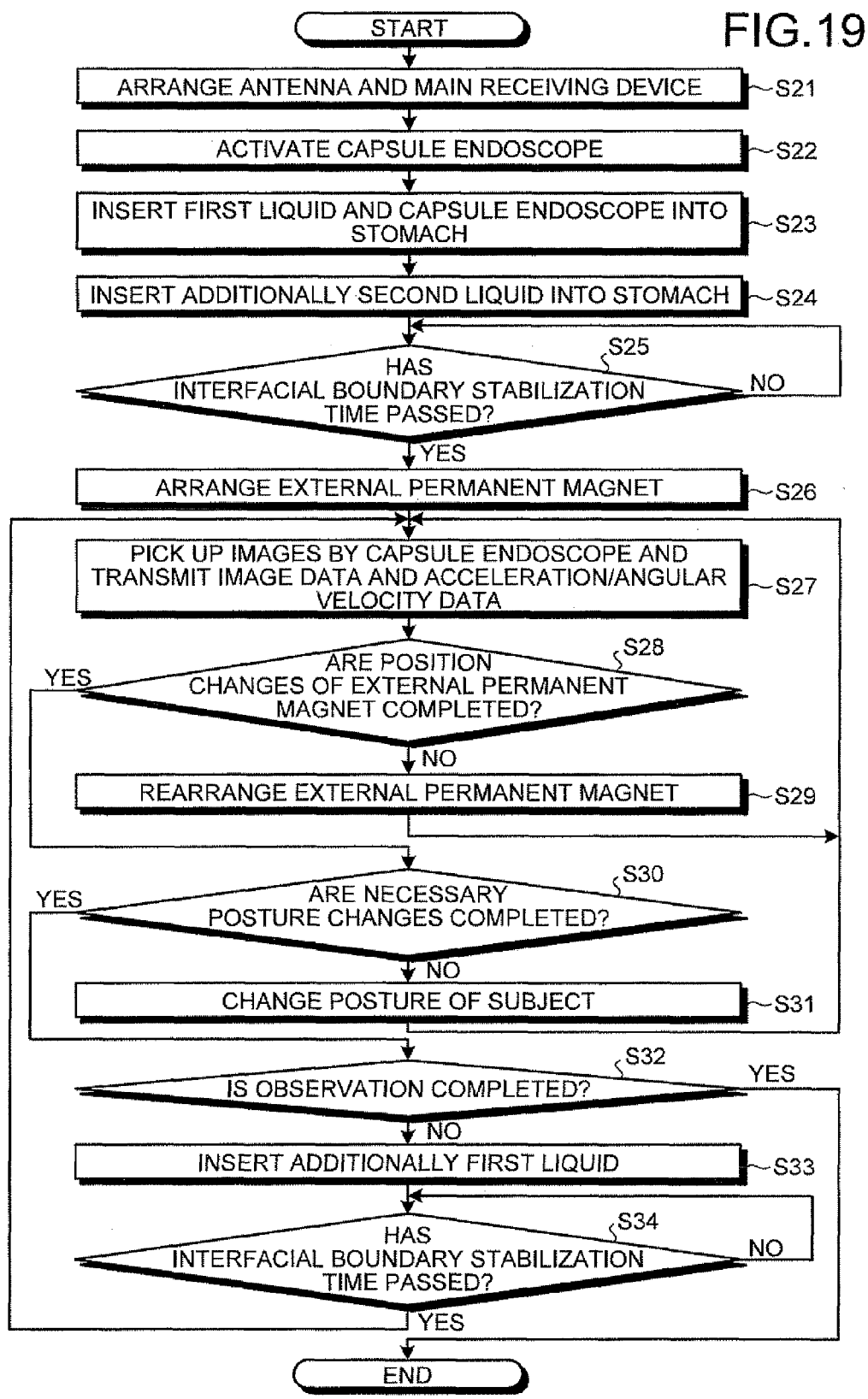
FIG. 19 is an outline flow chart showing the procedure for an intra-stomach observation method in the second embodiment.

Next, the procedure for the intra-stomach observation method (intra-subject observation method) according to the second embodiment described above is summarized in FIG. 19. FIG. 19 is an outline flow chart showing the procedure for the intra-stomach observation method in the second embodiment. First, before starting an observation, the antenna 6a for receiving a signal from the capsule endoscope 4 is arranged at a predetermined position of the subject 2 and also the main receiving device 6b is arranged near the subject 2 (step S21). Next, the capsule endoscope 4 stored inside the feeding apparatus 1 is activated by a separate magnet or the like (step S22).

Then, the first liquid 7 is inserted into the stomach 3 together with the enclosed capsule endoscope 4 by being swallowed from the mouth 1d of the feeding apparatus 1 (step S23). At this point, the subject 2 shall be in a standing position (or a sitting position) to make swallowing easier. Next, the second liquid 8 is inserted into the stomach 3 by being swallowed from the mouth 1f of the feeding apparatus 1 (step S24). At this point, the capsule endoscope 4 is not required to be swallowed simultaneously with the first liquid 7, but the capsule endoscope 4 is made easier to swallow by the capsule endoscope 4 being swallowed together with the first liquid 7. The capsule endoscope 4, the first liquid 7, and the second liquid 8 may be swallowed in any order and thus, they may be swallowed in order of ease of swallowing. Then, it is necessary to wait for several minutes until the interfacial boundary 12 inside the stomach 3 stabilizes (step S25).

Then, the external permanent magnet 13 is arranged at a desired position outside the subject 2 (step S26) and the floating position or floating posture of the capsule endoscope 4 floating at the interfacial boundary 12 is decided. Accordingly, an observable state as shown, for example, in FIG. 17, is created, the capsule endoscope 4 is caused in this state to transmit intra-subject image data acquired by the capsule endoscope 4 through image pick-up out of the subject 2, and the receiving apparatus 6 is caused to receive the intra-subject image data (step S27). When images are being picked up, the capsule endoscope 4 is also caused to transmit acceleration information and angular velocity information detected by the acceleration sensor 25 and the angular velocity sensor 26 out of the subject 2 and the receiving apparatus 6 is caused to receive the information. Then, before change control of needed floating positions and floating postures of the capsule endoscope 4 by the external permanent magnet 13 is completed (step S28: Yes), needed floating positions and floating postures of the capsule endoscope 4 are forced to change by the external permanent magnet 13 at appropriate timing (step S29) to repeat the imaging processing at step S27 in the changed position or posture.

Subsequently, before needed posture changes are completed (step S30: Yes), the posture of the subject 2 is changed at appropriate timing (step S31) and the processing at steps S27 to S29 is repeated. Then, if the observation of the stomach 3 for the subject 2 is not completed (step S32: No), the first liquid 7 is additionally inserted into the stomach 3 at appropriate timing (step S33). Then, it is necessary to wait for several minutes until the interfacial boundary 12 inside the stomach 3 stabilizes (step S34: Yes) before repeating processing at step S27 and thereafter. If the observation of the stomach 3 for the subject 2 is completed (step S32: Yes), observation processing is terminated. At this point, it is desirable that the posture of the subject 2 be changed to a right lateral position to promote movement of the capsule endoscope 4 inserted into the stomach 3 together with the first liquid 7 and the second liquid 8 toward the pyloric part of stomach 3b. Further, the time before the capsule endoscope 4 that has completed observation being excreted can be shortened if the capsule endoscope 4 is moved to the pyloric part of stomach 3b by guiding the capsule endoscope 4 while applying an external magnetic field of the external permanent magnet 13.

While the body-inserted material 5 formed of the capsule endoscope 4, the first liquid 7, and the second liquid 8 is caused to be inserted into the subject 2 together from the packaged feeding apparatus 1 in the second embodiment, the present invention is not limited to the packaged feeding apparatus 1 and any feeding method of the body-inserted material 5 may be used and, for example, the feeding method described with reference to FIG. 11 may be used.

Fourth Modification

The second embodiment is described by taking the capsule endoscope 4 imaging upward with a weight balance in which the front-end side is relatively lighter as an example, but if downward imaging is intended, a monocular capsule endoscope with a weight balance in which the front-end side is relatively heavier may be used. FIG. 20 is a side view showing the outline configuration of a monocular capsule endoscope 60 in the fourth modification with a weight balance in which the front-end side is relatively heavier. FIG. 20 shows a configuration example in which heavy components such as the permanent magnet 35 are arranged on the front-end side and the space 31 is arranged on the back-end side.

Moreover, as described in examples of the monocular capsule endoscopes 4, 60 capable of imaging only in the front-end direction, a monocular capsule endoscope in the second embodiment may be capable of imaging, in addition to the front-end direction only, for example, only in a perspective direction on the front-end side or a circumferential direction on the front-end side. Further, the capsule endoscope is not limited to the monocular one and may be a binocular capsule endoscope capable of imaging both in the front-end direction and the back-end direction. Posture control by the external permanent magnet 13 of a binocular capsule endoscope can also be made stable by changing the balance of the center of gravity in the front-back direction to decenter the center of gravity so that the binocular capsule endoscope floats at the interfacial boundary 12 always in a standing position, allowing stable imaging. Imaging in this case may be in both front and back directions or in one desired direction.

Fifth Modification

In the second embodiment, the floating position and floating posture of the capsule endoscope 4 are controlled by causing the external permanent magnet 13 to be successively allocated to positions on the body surface of the subject 2 desired empirically by physicians, but convenience may be increased by using an indication plate. FIG. 21 is a perspective view schematically exemplifying usage of an indication plate in a fifth modification. For example, a freely bendable indication plate 70 allocated around the waist of the subject 2 has a plurality of allocation markers 71 in regions where the external permanent magnet 13 should be allocated on the body surface based on a spatial relationship to the stomach 3 inside the subject 2 provided thereon.

Using the indication plate 70, the inner wall of the stomach 3 can thoroughly be observed without omission only by successively changing the position where the external permanent magnet 13 should be allocated following the positions of the allocation markers 71. Accordingly, an allocation operation of the external permanent magnet 13 is made easier and, in addition to physicians, it becomes possible for medical workers such as nurses to perform the allocation operation of the external permanent magnet 13, causing actual working hours of physicians to reduce and efficiency of examination to improve. If the indication plate 70 includes the allocation marker 71 for causing the external permanent magnet 13 to guide the capsule endoscope 4 after an examination to the pyloric part of stomach 3b, a guiding operation for excretion will also become easier.

In this case, it is preferable to provide a plurality of the indication plates 70 fitting to the physique of the subject 2 so that the indication plate 70 fitting to the physique can selectively be used. The form of the indication plate 70 is not limited to the sheet form and may be a dress type or frame mold mounted around the body surface of the subject 2 or a projection type projected onto the body surface of the subject 2.

Figure 22A:
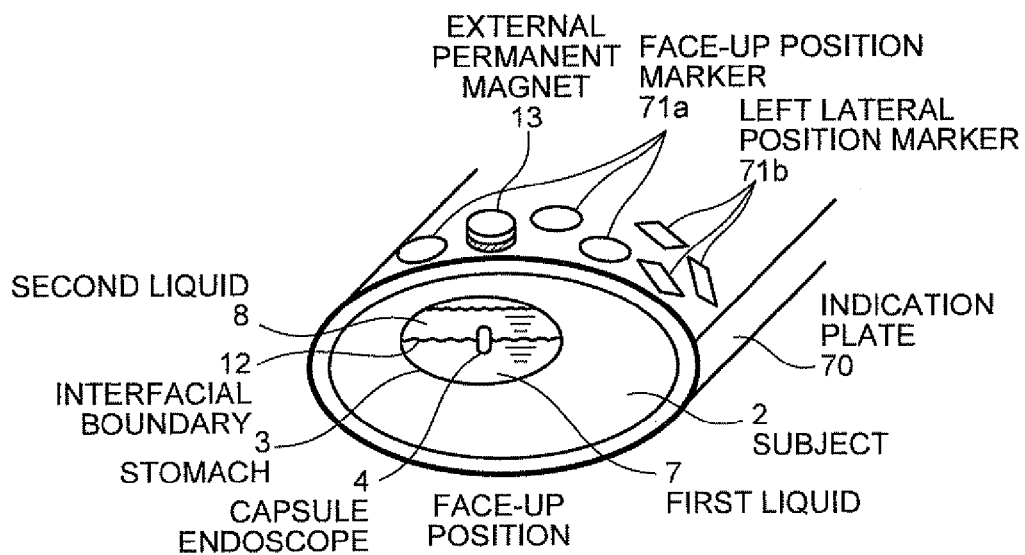
FIG. 22A is a perspective view schematically exemplifying an indication plate having allocation markers made different for each posture of a subject.
Figure 22B:
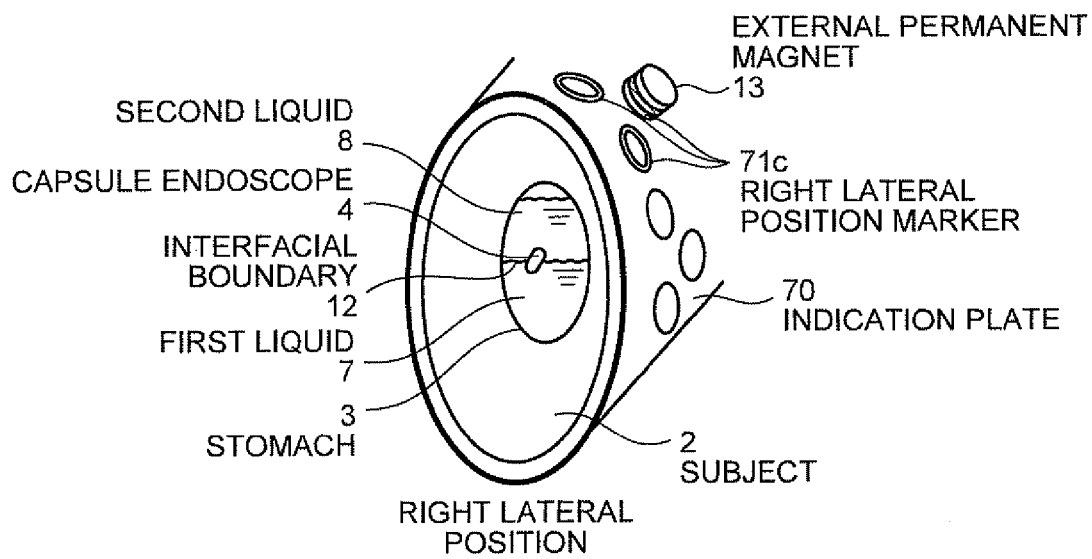
FIG. 22B is a perspective view schematically exemplifying the indication plate having allocation markers made different for each posture of the subject.

Since the most suitable allocation position of the external permanent magnet 13 is different for each posture of the subject 2, the allocation marker 71 of the indication plate 70 preferably use markers made different for each posture of the subject 2. FIG. 22A and FIG. 22B are perspective views schematically exemplifying the indication plate 70 having allocation markers made different for each posture of the subject 2. That is, in FIG. 22A and FIG. 22B, different allocation markers 71a, 71b, and 71c in circular, rhombic, and double circular shapes for face-up, left lateral, and right lateral positions respectively are provided and, when the posture in the face-up position is taken, as shown in FIG. 22A, the external permanent magnets 13 should successively be allocated following the allocation markers 71a for the face-up position and, when the posture in the right lateral position is taken, as shown in FIG. 22B, the external permanent magnets 13 should successively be allocated following the allocation markers 71c for the right lateral position. Accordingly, a movement operation of the external permanent magnets 13 in accordance with the posture is made clear and the operation can be made accurate and simple.

Further, if the plurality of types of the external permanent magnets 13 having different magnetic field strengths is provided, as described above, the different allocation markers 71 in accordance with the magnetic field strength most suitable for the external permanent magnet 13 to be allocated may be provided. The distance from the body surface of the subject 2 to the capsule endoscope 4 changes, depending on the position of each of the allocation markers 71. In this case, it is necessary to change the external permanent magnet 13 to be used to one having a different magnetic field strength in accordance with the distance and, by providing the different allocation markers 71 in accordance with the magnetic field strength most suitable for the external permanent magnet 13 to be allocated, it is necessary only to allocate the external permanent magnet 13 of the magnetic field strength according to the allocation marker 71 so that accurate and efficient examinations can be made.

Sixth Modification

Figure 24:
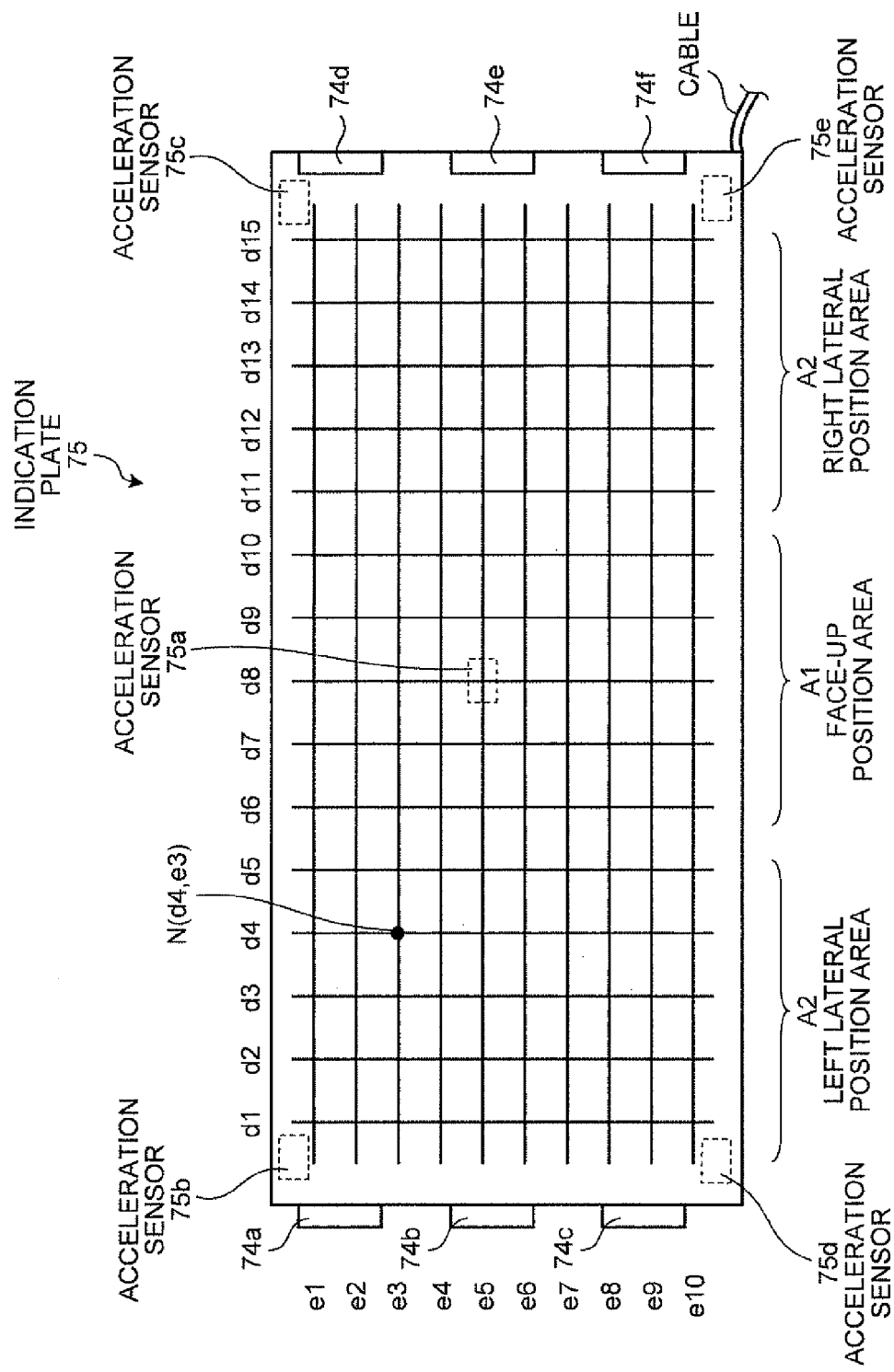
FIG. 24 is a plan view exemplifying the configuration of an indication plate used for magnified observation by expanding the indication plate.

A sixth modification enables magnified observation of a region of interest for realtime observation by using an indication plate. FIG. 23 is a schematic diagram showing the overall configuration of an intra-subject observation system having a magnified observation function for real-time observation, and FIG. 24 is a plan view exemplifying the configuration of an indication plate used for magnified observation by expanding the indication plate. As shown in FIG. 24r an indication plate 75 has a rectangular shape freely wearable by winding around the waist of the subject 2 and has connectors 74a to 74f like a surface fastener to connect both ends when the indication plate 75 is wound around the waist. The indication plate 75 also has grid-like coordinates marked thereon indicating allocation positions where, for example, the external permanent magnet 13 or attracting permanent magnets having a strong magnetic force for magnified observation should be allocated and here has 150 allocation coordinates indicated by horizontal axes d1 to d15 and vertical axes e1 to e10. Point N shown in FIG. 24, for example, indicates a point represented by coordinates (d4, e3). Among these coordinate points, the horizontal axes d1 to d5 are assigned to a left lateral position area A2, the horizontal axes d0 to d10 are assigned to a face-up position area A1, and the horizontal axes d11 to d15 are assigned to a right lateral position area A3.

A plurality of acceleration sensors, here five acceleration sensors 75a to 75e, for detecting the position of each portion of the indication plate 75 in relation to the acceleration sensor 25 contained in the capsule endoscope 4 is embedded in the indication plate 75. The acceleration sensor 75a is used to detect the reference position for the indication plate 75 and is allocated to coordinates (d8, e5) near the center of the indication plate 75 with the remaining four acceleration sensors 75b to 75e allocated near four corners. Incidentally, one of the acceleration sensors 75b to 75e allocated near four corners may also be selected to detect the reference position.

The spatial relationship between the indication plate 75 and the capsule endoscope 4 is set by putting the capsule endoscope 4 at the acceleration sensor 75a position on the indication plate 75 to activate the capsule endoscope 4 and initializing the acceleration sensor 25 and the acceleration sensors 75a to 75e before the capsule endoscope 4 being swallowed and the indication plate 75 being mounted. Accordingly, after the capsule endoscope 4 being swallowed and the indication plate 75 being mounted, the position of the capsule endoscope 4 and that of the indication plate 75 with respect to the capsule endoscope 4 including a bending state can always be grasped based on detection output of the acceleration sensors 25 and 75a to 75e.

Here, a position detection method by means of the acceleration sensors 25 and 75a to 75e will be described. The position (movement magnitudes) of the capsule endoscope 4 (capsule casing 21) in predetermined space coordinates xyz can be calculated by performing predetermined integration processing for an acceleration detected by the acceleration sensor 25. The calculated movement magnitudes are vector quantities indicating a movement distance and a movement direction of the capsule casing 21 in the space coordinates xyz. The posture of the capsule casing 21 is detected by performing predetermined integration processing for an angular velocity detected by the angular velocity sensor 26 and calculating a rotation angle of the major axis (longitudinal direction in the casing center) in the predetermined space coordinates xyz and that of the diameter axis (direction perpendicular to the major axis). Similarly, the position (movement magnitudes) of each of the acceleration sensors 75a to 75e in the predetermined space coordinates xyz can be calculated by performing predetermined integration processing for each acceleration detected by the acceleration sensors 75a to 75e respectively. The calculated movement magnitudes are each vector quantities indicating a movement distance and a movement direction of the indication plate 75 at the allocation position of each of the acceleration sensors 75a to 75e in the space coordinates xyz.

Figure 25:
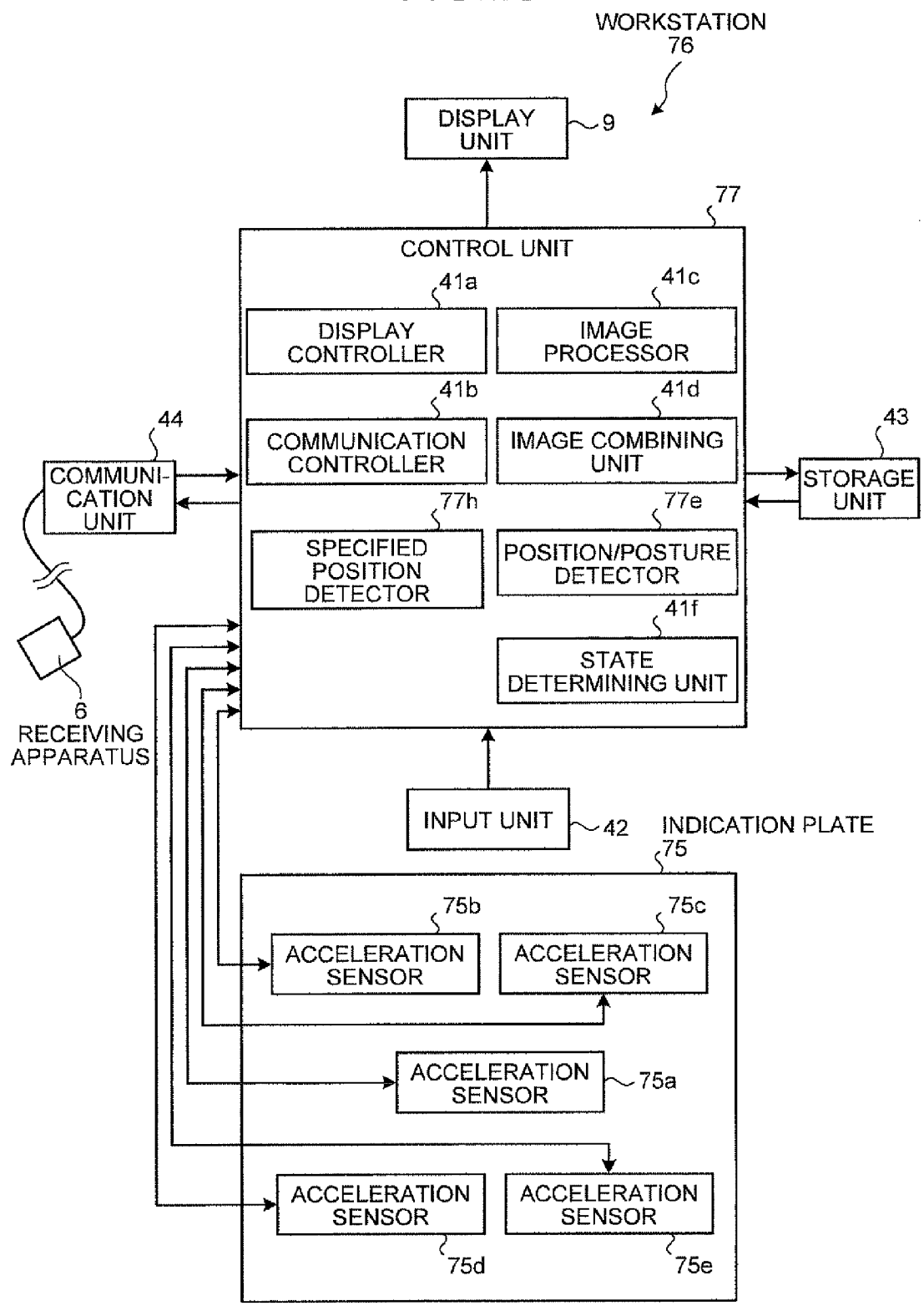
FIG. 25 is a schematic block diagram of a workstation shown by including an indication plate.

FIG. 25 is a schematic block diagram of a workstation 76 shown by including the indication plate 75. The indication plate 75 is connected to a control unit 77 of the workstation 76 via a cable so that position detection information of the acceleration sensors 75a to 75e can be captured. The control unit 77 has a position/posture detector 77e instead of the position/posture detector 41e in the configuration of the control unit 41 and also a newly added specified position detector 77h. The position/posture detector 77e detects, as described above, the floating position or floating posture of the capsule endoscope 4 based on detections results of the acceleration sensor 25 or angular velocity sensor 26 contained in the capsule endoscope 4 and also detects a relative spatial relationship with the capsule endoscope 4 relative to the acceleration sensor 75a, that is, the position of the indication plate 75 including a bending state based on detection results of the acceleration sensors 75a to 75e. The specified position detector 77h is used, when images picked up by the capsule endoscope 4 are observed in the display unit 9 in real time and a request of magnified observation is made through the display unit 9, to detect a coordinate position on the indication plate 75 corresponding to a specified position.

Figure 26:
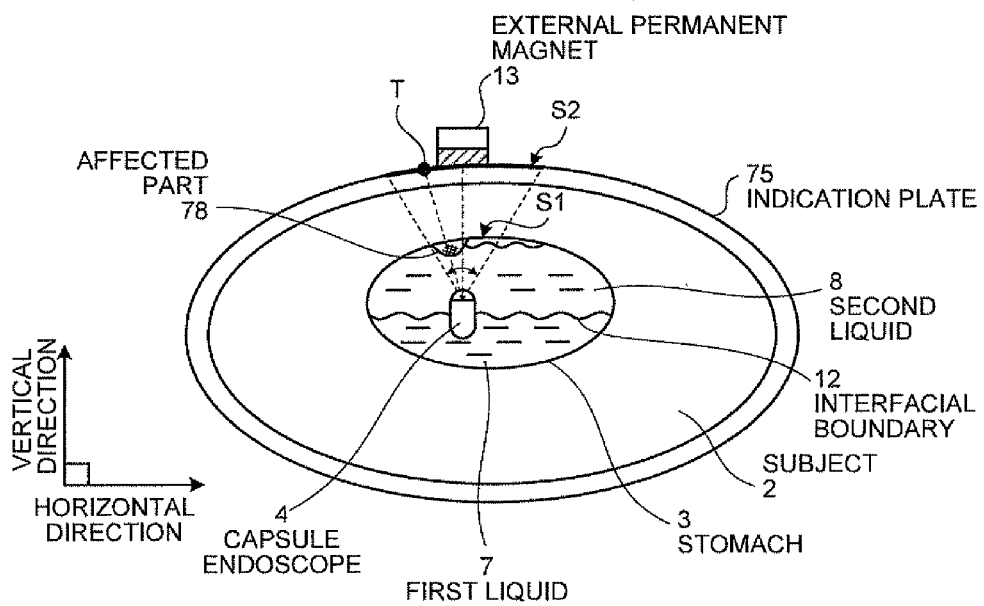
FIG. 26 is a schematic diagram exemplifying the appearance of imaging of a stomach 3 during real-time observation.

Next, a real-time observation inside the stomach 3 by the capsule endoscope 4 when the external permanent magnets 13 are allocated to appropriate positions outside the subject 2 following the indication plate 75 will be described. FIG. 26 is a schematic diagram exemplifying the appearance of imaging of the stomach 3 during real-time observation. The capsule endoscope 4 images a portion inside the stomach 3 in accordance with the imaging field of view thereof while drive control of the floating position or floating posture being performed by the external permanent magnets 13 and transmits images to the workstation 76 via the receiving apparatus 6, enabling real-time observation through the display unit 9.

Figure 27:
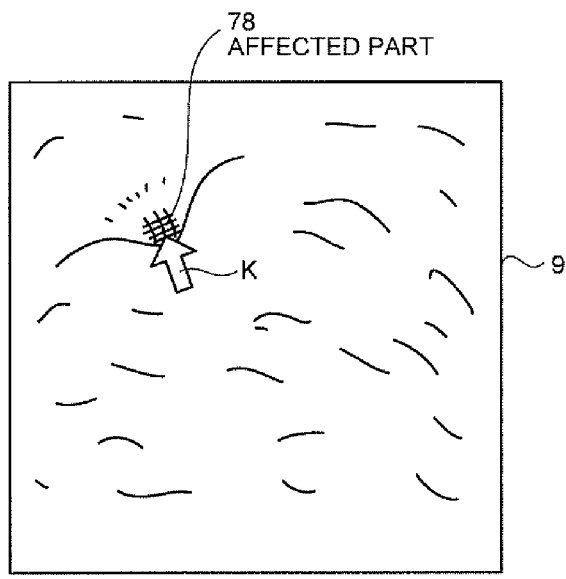
FIG. 27 is an explanatory diagram exemplifying a picked-up image displayed in a display unit.

Here, even if the distance between the capsule endoscope 4 and the inner wall of the stomach 3 is unknown, an imaged region S1 (picked-up image) concerning the inner wall of the stomach 3 by the capsule endoscope 4 can be represented as an imaged region S2 by projecting onto the indication plate 75. Under these circumstances, a case in which, as shown in FIG. 27, an affected part 78 of interest appears in a real-time image displayed in the display unit 9 after being imaged by the capsule endoscope 4 is considered. Thus, when a physician who is making a real-time observation uses a cursor K to specify the affected part 78 of interest by clicking to make a magnified observation of the affected part 78, the specified position detector 77h detects a coordinate position on the indication plate 75 corresponding to the affected part 78.

Figure 28:
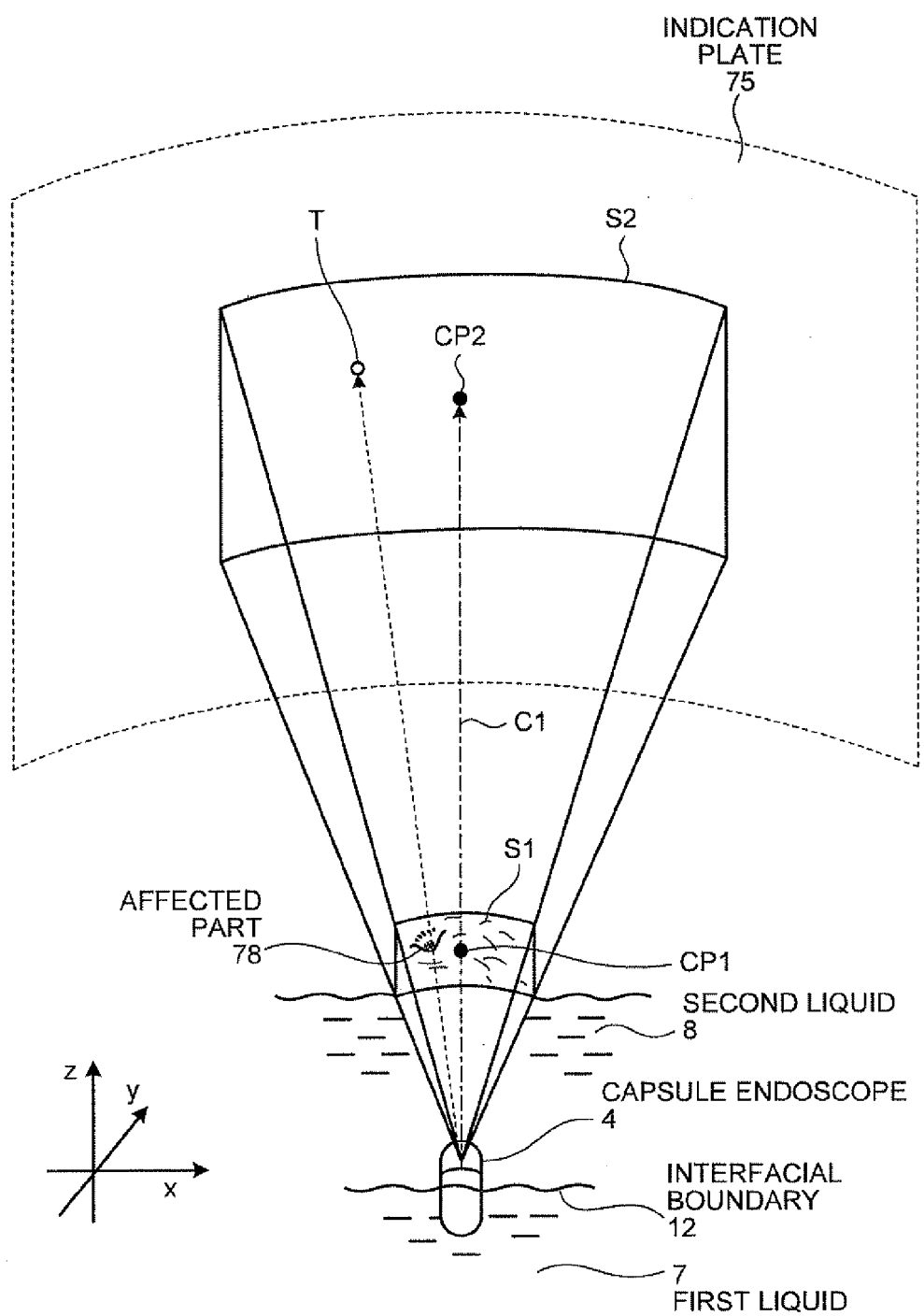
FIG. 28 is a schematic diagram showing a correspondence between an imaged region S1 (picked-up image) and an imaged region S2.

A detection operation of the coordinate position will be described with reference to FIG. 28. FIG. 28 is a schematic diagram showing a correspondence between the imaged region S1 (picked-up image) and the imaged region S2. A central point CP1 on the actual imaged region S1 (picked-up image) imaged by the capsule endoscope 4 can be represented as a central point CP2 on the extension of a center line C1 in the imaged region S2 on the indication plate 75. Similarly, the position of the specified affected part 78 on the actual imaged region S1 (picked-up image) can be represented as a specified position T in the imaged region S2 on the indication plate 75 following a projection line from the capsule endoscope 4. Here, a relative spatial relationship between the capsule endoscope 4 and each coordinate of the indication plate 75 is always grasped by the position/posture detector 77e based on detection results of the acceleration sensors 25 and 75a to 75e and thus, the specified position detector 77h can determines the specified position T on the indication plate 75 corresponding to the specified affected part 78. Coordinates of the determined specified position T are displayed, for example, in the display unit 9.

Figure 29:
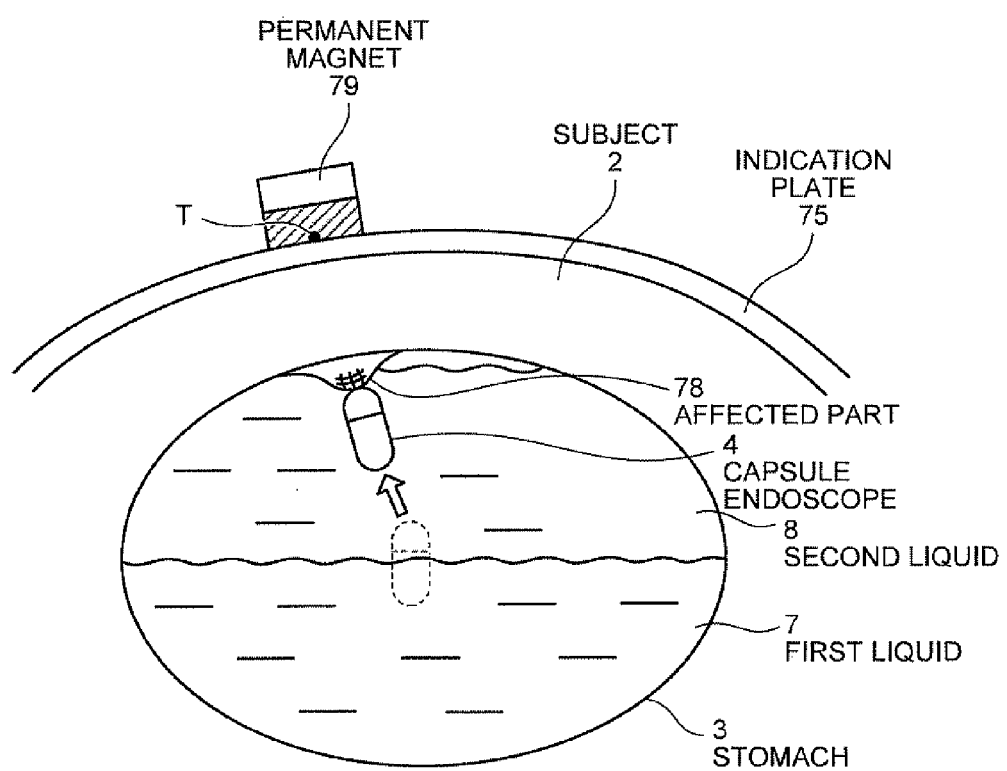
FIG. 29 is a schematic diagram showing the appearance during magnified observation.

Thus, if the physician who is making an observation allocates an attracting permanent magnet 79 having a strong magnetic force to the specified position T on the indication plate 75, as shown in FIG. 29, the capsule endoscope 4 floating at the interfacial boundary 12 is strongly attracted so that the capsule endoscope 4 comes into contact with the affected part 78. Accordingly, the affected part 78 is positioned in the center of an image picked up in close contact by the capsule endoscope 4 so that a magnified observation of the affected part 78 of interest can be made. A more detailed observation can thereby be made, leading to improved examination accuracy. Since, in addition to the first liquid 7, the second liquid 8 is inserted into the stomach 3, the capsule endoscope 4 moves from the interfacial boundary 12 toward the affected part 78 while floating in the second liquid 8 instead of the air and thus, an operation to come into close contact with the affected part 78 goes smoothly.

Incidentally, the specified position on the indication plate 75 corresponding to a magnified observation portion specified by the cursor K or the like may be caused to indicate directly through emission by causing a phosphor such as LED and organic EL to be directly buried at each coordinate position of the indication plate 75.

When the magnified observation function like in the six modification is added, a special light observation function may be provided in addition to the imaging/observation function by the LED 28 to the capsule endoscope 4 so that a detailed observation of the affected part 78 in close contact can be made. Observation lights in this case may be switched according to instructions from outside the subject 2. A tissue or body fluid collection function may be added to the capsule endoscope 4 to cause the collection function to collect a tissue or body fluid according to instructions from outside the subject 2 so that a detailed examination of the affected part 78 can be made. Further, a treatment function may be added to the capsule endoscope 4. The treatment function in this case is a function, for example, to cauterize an affected part 78 tissue by a heating probe or to cause a drug to act on the affected part 78 by a drug dissemination mechanism or drug injection function, and is performed according to instructions from outside the subject 2. Or, a chemical or biochemical sensor for diagnosis may be provided in the capsule endoscope 4 to cause the sensor to find whether the affected part 78 in close contact is a lesion.

Seventh Modification

Figure 30A:
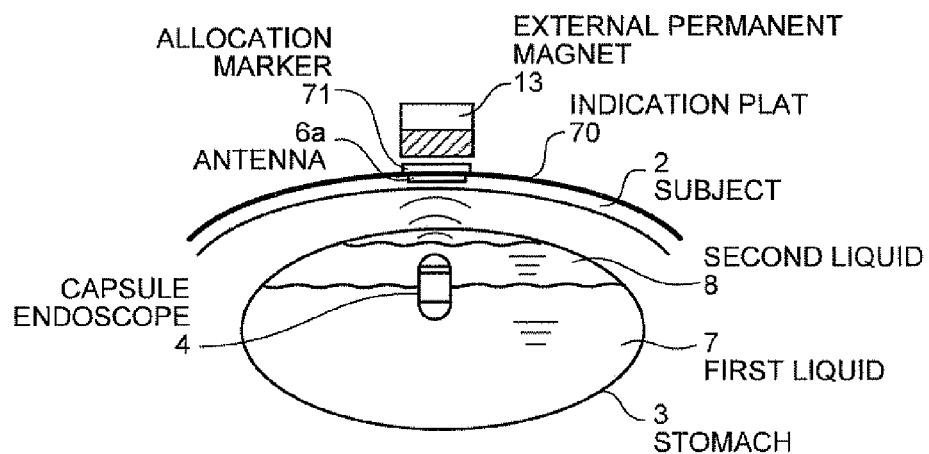
FIG. 30A is a sectional view schematically exemplifying usage of an indication plate having an antenna in a seventh modification.
Figure 30B:
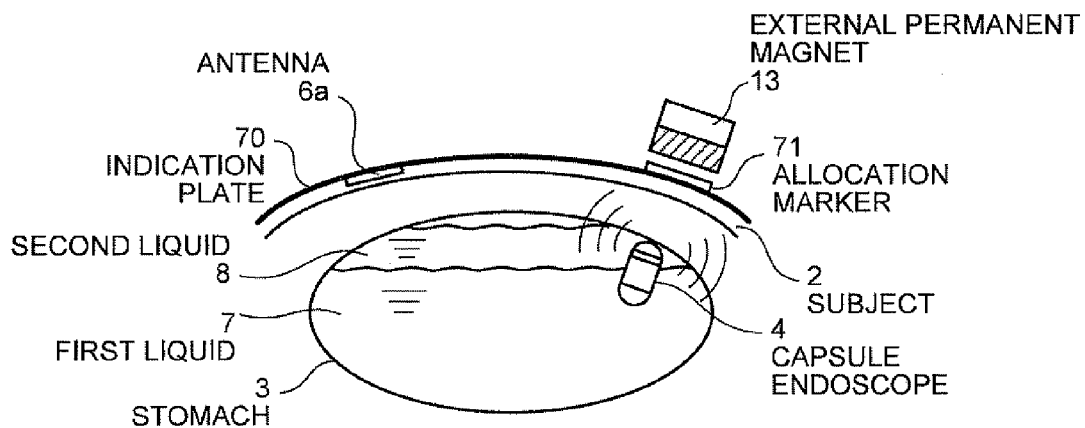
FIG. 30B is a sectional view schematically exemplifying usage of the indication plate having the antenna in the seventh modification.

In a seventh modification, the antenna 6a for receiving data transmitted from the capsule endoscope 4 by radio is provided at a predetermined position of the indication plate 70 for magnet allocation by associating with the position of the allocation marker 71 in consideration of communication conditions such as directivity of a transmitting antenna in the capsule endoscope 4. FIG. 30A and FIG. 30B are each sectional views schematically exemplifying usage of the indication plate 70 having the antenna 6a. FIG. 30A shows, for example, a configuration example in which the transmitting antenna of the capsule endoscope 4 has directivity in the longitudinal direction and the antenna 6a is allocated to the same position as the allocation marker 71. On the other hand FIG. 30B shows, for example, a configuration example in which the transmitting antenna of the capsule endoscope 4 has directivity in a direction perpendicular to the longitudinal direction and the antenna 6a is allocated to a position of the indication plate 70 in a direction perpendicular to the capsule endoscope 4 at the floating position that can be taken by the capsule endoscope 4 when the external permanent magnet 13 is allocated to the position of the allocation marker 71.

According to what is described above, the antenna 6a has an optimal receiving state when the capsule endoscope 4 is positioned where images are picked up so that data can be received at a low level of noise, improving observability. Moreover, mounting of the antenna 6a is complete only by mounting the indication plate 70 on the body surface of the subject 2 and thus, examination efficiency is improved.

Eighth Modification

The acceleration sensor 25 or the angular velocity sensor 26 contained in the capsule endoscope 4 is used in the second embodiment to detect the floating position or floating posture of the capsule endoscope 4, but a contained distance sensor may also be used. That is, an optical or supersonic distance sensor may be provided in the capsule endoscope 4 to detect the distance to the inner wall of stomach and correct differences in size caused by the distance among a plurality of images based on the detected distance information before images are combined.

Figure 31A:
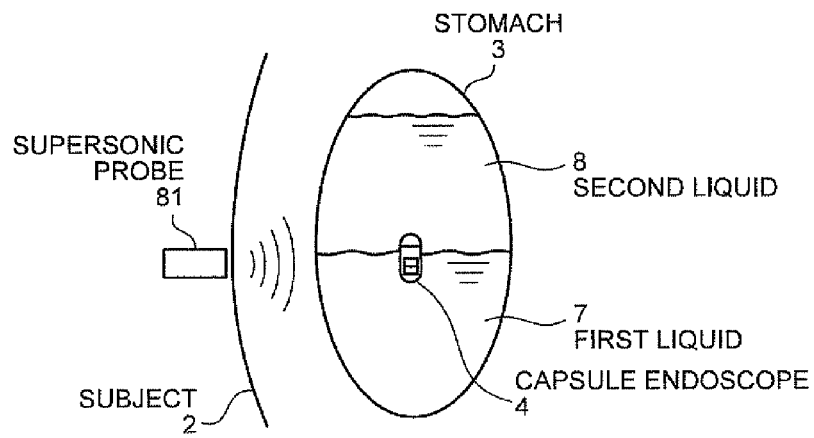
FIG. 31A is a schematic diagram exemplifying the configuration of a supersonic position detector in an eighth modification.
Figure 31B:
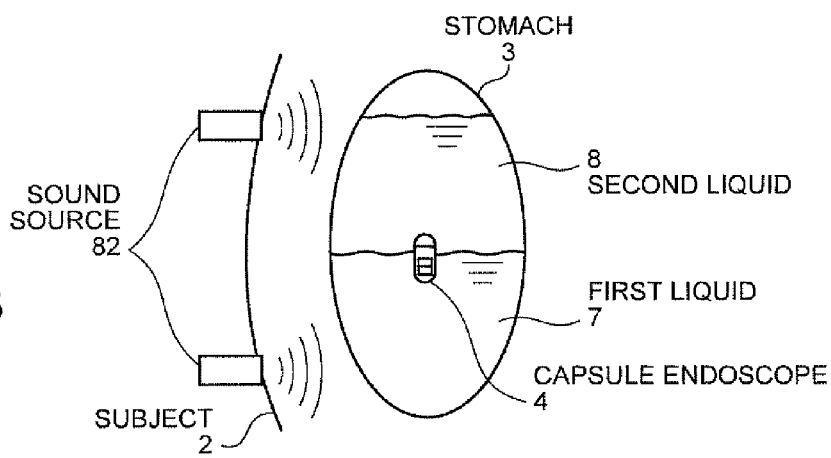
FIG. 31B is a schematic diagram exemplifying the configuration of an acoustic position detector in the eighth modification.
Figure 31C:
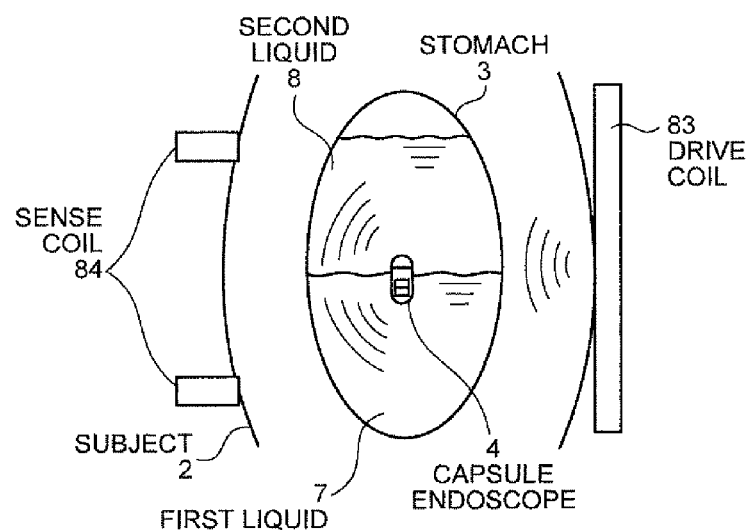
FIG. 31C is a schematic diagram exemplifying the configuration of a magnetic position detector in the eighth modification.

The detector to detect the floating position or floating posture of the capsule endoscope 4 is not limited to one contained in the capsule endoscope 4 and may be provided outside the subject 2. FIG. 31A to FIG. 31C are each schematic diagrams exemplifying the configuration of a position detector of the capsule endoscope 4 provided outside the subject 2. FIG. 31A shows an example of a supersonic method for detecting the position of the capsule endoscope 4 using detection of a tomogram by a supersonic probe 81. Since the stomach 3 is filled with the first liquid 7 and the second liquid 8, supersonic waves generated by the supersonic probe 81 are more likely to propagate so that the position of the capsule endoscope 4 can be detected inside the stomach 3 from a tomogram. The distance between the wall of stomach and the capsule endoscope 4 is known with the use of supersonic waves, which is useful information for combining a plurality of images.

FIG. 31B shows an example of an acoustic method in which a small microphone is mounted in the capsule endoscope 4 and sound sources 82 are arranged at a plurality of positions outside the subject 2. The position of the capsule endoscope 4 can be detected by calculating distances from the sound sources 82 at the plurality of positions based on strength of sound detected by the small microphone contained in the capsule endoscope 4.

FIG. 31C shows an example of a magnetic method in which an induction coil is contained in the capsule endoscope 4, a magnetic field from a drive coil 83 outside the subject 2 is acted on the induction coil to generate an induction field by a resonance system of the induction coil and a capacitor inside the capsule endoscope 4, and strength of the induction field is detected by sense coils 84 outside the subject 2 to detect the position of the capsule endoscope 4. The capsule endoscope 4 generates an induction field induced by a magnetic field from the drive coil 83 outside the subject 2 and does not use the battery inside the capsule endoscope 4, contributing to energy savings. Besides, a magnetic field generator may be provided in the capsule endoscope 4 together with a magnetic field detector provided outside the subject 2. According to this configuration, a magnetic field detector such as an MI device can be allocated outside the subject 2 and thus, a large high-sensitivity detector can be used. Or, conversely, a magnetic field may be generated outside the subject 2, which is to be detected by the capsule endoscope 4. According to this configuration, energy consumption by the capsule endoscope 4 can be reduced compared with the configuration in which a magnetic field generator is provided in the capsule endoscope 4. Moreover, detection results of these positions or postures may be used to determine the position of images picked up by the capsule endoscope 4 or to combine images.

Third Embodiment

Figure 32:
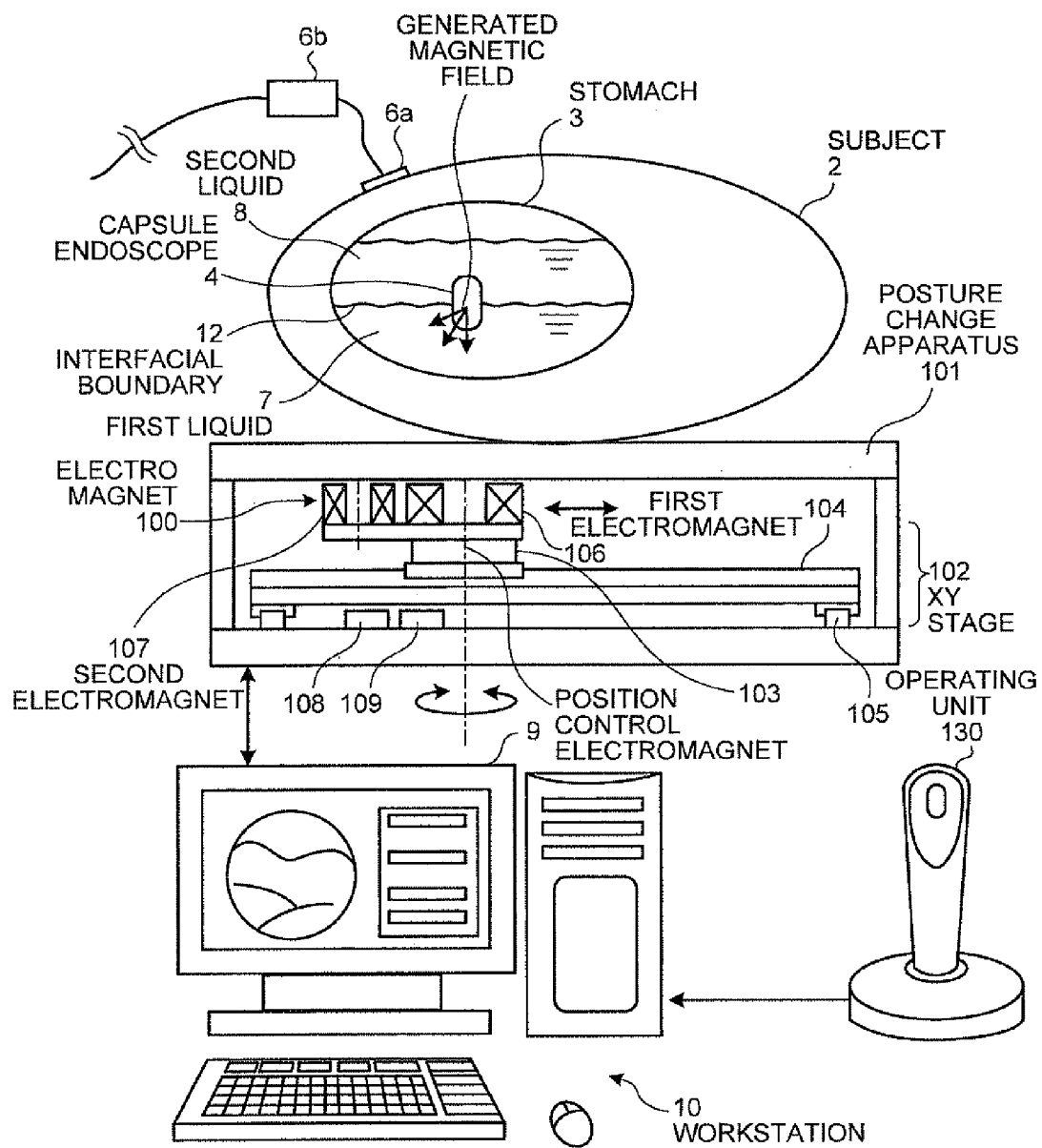
FIG. 32 is a schematic diagram showing the overall configuration of an intra-subject observation system in a third embodiment of the present invention.

Next, a third embodiment of the present invention will be described with reference to FIG. 32. The same reference numerals are attached to the same components as those shown in FIG. 14 to FIG. 31 and a description thereof will not be repeated here. FIG. 32 is a schematic diagram showing the overall configuration of an intra-subject observation system in the third embodiment of the present invention. The intra-subject observation system in the third embodiment comprises, instead of the external permanent magnet 13 shown in FIG. 14, an electromagnet 100 as a magnetic field applicator outside the subject 2. The electromagnet 100 is mounted on an XY stage 102 provided inside a posture change apparatus 11 via a rotation table 103. The XY stage 102 comprises a rail 104 freely slidably supporting the rotation table 103 in the X direction and rollers 105 freely movably supporting the rail 104 in the Y direction. Accordingly, the allocation position of the electromagnet 100 supported by the XY stage 102 is freely changeable in an XY plane with respect to the subject 2 on the posture change apparatus 11.

Here, the electromagnet 100 comprises a first electromagnet 106 and a second electromagnet 107. The first electromagnet 106 is used to apply a stronger external magnetic field in the up-and-down direction to the permanent magnet 35 inside the capsule endoscope 4 to control the floating position of the capsule endoscope 4 floating at the interfacial boundary 12 inside the stomach 3 and is mounted on the rotation center of the rotation table 103. The second electromagnet 107 is used to apply a external magnetic field in the up-and-down direction to the permanent magnet 35 inside the capsule endoscope 4 to control the floating posture (orientation) of the capsule endoscope 4 floating at the interfacial boundary 12 inside the stomach 3. Thus, the external magnetic field applied by the second electromagnet 107 is set weaker than that applied by the first electromagnet 106. The second electromagnet 107 is allocated on the rotation table 103 next to the first electromagnet 106 and is allocatable to any position around the first electromagnet 106 with rotation of the rotation table 103.

The posture change apparatus 11 also comprises drive power supplies 108 and 109 for passing a drive current to the first electromagnet 106 and the second electromagnet 107 respectively. The control unit 41 in the workstation 10 comprises an energization controller to change the floating position or floating posture of the capsule endoscope 4 by selectively controlling passing of the drive current to the first electromagnet 106 and the second electromagnet 107 from the drive power supplies 108 and 109. The workstation 10 also comprises an operating unit 130 for controlling the rotation position of the rotation table 103 and controlling the position of the rotation table 103 on the stage 102 two-dimensionally on the XY plane.

Next, an operation of the electromagnet 100 in the third embodiment will be described. As described above, the capsule endoscope 4 images the inner wall of the stomach 3 while floating at the interfacial boundary 12 between the first liquid 7 and the second liquid 8 inside the stomach 3. Here, if a predetermined external magnetic field to be a direction of attraction is applied in the up-and-down direction from outside the subject 2 to the permanent magnet 35 inside the capsule endoscope 4 by the first electromagnet 106 by driving the drive power supply 108 only, a magnetic force of attraction in the vertical direction acts and the capsule endoscope 4 is held in a standing position at the position of the interfacial boundary 12. Then, if the operating unit 130 is operated to suitably move the XY stage 102 in the XY direction, the position of the rotation table 103 is also thereby moved in the XY plane so that the position of the endoscope 4 held in the standing position by the magnetic force of attraction generated by the first electromagnet 106 can be forced to move at the interfacial boundary 12. Thus, the imaging position inside the stomach 3 by the capsule endoscope 4 can be changed by arbitrarily and forcibly displacing the floating position of the endoscope 4 at the interfacial boundary 12 by the first electromagnet 106.

Further, if a predetermined external magnetic field to be a direction of attraction in the up-and-down direction is applied laterally from outside the subject 2 to the permanent magnet 35 inside the capsule endoscope 4 by the second electromagnet 107 by also driving the drive power supply 109 while the capsule endoscope 4 is held by the first electromagnet 106, as described above, the external magnetic field acts on the capsule endoscope 4 in an oblique direction or in the horizontal direction. Since, as a result, the external magnetic field for holding in the up-and-down direction by the first electromagnet 106 and that in the oblique direction (or the horizontal direction) by the second electromagnet 107 act on the capsule endoscope 4, as shown vectorially in FIG. 29, an external magnetic field in a combined direction of both external magnetic fields will act on the capsule endoscope 4, changing the floating posture of the capsule endoscope 4 from the standing position to an oblique position. The oblique direction in this case can arbitrarily be changed by changing the position of the second electromagnet 107 with respect to the first electromagnet 106, that is, by operating the operating unit 110 to rotate the rotation table 103 to change the position of the second electromagnet 107. The oblique angle of the capsule endoscope 4 can be caused to change by changing the amount of current passed to the second electromagnet 107 to cause the strength of an applied magnetic field to change. Thus, the imaging direction inside the stomach 3 by the capsule endoscope 4 can be changed by arbitrarily and forcibly displacing the floating posture of the endoscope 4 at the interfacial boundary 12 by the first electromagnet 106 and the second electromagnet 107.

Accordingly, the imaging position or imaging direction inside the stomach 3 by the capsule endoscope 4 can be changed by arbitrarily and forcibly displacing the floating position or floating posture of the endoscope 4 at the interfacial boundary 12 by the first electromagnet 106 or the second electromagnet 107 and therefore, observations inside the stomach 3 can be made exhaustively in a short time and an observation of a region desired by a physician or the like can easily be realized. The position control of the capsule endoscope 4 in the gravity direction in this case can easily be realized by gradually increasing the above-described amount of the first liquid 7 inserted into the stomach 3. Further, observations inside the stomach 3 can be made more thoroughly without omission by making observations while combining posture changes of the subject 2 described above and forcing the floating position or floating posture of the capsule endoscope 4 to be displaced for each desired posture.

If the polarity of external magnetic fields applied from the first electromagnet 106 or the second electromagnet 107 is switched from the direction of attraction to that of repulsion, the imaging direction of the capsule endoscope 4 is switched from the upward direction to the downward direction or from the downward direction to the upward direction.

Ninth Modification

Figure 33:
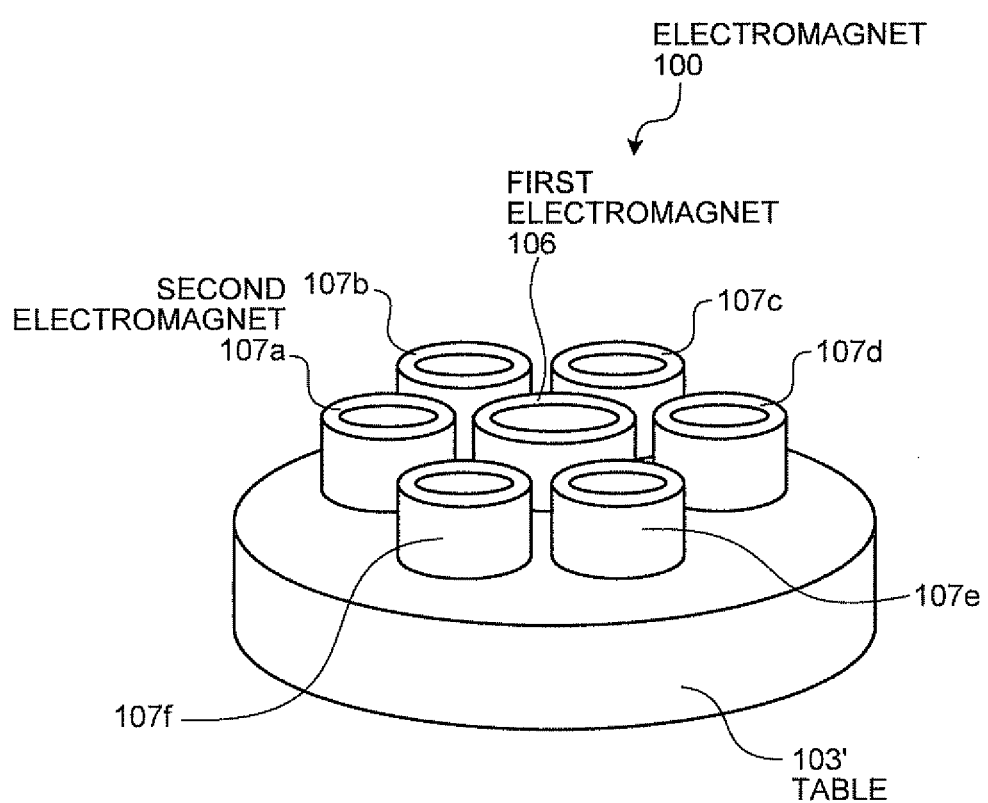
FIG. 33 is a perspective view exemplifying the configuration of an electromagnet in a ninth modification.

FIG. 33 is a perspective view exemplifying the configuration of the electromagnet 100 in a ninth modification. While only one second electromagnet 107 is provided in the third embodiment, a plurality of second electromagnets 107a to 107f is disposed around the first electromagnet 106 in the ninth modification to allow selective energization/driving. Reference numeral 103' is a table mounted on the XY stage 102. According to this configuration, there is no need to rotate the table 103' to change the floating posture of the capsule endoscope 4 and it is necessary only to select an electromagnet at a desired position from the second electromagnets 107a to 107f and to drive the selected electromagnet, allowing miniaturization/simplification of the structure of the XY stage 102.

Tenth Modification

Figure 34:
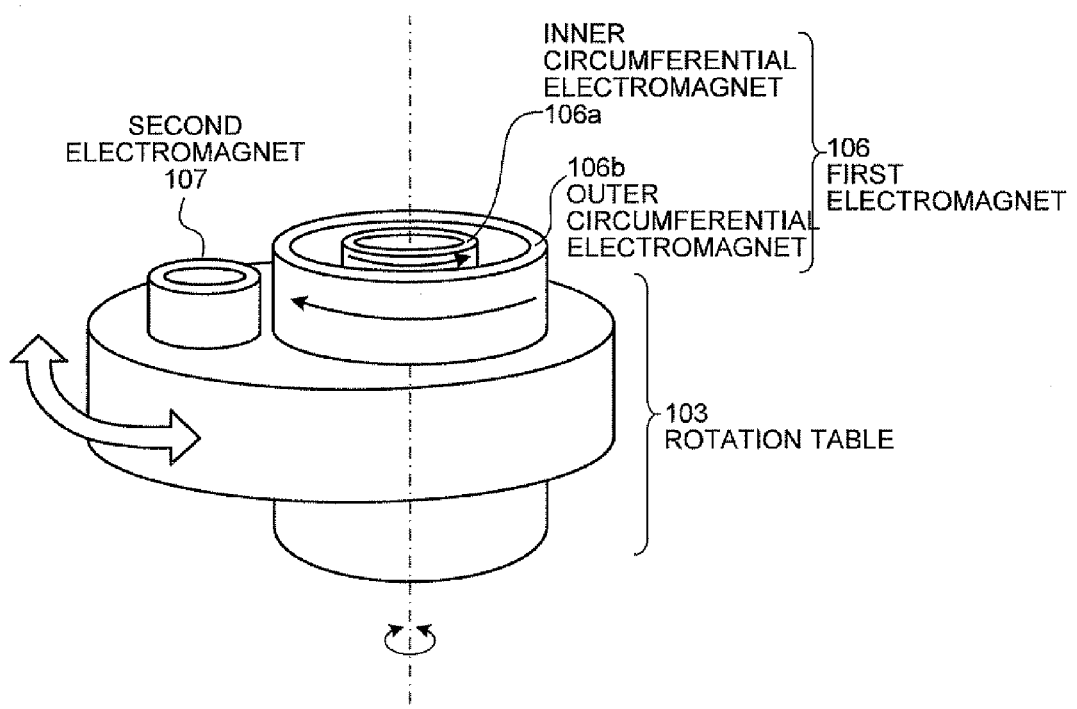
FIG. 34 is a perspective view exemplifying the configuration of an electromagnet in a tenth modification.

FIG. 34 is a perspective view exemplifying the configuration of the electromagnet 100 in a tenth modification. The first electromagnet 106 in the tenth modification has a double structure of an inner circumferential electromagnet 106a and an outer circumferential electromagnet 106b, and currents in opposite directions as shown by arrows are passed in the inner circumferential electromagnet 106a and the outer circumferential electromagnet 106b. By causing the outer circumferential electromagnet 106b to generate a magnetic field in a direction opposite to that of a magnetic field generated by the inner circumferential electromagnet 10a in the first electromagnet 106, the magnetic field gradient toward the central axis of the first electromagnet 106 can be increased. The capsule endoscope 4 is thereby made easier to trap by the first electromagnet 106, leading to improved controllability.

Eleventh Modification

Figure 35:
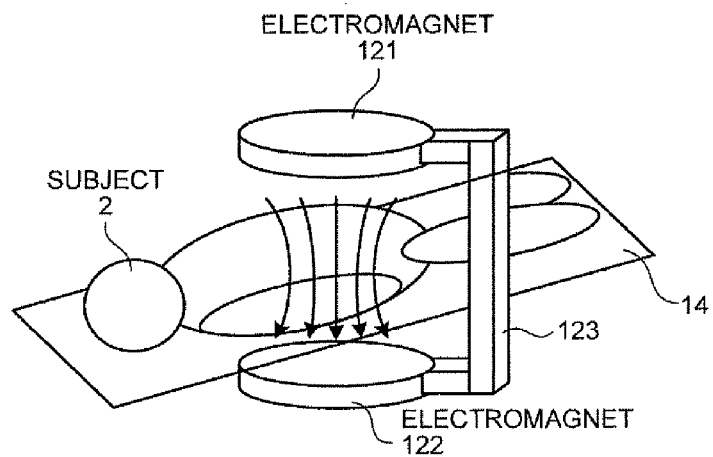
FIG. 35 is a schematic perspective view exemplifying the configuration in an eleventh modification.

FIG. 35 is a schematic perspective view exemplifying the configuration in an eleventh modification. While the first electromagnet 106 and the second electromagnet 107 are provided in the third embodiment, a pair of electromagnets 121, 122 arranged opposite to each other in the up-and-down direction outside the subject 2 is provided in the eleventh modification. Reference numeral 123 is a rotating column that freely changes the positions of the electromagnets 121, 122 with respect to the subject 2 by supporting the electromagnets 121, 122. According to this configuration, a stable external magnetic field can be provided in a wide range to the capsule endoscope 4 inside the stomach 3, leading to improved controllability.

Fourth Embodiment

Figure 36:
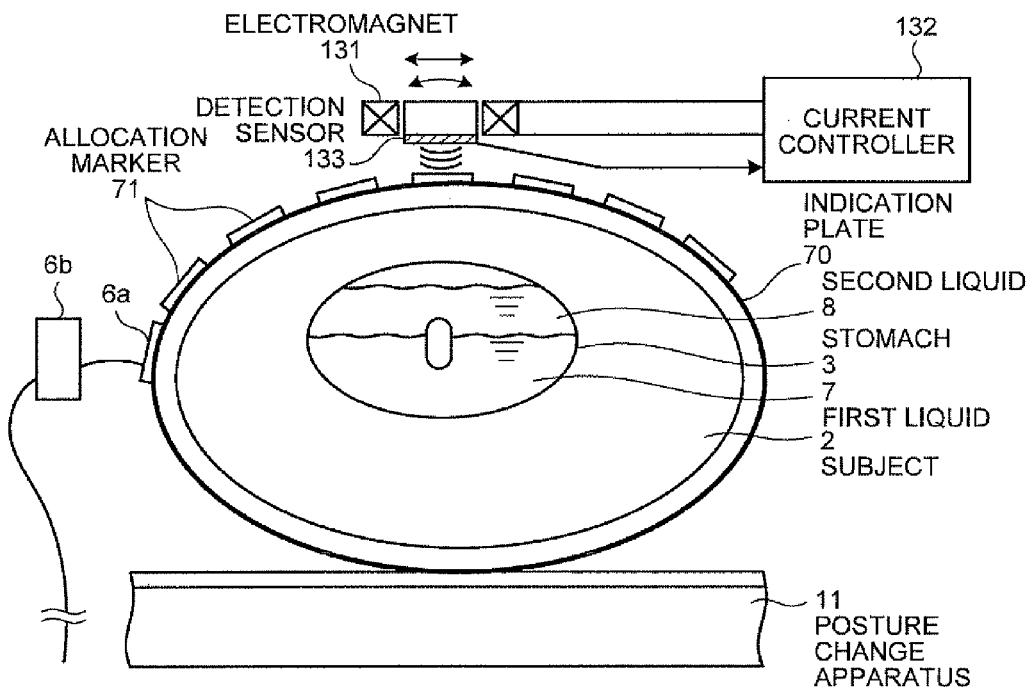
FIG. 36 is a schematic diagram showing the configuration of a portion of an intra-subject observation system in a fourth embodiment of the present invention.

Next, a fourth embodiment of the present invention will be described with reference to FIG. 36. The same reference numerals are attached to the same components as those shown in FIG. 14 to FIG. 31 and a description thereof will not be repeated here. FIG. 36 is a schematic view showing the configuration of a portion of an intra-subject observation system in the fourth embodiment. The intra-subject observation system in the fourth embodiment comprises, instead of the external permanent magnet 13 shown in FIG. 14, an electromagnet 131 whose allocation position outside the subject 2 is freely changeable with cantilevered suspension by an arm material as a magnetic field applicator. The strength of an external magnetic field of the electromagnet 131 applied to the capsule endoscope 4 is made freely changeable through control of the drive current by a current controller 132 provided with the control unit 41 in the workstation 10.

As described above, the capsule endoscope 4 images the inner wall of the stomach 3 while floating at the interfacial boundary 12 between the first liquid 7 and the second liquid 8 inside the stomach 3. Here, the fourth embodiment comprises the electromagnet 131 with cantilevered suspension by a medical worker outside the subject 2, which can apply an external magnetic field to the permanent magnet 35 inside the capsule endoscope 4. The permanent magnet 35 is magnetized in the longitudinal direction of the capsule endoscope 4 and, the floating position at the interfacial boundary 12 of the capsule endoscope 4 can be forced to be displaced in a horizontal plane by selecting polarity of an applied magnetic field of the electromagnet 131 and allocating the electromagnet 131 opposite to the permanent magnet 35, and then moving the allocation position of the electromagnet 131 in the horizontal plane while applying an external magnetic field in a direction of attraction. If the electromagnet 131 is displaced by rotation at the allocation position of the electromagnet 131, the direction of the external magnetic field applied to the permanent magnet 35 is also tilted from the vertical direction, thereby forcing the floating posture at the interfacial boundary 12 of the capsule endoscope 4 to be displaced in the horizontal plane.

Accordingly, the imaging position and imaging direction inside the stomach 3 by the capsule endoscope 4 can be changed by arbitrarily and forcibly displacing the floating position or floating posture of the capsule endoscope 4 at the interfacial boundary 12 by the electromagnet 131 and therefore, observations inside the stomach 3 can be made exhaustively in a short time and an observation of a region desired by a physician or the like can easily be realized. The position control of the capsule endoscope 4 in the gravity direction in this case can easily be realized by gradually increasing the above-described amount of the first liquid 7 inserted into the stomach 3. Further, observations inside the stomach 3 can be made more thoroughly without omission by making observations while combining posture changes of the subject 2 described above and forcing the floating position or floating posture of the capsule endoscope 4 to be displaced for each desired posture.

Here, the indication plate 70 with the allocation markers 71 is mounted on the body surface of the subject 2 in the fourth embodiment and thus, the position of the electromagnet 131 may be changed following the allocation markers 71. At this point, the distance from the body surface to the capsule endoscope 4 inside the stomach 3 is different depending on the position of each of the allocation markers 71 and thus, it is preferable to change the current to be passed to the electromagnet 131 depending on the type of the allocation marker 71 by providing the different allocation markers 71 in accordance with the magnetic field strength most suitable for the electromagnet 131 to be allocated. Change control of the current to be passed to the electromagnet 131 may automatically be performed by the current controller 132 based on a detection result of the type of the allocation marker 71 detected by a marker detection sensor 133 provided in the electromagnet 131. Or, change control of the current may automatically be performed by the current controller 132 based on, instead of the type of the allocation marker 71 being detected, position information of the electromagnet 131.

Fifth Embodiment

Figure 37:
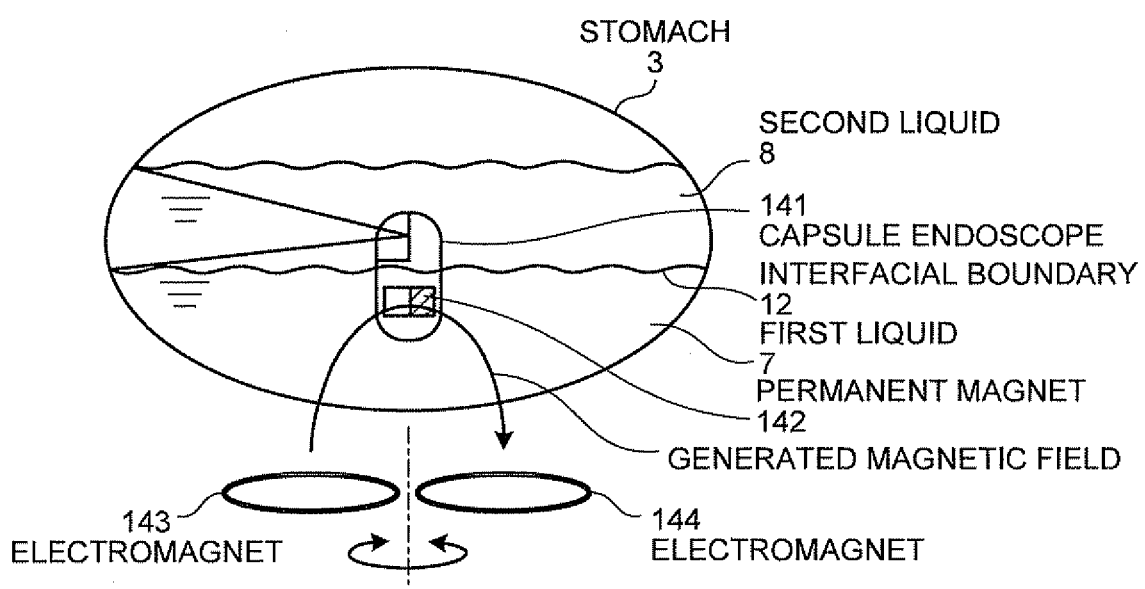
FIG. 37 is a schematic view showing the configuration of a portion of an intra-subject observation system in a fifth embodiment of the present invention.

Next, a fifth embodiment of the present invention will be described with reference to FIG. 37. The same reference numerals are attached to the same components as those shown in FIG. 14 to FIG. 31 and a description thereof will not be repeated here. FIG. 37 is a schematic diagram showing the configuration of a portion of an intra-subject observation system in the fifth embodiment. The intra-subject observation system in the fifth embodiment comprises, instead of the monocular capsule endoscope 4 capable of imaging in the front-end direction shown in FIG. 14 or the like, a monocular capsule endoscope 141 capable of imaging in a side-looking direction perpendicular to the longitudinal direction. The capsule endoscope 141 may be capable of imaging in the oblique direction only. The capsule endoscope 141 contains a permanent magnet 142 magnetized in such a way that N and S poles are in the diameter direction as a magnetic body and the center of gravity is arranged, for example, so as to make the back-end side heavier.

Also, outside the subject 2, a pair of electromagnets 143, 144 having the same properties and arranged adjacent to each other and on the same plane with respect to the center position on the lower side is provided as a magnetic field applicator. External magnetic fields generated by these electromagnets 143, 144 are set to be in the up-and-down direction. These electromagnets 143, 144 are provided freely rotatably around the central axis in a horizontal plane.

Here, the capsule endoscope 141 floats at the interfacial boundary 12 between the first liquid 7 and the second liquid 8 inside the stomach 3. At this point, the insertion amount of the second liquid 8 into the stomach 3 is adjusted so that the imaging field of view of the imaging optical system in the side-looking method is in the second liquid 8. Accordingly, the capsule endoscope 141 images the side surface of the inner wall of the stomach 3 while floating at the interfacial boundary 12. Here, if the electromagnets 143, 144 are rotated around the central axis in the horizontal plane while causing these electromagnets 143, 144 to apply an external magnetic field from the electromagnet 143 to the electromagnet 144 by passing through the permanent magnet 142, a rotating magnetic field will act on the permanent magnet 142 in the horizontal plane so that the posture of the capsule endoscope 141 changes as if to rotate like a lighthouse in the horizontal plane while maintaining the standing position. The capsule endoscope 141 in the side-looking method can thereby pick up images from all around the inner wall of the stomach 3 in the horizontal plane and make observations inside the stomach 3 exhaustively in a short time. The imaging position in the height direction can be controlled by adding the insertion amount of the first liquid 7.

Sixth Embodiment

Figure 38:
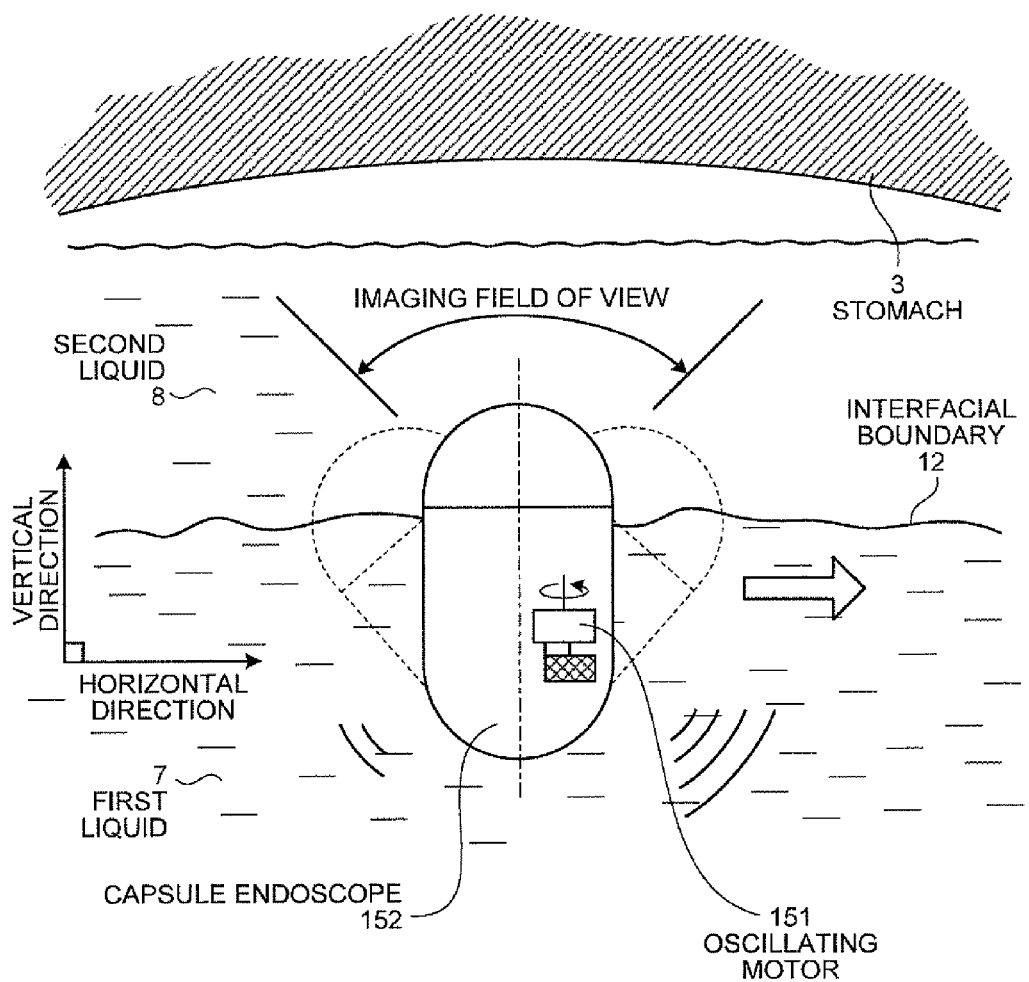
FIG. 38 is a schematic view showing the configuration of a portion of an intra-subject observation system in a sixth embodiment of the present invention.

Next, a sixth embodiment of the present invention will be described with reference to FIG. 38. The same reference numerals are attached to the same components as those shown in FIG. 14 to FIG. 31 and a description thereof will not be repeated here. FIG. 38 is a schematic diagram showing the configuration of a portion of an intra-subject observation system in the sixth embodiment. The intra-subject observation system in the sixth embodiment comprises, instead of the capsule endoscope 4 shown in FIG. 14 or the like, a capsule endoscope 152 containing an oscillating motor 151 like a pager motor as a self-oscillating mechanism. As shown in FIG. 38, the oscillating motor 151 arranged decentered from the central axis in the longitudinal direction of the capsule endoscope 152. The center of gravity of the capsule endoscope 152 is decentered toward the back-end side with the arrangement of the oscillating motor 151, a battery and the like, which are heavier among components in the capsule endoscope 152, on the back-end side.

The capsule endoscope 152 in the sixth embodiment images the inner wall of the stomach 3 while floating at the interfacial boundary 12 between the first liquid 7 and the second liquid 8 inside the stomach 3. Here, the capsule endoscope 152 in the sixth embodiment contains the decentered oscillating motor 151 and an oscillatory movement, indicated by dashed lines in FIG. 38, of the capsule endoscope 152 is generated by causing the oscillating motor 151 to generate an oscillatory movement. As a result, the capsule endoscope 152 moves by changing the floating position or floating posture at the interfacial boundary 12 while being forced to oscillate by itself. Accordingly, the capsule endoscope 152 can pick up images inside the stomach 3 in a wide range and make observations inside the stomach 3 exhaustively in a short time. The imaging position in the height direction can be controlled by adding the insertion amount of the first liquid 7. Further, by combining posture changes of the subject 2 described above, observations inside the stomach 3 can be made more thoroughly.

Incidentally, the oscillating motor 151 may be started to drive when the capsule endoscope 152 is swallowed, or after being swallowed into the stomach 3, the oscillating motor 151 may be started to drive by being switched on according to radio instructions from outside at an appropriate time.

Figure 39:
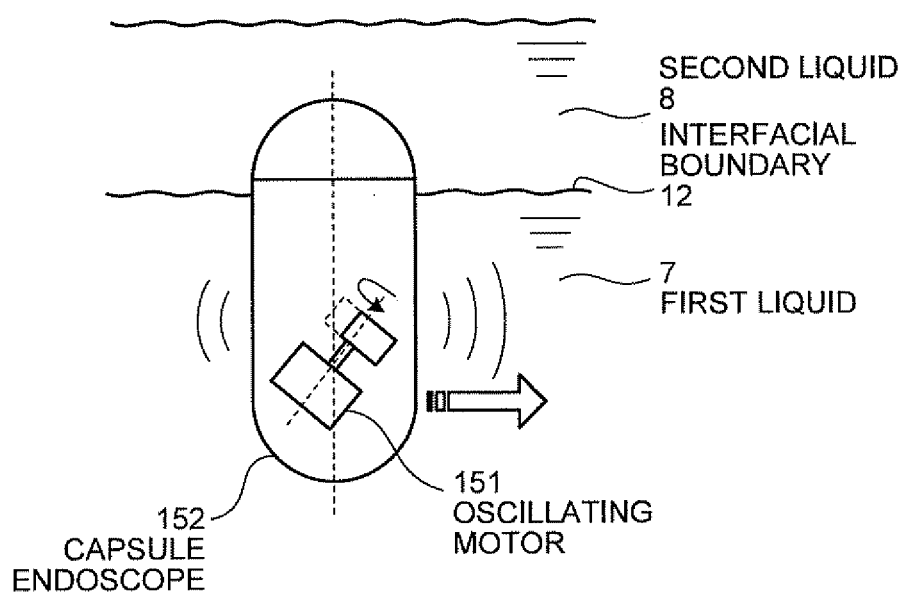
FIG. 39 is a schematic diagram exemplifying a modified arrangement of an oscillating motor.
Figure 40:
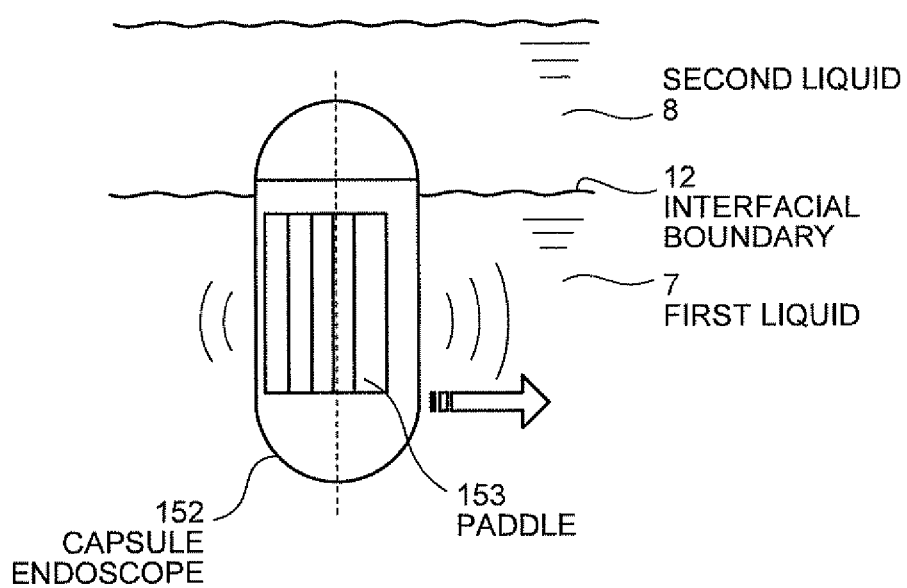
FIG. 40 is a schematic diagram exemplifying a modified configuration to which a paddle is added.
Figure 41:
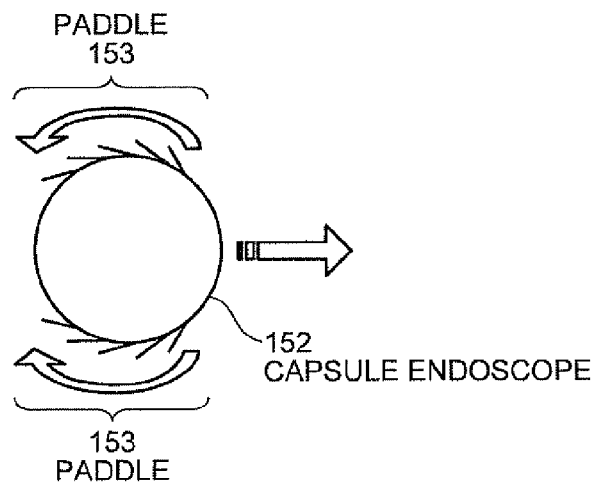
FIG. 41 is a plan view exemplifying the modified configuration to which the paddle is added.

As shown in FIG. 39, the oscillating motor 151 may be arranged slantingly to intersect the central axis in the longitudinal direction. Or, after causing the oscillating motor 151 to be arranged on the central axis in the longitudinal direction, as shown in FIG. 40 and FIG. 41, a fin-like paddle 153 may be provided on both sides on an outer circumference of the capsule endoscope 152 so that the capsule endoscope 152 moves in a horizontal plane by the first liquid 7 being paddled by the paddle 153 accompanying oscillation of the oscillating motor 151.

Seventh Embodiment

Figure 42:
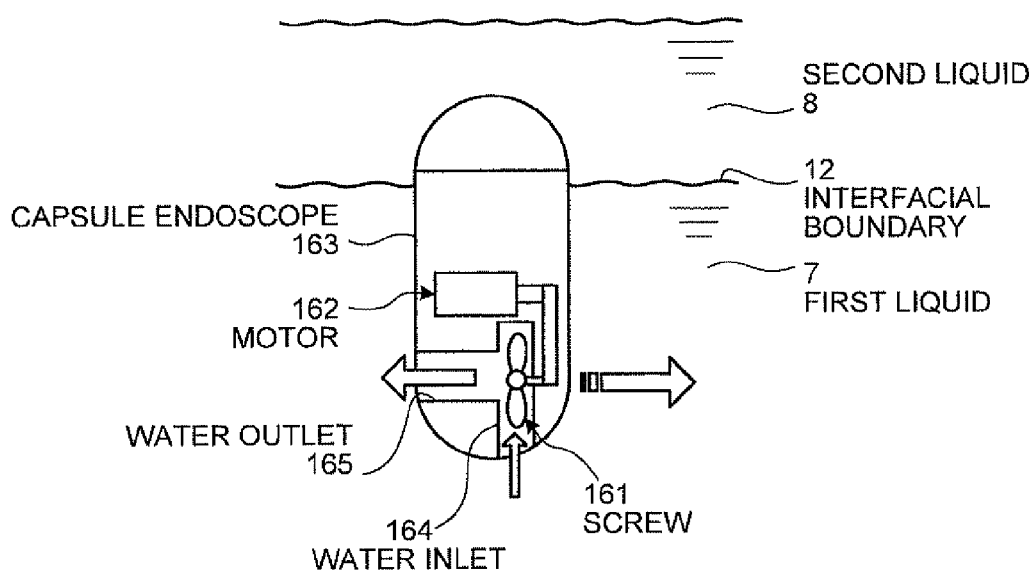
FIG. 42 is a schematic diagram showing the configuration of a portion of an intra-subject observation system in a seventh embodiment.

Next, a seventh embodiment of the present invention will be described with reference to FIG. 42. The same reference numerals are attached to the same components as those shown in FIG. 14 to FIG. 31 and a description thereof will not be repeated here. FIG. 42 is a schematic diagram showing the configuration of a portion of an intra-subject observation system in the seventh embodiment. The intra-subject observation system in the seventh embodiment comprises, instead of the capsule endoscope 4 shown in FIG. 14 or the like, a capsule endoscope 163 containing a screw 161 as a self-propelling mechanism and a motor 162 to drive the screw 161. The screw 161 is contained in the capsule endoscope 163 while maintaining a watertight state of other components and also communicatively connected to a water inlet 164 and a water outoutlet 165. The center of gravity of the capsule endoscope 163 is decentered toward the back-end side with the arrangement of the motor 162, a battery and the like, which are heavier among components in the capsule endoscope 163, on the back-end side.

The capsule endoscope 163 in the seventh embodiment images the inner wall of the stomach 3 while floating at the interfacial boundary 12 between the first liquid 7 and the second liquid 8 inside the stomach 3. Here, the capsule endoscope 163 in the seventh embodiment contains the screw 161 rotating by driving of the motor 162 and moves with a generated current at the interfacial boundary 12 while floating at the interfacial boundary 12 by causing the screw 161 to drive for propulsion so that the floating position thereof is successively forced to change. Accordingly, the capsule endoscope 163 can pick up images inside the stomach 3 in a wide range and make observations inside the stomach 3 exhaustively in a short time. The imaging position in the height direction can be controlled by adding the insertion amount of the first liquid 7. Further, by combining posture changes of the subject 2 described above, observations inside the stomach 3 can be made more thoroughly.

Incidentally, the motor 162 may be started to drive when the capsule endoscope 163 is swallowed, or after being swallowed into the stomach 3, the motor 162 may be started to drive by being switched on according to radio instructions from outside at an appropriate time.

Figure 43:
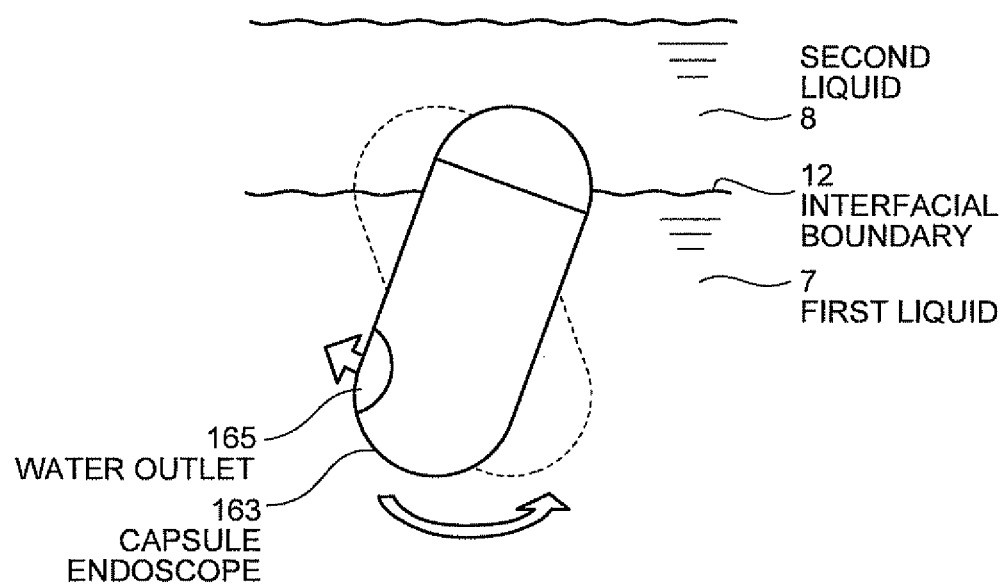
FIG. 43 is a schematic diagram showing an oscillating operation by intermittent driving.

Particularly by causing the motor 162 to be driven intermittently, the whole capsule endoscope 163 may be caused to oscillate, as shown in FIG. 43, to broaden the range of imaging field of view of the capsule endoscope 163.

Eighth Embodiment

Figure 44:
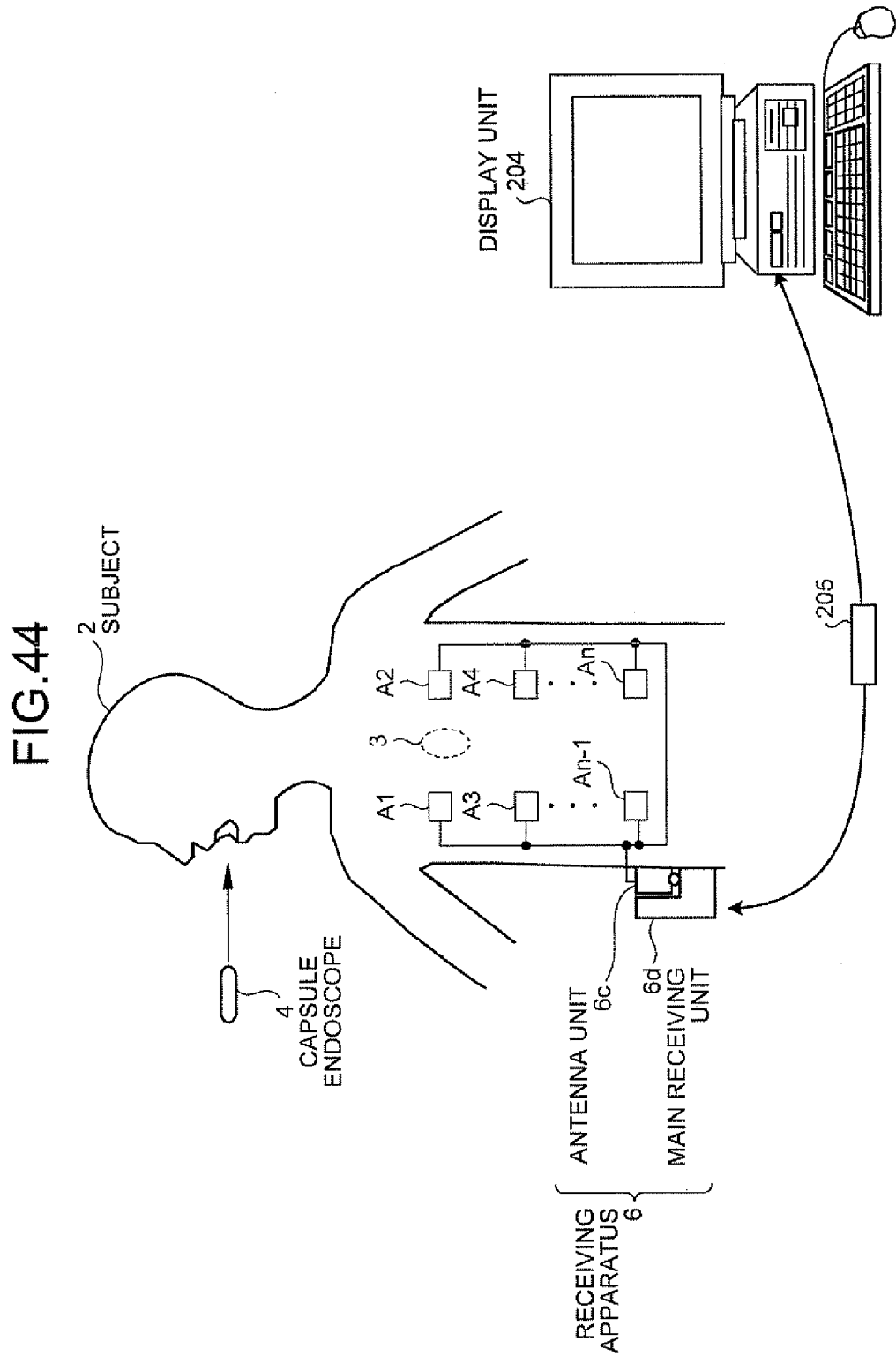
FIG. 44 is a schematic diagram showing the overall configuration of a radio in-vivo information acquiring system including a capsule medical apparatus according to the present invention.

FIG. 44 is a schematic diagram showing the overall configuration of a radio intra-subject observation system including a capsule medical apparatus according to the present invention. The radio intra-subject observation system will be described by taking, as a capsule medical apparatus, a capsule endoscope for imaging a tested portion inside a body cavity after being inserted into the body cavity through the mouth of a subject (human) as an example.

In FIG. 44, the radio intra-subject observation system comprises the receiving apparatus 6 having a radio receiving function and the capsule endoscope 4 inserted into the subject 2 to pick up images inside the body cavity before transmitting data such as an image signal to the receiving apparatus 6. The intra-subject observation system also comprises a display unit 204 for displaying images inside the body cavity based on an image signal received by the receiving apparatus 6 and a portable recording medium 205 for passing data between the receiving apparatus 6 and the display unit 204.

The receiving apparatus 6 comprises an antenna unit 6c having a plurality of antennas A1 to An for reception attached to the body surface outside the subject 2 and a main receiving unit 6d for performing processing of a radio signal received via the plurality of antennas A1 to An for reception and these units are removably connected via connectors or the like. Each of the antennas A1 to An for reception may also be fixed, for example, to a jacket wearable by the subject 2 so that the subject 2 mounts the antennas A1 to An for reception by wearing the jacket. In this case, the antennas A1 to An for reception may be freely removable from the jacket.

The display unit 204 is used to display images inside the body cavity or the like picked up by the capsule endoscope 4 and has a configuration like a workstation that displays images based on data acquired by the portable recording medium 205. More specifically, the display unit 204 may has a configuration to directly display an image such as a CRT display and a liquid crystal display or that to output an image to another medium such as a printer.

The portable recording medium 205 is removable from the main receiving unit 6d and the display unit 204 and has a structure allowing output or recording of information when inserted in both. In the eighth embodiment, the portable recording medium 205 records data transmitted from the capsule endoscope 4 by being inserted in the main receiving unit 6d while the capsule endoscope 4 moves inside the body cavity of the subject 2. When, after the capsule endoscope 4 is discharged from the subject 2, that is, after imaging inside the subject 2 is completed, the portable recording medium 205 is removed from the main receiving unit 6d and inserted into the display unit 204, which reads data recorded in the portable recording medium 205. By passing data between the main receiving unit 6d and the display unit 204 by using the portable recording medium 205 made of, for example, Compact-Flash (registered trademark) memory, the subject 2 can move more freely while images inside the body cavity being picked up than when the main receiving unit 6d and the display unit 204 are directly connected by wire. Here, the portable recording medium 205 is used for passing data between the main receiving unit 6d and the display unit 204, but the medium is not limited to this and, for example, the main receiving unit 6d may use another built-in recorder such as a hard disk, which is connected to the display unit 204 by wire or by radio to pass data between the hard disk and the display unit 204.

Figure 45:
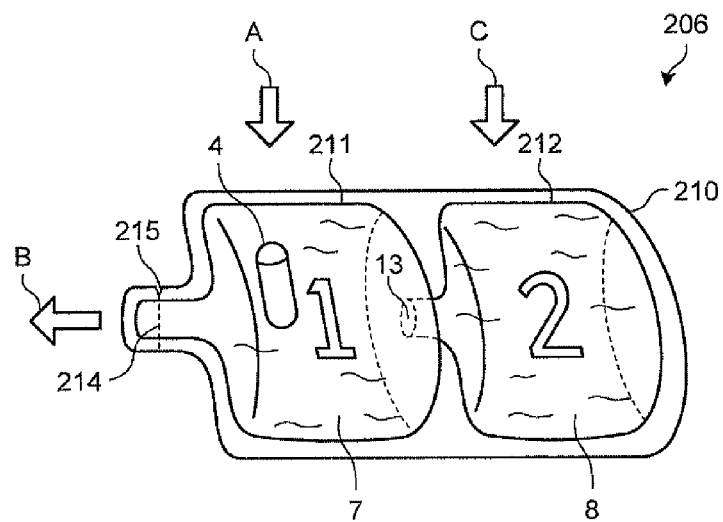
FIG. 45 is a perspective view showing the configuration of a capsule storing device according to an eighth embodiment storing intake materials taken by a subject.

Incidentally, the capsule endoscope 4 needs to maintain a sterilized state after being sterilized. Moreover, in examinations using the capsule endoscope 4, in addition to the capsule endoscope 4, a plurality of intake materials such as liquids (a liquid for extending or dilating luminal organs or a cleaning liquid for cleaning inside lumina) and a foaming agent for extending luminal organs may have to be given to a subject in specific order. Thus, in the eighth embodiment, the plurality of intake materials including the sterilized capsule endoscope 4 is stored in a capsule storing device. FIG. 45 is a perspective view showing the configuration of a capsule storing device 206 according to the eighth embodiment storing intake materials taken by a subject.

In FIG. 45, the capsule storing device 206 comprises a package 210 as a storage unit having storage areas 211, 212 for storing the capsule endoscope 4 and liquids, and a partition wall 213 provided between the storage areas 211, 212 to penetrably separate the storage areas 211, 212. The package 210 is formed of, for example, a resin material in an approximately cylindrical bag shape and has the two-part storage areas 211, 212 provided therein.

The storage areas 211, 212 are formed in an approximately cylindrical shape. For example, the capsule endoscope 4 and the first liquid 7 used by the subject 2 to swallow the capsule endoscope 4 are stored in the storage area 211, and the second liquid 8 is stored in the storage area 212. The partition wall 213 to separate the storage areas 211, 212 is allocated between the storage areas 211, 212. The partition wall 213 acts to separate the both storage areas 211, 212 against pressure from the storage area 211 direction (pressure applied from the storage area 211 side) and acts to allow penetration between the both storage areas 211, 212 against pressure from the storage area 212 direction (pressure applied from the storage area 212 side) in the same manner, for example, like a check valve. Or, the partition wall 213 acts to break against pressure of a certain level or higher from the storage area 212 direction. Such storage areas are not limited to two areas and a plurality of storage areas may be provided in the package 210 so that the first liquid 7 and the second liquid 8 are finely divided for storage therein.

A mouth 214 is provided at one end of the storage area 211 to allow intake materials inside the storage areas 211, 212 to discharge. The mouth 214 is formed normally to block the storage area 211 from outside and formed in such a way that the storage area 211 and the outside can be made to communicate when the subject 2 cuts a portion of the mouth 214 before the capsule endoscope 4 being swallowed. A slit 215 may also be provided in the package 210 near the mouth 214 so that a portion of the mouth 214 can easily be cut. Further, numbers "1" and "2" are marked on the package 210 above the storage areas 211, 212 to notify the subject 2 of the order to swallow.

Incidentally, the first liquid 7 and the second liquid 8 may be of different liquid quality. Both liquids may have different specific gravities, for example, while the first liquid 7 is water of specific gravity 1, the second liquid 8 is edible oil (such as olive oil) whose specific gravity is less than 1. The first liquid 7 and the second liquid 8 of such different liquid quality may be ones, for example, the subject 2 is caused to swallow when the position of the capsule endoscope 4 inside a luminal organ to be examined is adjusted. The first liquid 7 and the second liquid 8 may also be of the same liquid quality. For example, the first liquid 7 and the second liquid 8 may liquids of the same specific gravity. The first liquid 7 and the second liquid 8 of the same liquid quality may be ones, for example, the subject 2 is caused to swallow whose amount to be swallowed is adjusted in accordance with the physique of the subject 2. The capsule endoscope 4 may be one satisfying the size relation of specific gravity relative to the first liquid 7 and the second liquid 8 of (the first liquid 7)>(the capsule endoscope 4)>(the second liquid 8) or (the first liquid 7)=(the second liquid 8)>(the capsule endoscope 4).

The capsule endoscope 4 is, for example, a monocular type including an imaging optical system capable of imaging in the front-end direction, a circuitry such as a board, circuit components, and a transmitting antenna, a battery, an acceleration sensor, and an angular velocity sensor inside a capsule casing (not shown) insertable into the body cavity of the subject 2 and is formed by fluid-tightly sealing the inside of the capsule casing. The capsule endoscope 4 picks up images of objects (inner parts of organs of the subject 2) positioned in the gravity direction while floating in the liquid. The balance of the center of gravity of the capsule endoscope 4 in the front-back direction may be changed so that, for example, the front-end side thereof is made relatively lighter and an upper side in the gravity direction can be imaged by the imaging optical system, or the balance of the center of gravity of the capsule endoscope 4 in the front-back direction may be changed so that the front-end side thereof is made relatively heavier and an lower side in the gravity direction can be imaged by the imaging optical system.

Figure 46:
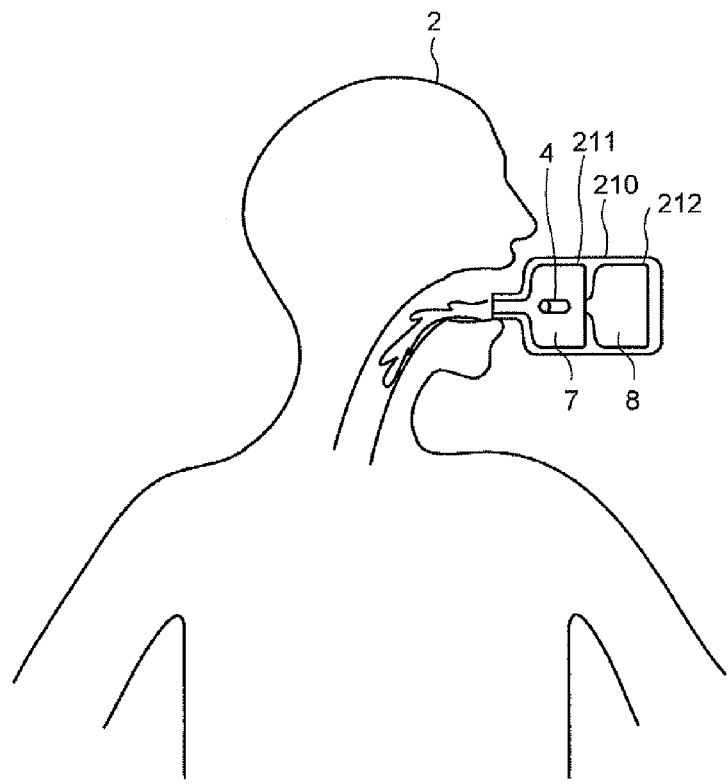
FIG. 46 is a schematic diagram showing a state in which the subject takes the intake material shown in FIG. 45.
Figure 47:
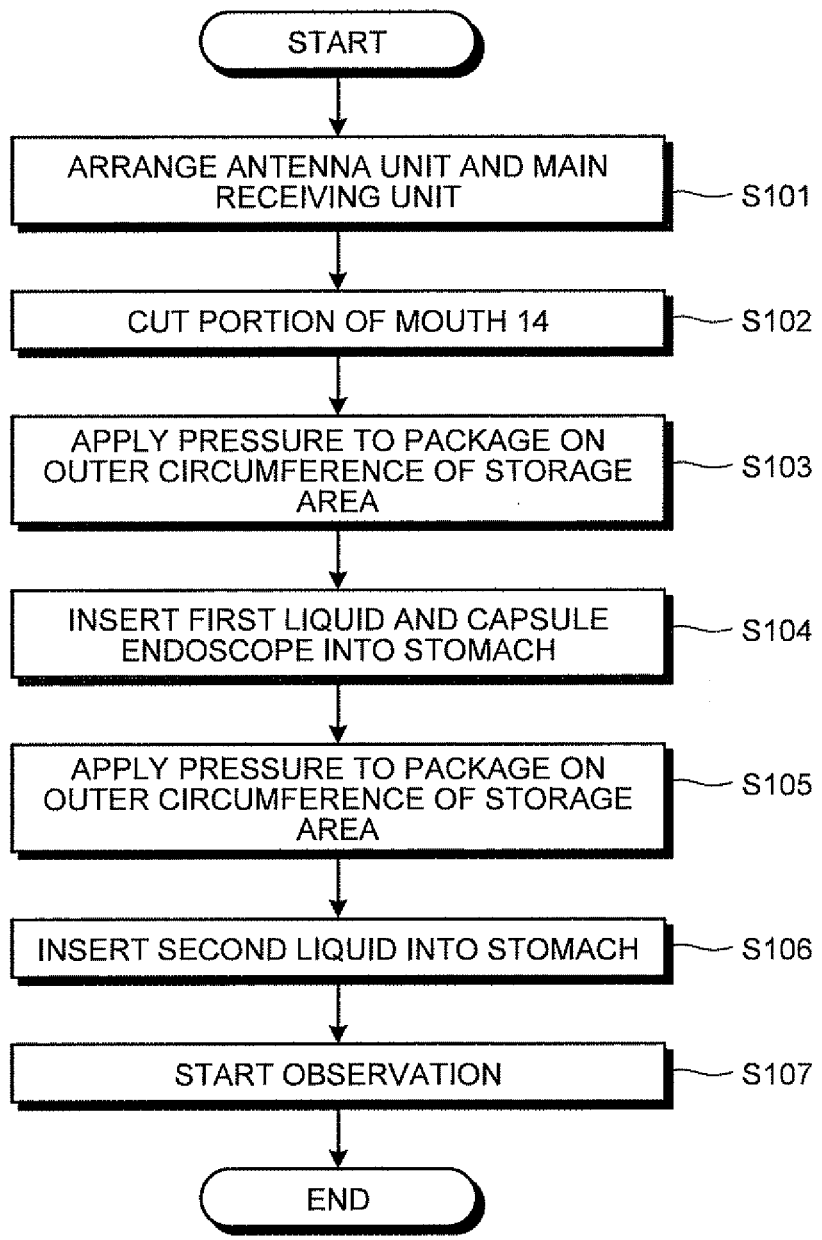
FIG. 47 is an outline flow chart showing the procedure for the feeding method of an intake material according to the eighth embodiment of the present invention.
Figure 48:
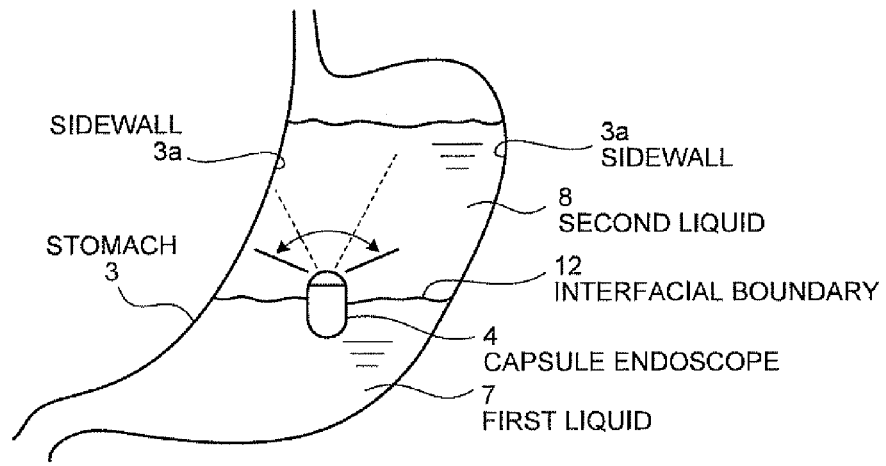
FIG. 48 is a schematic front view showing the appearance of the stomach during observation in the eighth embodiment of the present invention.

A series of feeding methods in which the subject 2 takes in the capsule endoscope 4 using the capsule storing device 206 to insert the capsule endoscope 4, for example, into stomach will be described using drawings of FIG. 46 to FIG. 48. FIG. 46 is a schematic diagram showing a state in which the subject takes the intake material shown in FIG. 45, FIG. 47 is an outline flow chart showing the procedure for the feeding method of an intake material according to the eighth embodiment, and FIG. 48 is a schematic front view showing the appearance of stomach during observation. In the eighth embodiment, a case in which the capsule endoscope 4 satisfies the size relation of specific gravity relative to the first liquid 7 and the second liquid 8 of (the first liquid 7)>(the capsule endoscope 4)>(the second liquid 8) and the balance of the center of gravity in the frontback direction is changed so that the front-end side thereof is made relatively lighter in order to allow imaging in the gravity direction, for example, the upper side in the gravity direction by the imaging optical system while the capsule endoscope 4 floats in the liquid before being inserted into the stomach 3.

In FIG. 47, before intake materials are fed, the antenna unit 6c having the antennas A1 to An for reception for receiving a signal from the capsule endoscope 4 is arranged at a predetermined position of the subject 2 and the main receiving unit 6d is arranged at a position near the subject 2 (step S101). Next, a portion of the mouth 214 is cut (step S102), the mouth 214 is brought closer to the mouth, as shown in FIG. 46, and, by applying pressure (pressure in the direction of an arrow A in FIG. 45) to the package 210 on an outer circumference of the storage area 211 (for example, a partial area of the package 210 where the swallowing order "1" is marked) by, for example, fingers (step S103), the capsule endoscope 4 and the first liquid 7 are discharged into the mouth of the subject 2 (the direction of an arrow B in FIG. 45).

Accordingly, the subject 2 becomes able to swallow the first liquid 7 and the capsule endoscope 4 into the body and the swallowed first liquid 7 and capsule endoscope 4 are inserted into the stomach 3 (step S104). In this case, the subject 2 swallows intake materials in a standing or sitting position. In this state, the partition wall 213 of the package 210 maintains a closed state and the storage area 211 and the storage area 212 remain separated. The capsule endoscope 4 may be activated, for example, like a conventional example, by mounting a permanent magnet on the package 210 and taking out the capsule endoscope 4, or a permanent magnet may be brought closer to the capsule endoscope 4 after being taken out from the package 210. When the capsule endoscope 4 is activated, LED of the imaging optical system blinks and thus, the package is preferably formed of a transparent material so that the subject can confirm the blink.

Next, when pressure (pressure in the direction of an arrow C in FIG. 45) is applied to the package 210 on an outer circumference of the storage area 212 (for example, a partial area of the package 210 where the swallowing order "2" is marked) (step S105), the partition wall 213 opens to the storage area 211 to allow penetration of the storage area 211 and the storage area 212 so that the second liquid 8 in the storage area 212 is discharged into the mouth of the subject (the direction of the arrow B in FIG. 45) via the storage area 211. Accordingly, the subject 2 becomes able to swallow the second liquid 8 into the body and the swallowed second liquid 8 are inserted into the stomach 3 (step S106). When the capsule endoscope 4, the first liquid 7, and the second liquid 8 are inserted into the stomach 3, the stomach 3 extends based on the intake and, as shown in FIG. 48, a laminated state in which the second liquid 8 forms the interfacial boundary 12 above the first liquid 7 is brought about due to differences in specific gravity, with the capsule endoscope 4 having an intermediate specific gravity positioned at the interfacial boundary 12 to float there. Since the balance of the center of gravity in the front-back direction is changed so that the front-end side thereof is made relatively lighter, the capsule endoscope 4 stabilizes and floats in a standing state (vertical state) with the front-end side to be the imaging direction directed upward at the interfacial boundary 12. The capsule endoscope 4 acquires images of the sidewall 3a by imaging the upper side of the stomach 3 in such a stable standing state and transmits the acquired images to the receiving apparatus 6 and, as a result, an observation of the stomach 3 can be started (step S107).

Thus, in the eighth embodiment, the capsule endoscope 4 and the first liquid 7, and the second liquid 8 are stored in the plurality of the storage areas 211, 212 of the package 210 respectively as intake materials of the subject 2, these storage areas 211, 212 are communicatively connected, a partition wall is provided between the storage areas 211, 212, intake materials are discharged in an open state of the partition wall when pressure in one direction is applied, and intake materials are allowed to be fed to the subject 2 in specific order based on numbers marked on the package 210 and therefore, the subject 2 is enabled to take in a plurality of intake materials needed for examination correctly and easily in specific order. Since the order of intake becomes correct in the eighth embodiment, anybody can deal with the package 210 easily so that the examination is made easier. Accordingly, a probability that the subject 2 takes in intake materials in incorrect order is reduced and examinations advance smoothly so that prevention of incorrect examinations and more efficient examination times can be promoted. Moreover, the capsule storing device 206 consists of one package and thus, there is no need for other people than the subject 2 to touch the package so that examinations can hygienically be completed.

Since, in the eighth embodiment, the stomach 3 can be caused to extend by drinking liquids, sufficient space can be secured inside organs required for observation by the capsule endoscope 4, the inner wall of organs can be imaged more closely, and observations inside the stomach 3 can be made without omission. The capsule endoscope 4 floats at the interfacial boundary 12 rocking randomly only by changing the position of the interfacial boundary 12 inside the stomach 3 in combination with posture changes of the subject 2 itself. With the capsule endoscope 4 rocking randomly, imaging regions inside the stomach 3 to be imaged by the capsule endoscope 4 can be caused to change and thus, the stomach 3 can be observed more thoroughly without omission. Further, by using the capsule endoscope 4 provided with an imaging optical system having a wider angle shown by solid lines instead of dotted lines shown in FIG. 48, observations inside the stomach 3 in a wider range can be made with a smaller posture change.

Figure 49:
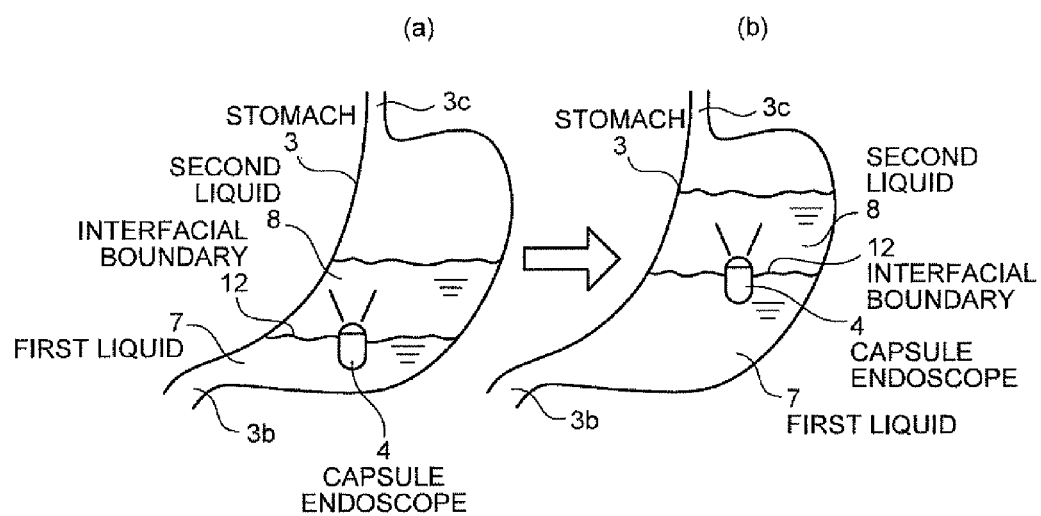
FIG. 49 is a schematic front view showing the appearance inside the stomach before and after increasing an intake of the first liquid.

Also in the eighth embodiment, observations inside the stomach 3 can be caused to be made with the floating position in the gravity direction of the capsule endoscope 4 inside the stomach 3 set at an arbitrary position by causing the height position of the interfacial boundary 12 to change by changing intakes of the first liquid 7 and the second liquid 8 into the stomach 3, FIG. 49 is a schematic front view showing the appearance inside the stomach 3 before and after increasing an intake of the first liquid 7. That is, as shown in FIG. 49(a), after starting an observation by swallowing the capsule endoscope 4 together with predetermined amounts of the first liquid 7 and the second liquid 8, as shown in FIG. 49(b), the sidewall 3a can be observed successively from the lower part (pyloric part of stomach) 3b toward the upper part (cardiac part of stomach) 3c of the stomach 3 by the first liquid 7 additionally being drunk if necessary to successively increase the intake of the first liquid 7 inside the stomach 3 so that the position of the interfacial boundary 12 gradually rises. Also in this case, the imaging region by the capsule endoscope 4 can be changed only by changing the position of the interfacial boundary 12 inside the stomach 3 in combination with a posture change of the subject 2 itself each time the first liquid 7 is added so that observations inside the stomach 3 can be made exhaustively without omission. Also when the balance of the center of gravity is changed in the front-back direction to make the front-end side of the capsule endoscope 4 relatively heavier so that the lower side in the gravity direction can be imaged by the imaging optical system, like the above case, the imaging region by the capsule endoscope 4 can be changed only by changing the position of the interfacial boundary 12 inside the stomach 3 so that observations inside the stomach 3 can be made exhaustively without omission. Accordingly, a plurality of images picked up randomly can be combined based on correlations of between images after an examination so that it becomes possible to create an overall image inside the stomach 3 and when the image is presented to a physician or the like, to make an efficient diagnosis.

If liquids of the same specific gravity are used as the first liquid 7 and the second liquid 8, for example, water of the specific gravity 1 is used for both, the same effect as that described above can be achieved, but in this case, the capsule endoscope 4 is in the standing position at the interfacial boundary between the water and air space. Thus, viscosity becomes weaker compared with a case of two liquids of different specific gravities and, if the interfacial boundary fluctuates, the capsule endoscope 4 moves (falls) more widely, making it difficult for the capsule endoscope 4 to float in the stable standing position with less movement. When two liquids of different specific gravities are used, an observation plane of the capsule endoscope 4 is always in the liquid and satisfactory images can be obtained because such a scratch or dirt on the observation plane of the capsule endoscope 4 becomes inconspicuous. Further in the eighth embodiment, the stomach is filled with the first liquid 7 and the second liquid 8 and thus, supersonic waves propagate satisfactorily. Thus, the position and orientation of the capsule endoscope can be determined by picking up three-dimensional images inside the stomach by a 3D supersonic probe or the like provided outside the subject when acquiring images. Then, an image of the inner wall of the stomach can be constructed with high precision by image combination based on the position or orientation information, contributing to a diagnosis with high precision.

The position of the capsule endoscope 4 can be detected, for example, by an acceleration sensor or an angular velocity sensor provided inside the capsule endoscope 4, but the receiving apparatus 6 has a plurality of antennas A1 to An for reception for receiving a radio signal from the capsule endoscope 4 and a position detection function for calculating the position of the capsule endoscope 4 from each received strength of the plurality of antennas A1 to An for reception may be provided. Then, the above image combination may be performed based on a result of the position detection function. In this case, precision of image combination is further improved so that a more reliable diagnosis can be made.

Twelfth Modification

Figure 50:
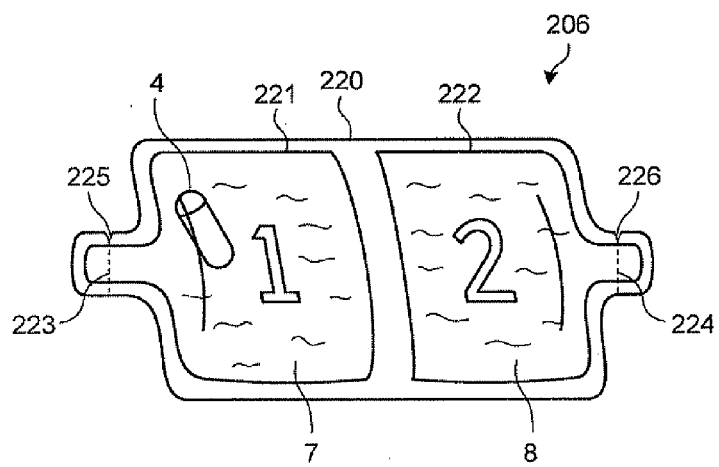
FIG. 50 is a perspective view showing the configuration of a twelfth modification of the capsule storing device.

FIG. 50 is a perspective view showing the configuration of a twelfth modification of the capsule storing device 206 according to the eighth embodiment in FIG. 45. In FIG. 50, the capsule storing device 206 comprises therein a package 220 having storage areas 221, 222 separated completely in an impenetrable state. Mouths 223, 224 through which the subject 2 swallows intake materials inside the storage areas 221, 222 are separately provided at both ends thereof.

The twelfth modification is the same as the eighth embodiment in that the capsule endoscope 4 and the first liquid 7 are stored in the storage areas 221 and the second liquid 8 is stored in the storage areas 222, and the numbers "1" and "2" are marked on the package 220 above the storage areas 221, 222 to notify the subject 2 of the order to swallow. Also just like the eighth embodiment, slits 225, 226 are provided in the package 220 near the mouths 223, 224 so that a portion of the mouths 223, 224 can easily be cut.

In the twelfth modification, the subject cuts a portion of the mouth 223 and applies pressure to the package 220 on an outer circumference of the storage area 221 (for example, a partial area of the package 220 where the swallowing order "1" is marked) so that the capsule endoscope 4 and the first liquid 7 inside the storage area 221 are discharged into the mouth of the subject 2. Then, the subject 2 turns around the package 220 to the storage area 222 side, cuts a portion of the mouth 224, and applies pressure to the package 220 on an outer circumference of the storage area 222 (for example, a partial area of the package 220 where the swallowing order "2" is marked) so that the second liquid 8 inside the storage area 222 is discharged into the mouth of the subject 2.

Also in the twelfth modification, as described above, the capsule endoscope 4 and the first liquid 7, and the second liquid 8 are stored in the plurality of the storage areas 221, 222 of the package 220 respectively as intake materials of the subject 2 and intake materials are allowed to be fed to the subject 2 in specific order based on numbers marked on the package 220 and therefore, like the eighth embodiment, the subject is enabled to take in a plurality of intake materials needed for examination correctly and easily in specific order, Markings on the package are not limited to the above numbers and may be alphabets like "A", "B", and "C" or any other desired marking allowing indication of specific order may be used regardless of marking modes thereof.

The capsule storing device 206 according to the twelfth modification consists of the package 220 having the storage areas 221, 222 and therefore, the configuration thereof is simple, the manufacture thereof is easily automated, and also can be manufactured easily. Like the eighth embodiment, the capsule storing device 206 according to the twelfth modification consists of one package and therefore, there is no need for other people than the subject to touch the package so that examinations can hygienically be completed.

Thirteenth Modification

Figure 51:
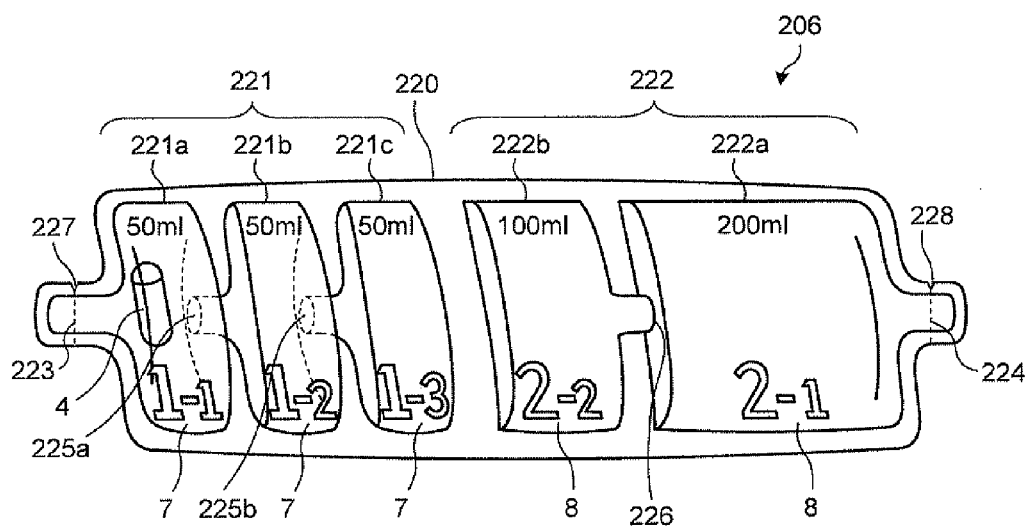
FIG. 51 is a perspective view showing the configuration of a thirteenth modification of the capsule storing device.

FIG. 51 is a perspective view showing the configuration of a thirteenth modification of the capsule storing device 206 according to the eighth embodiment in FIG. 45. In the thirteenth modification, the capsule storing device 206 is suitable as a liquid insertion apparatus when, for example, first and second liquids of different liquid quality are taken in and the position of the capsule endoscope 4 is controlled in a luminal organ (stomach) or the intake of liquid is changed in accordance with the physique or the size of stomach of the subject 2. That is, in FIG. 51, the capsule storing device 206 according to the thirteenth modification comprises the storage area 221 comprised of a plurality of storage areas 221a to 221c for dividing and storing the first liquid 7 and the storage area 222 comprised of a plurality of storage areas 222a and 222b for dividing and storing the second liquid 8. The storage area 221 and the storage area 222 are completely separated in an impenetrable state. A partition wall 225a penetrably separating the storage areas 221a and 221b is provided between the storage areas 221a and 221b and a partition wall 225b penetrably separating the storage areas 221b and 221c is provided between the storage areas 221b and 221c, and on the other hand, a partition wall 226 penetrably separating the storage areas 222a and 222b is provided between the storage areas 222a and 222b. The partition walls 225a, 225b act, like the partition wall 213 in the eighth embodiment, to allow penetration between both storage areas only against pressure in a direction from the storage area 221c or the storage area 221b to the storage area 221a in the same manner, for example, like a check valve. The partition wall 226 acts, like the partition wall 213 in the eighth embodiment, to allow penetration between both storage areas only against pressure in a direction from the storage area 222b to the storage area 222a in the same manner, for example, like a check valve. The storage areas 221 and 222 are formed in a completely separated state so that one storage area is not affected by pressure applied to the other storage area.

The mouth 223 is provided at one end of the storage area 221a to allow the intake materials (the capsule endoscope 4 and the first liquid 7) inside the storage areas 221a to 221c to discharge and the mouth 224 is provided at one end of the storage area 222a to allow the intake material (the second liquid 8) inside the storage areas 222a and 222b to discharge. These mouths 223, 224 are formed normally to block the storage areas 221a, 222a from outside and formed in such a way that the storage areas 221a, 222a and the outside can be made to communicate when the subject 2 cuts a portion of the mouths 223, 224 before the intake materials being swallowed.

Slits 227, 228 may also be provided in the package 220 near the mouths 223, 224 so that a portion of the mouths 223, 224 can easily be cut. Further, numbers "1-1", "1-2", and "1-3" are marked on the package 220 above the storage areas 221a to 221c to notify the subject 2 of the order to swallow. On the package 220 above the storage areas 222a, 222b, on the other hand, numbers "2-1" and "2-2" are marked in the same manner to notify the subject 2 of the order to swallow. In the thirteenth embodiment, for example, 50 ml of the first liquid 7 is stored in each of the storage areas 221a to 221c and the capsule endoscope 4 is stored in the storage area 221a together with the first liquid 7. The second liquid 8 is divided into 200 ml of the second liquid 8 stored in the storage area 222a and 100 ml of the second liquid 8 stored in the storage area 222b. The second liquid 8 is divided and stored in the storage areas 222a, 222b. For example, 200 ml of the second liquid 8 is stored in the storage area 222a and 100 ml of the second liquid 8 is stored in the storage area 222b. In the thirteenth embodiment, the capsule endoscope 4 may also be stored in a storage area separately from the first liquid 7.

When the subject 2 takes in the capsule endoscope 4 using the capsule storing device 206, the subject 2 first cuts a portion of the mouth 223 and applies pressure to a storage area (one of the storage areas 221a to 221c) of a prescribed required intake. If 100 ml of the first liquid 7 and the capsule endoscope 4 should be taken in, for example, the capsule endoscope 4 and the first liquid 7 (100 ml) in the storage areas 221a and 221b are discharged into the mouth of the subject 2 (the direction of the arrow B in FIG. 45) by applying pressure to the package 220 on an outer circumference of the storage area 221b (for example, a partial area of the package 220 where the swallowing order "1-2" is marked). Accordingly, the subject 2 can take in the capsule endoscope 4 and the prescribed required intake of the first liquid 7 into the body thereof. In this state, the partition wall 225a opens to the storage area 221a side to allow penetration of the storage area 221a and the storage area 221b. On the other hand, the partition wall 225b separates the storage area 221b and the storage area 221c by maintaining a closed state to prevent the first liquid 7 in the storage area 221c from being discharged. Since the subject can take in liquids by directly putting the mouth 223 in the mouth and thus, the liquids can easily be taken in regardless of the posture of the subject 2. If, for example, the subject 2 takes the posture of the left lateral position, right lateral position, or face-up position, liquids can be taken in easily.

Next, the subject 2 turns around the package 220 to the storage area 222 side, cuts a portion of the mouth 224, and applies pressure to a storage area (one of the storage areas 222a and 222b) of a prescribed required intake. If 200 ml of the second liquid 8 should be taken in, for example, the second liquid 8 (200 ml) in the storage area 222a is discharged into the mouth of the subject 2 by applying pressure to the package 220 on an outer circumference of the storage area 222a (for example, a partial area of the package 220 where the swallowing order "2-1" is marked). Accordingly, the subject 2 can take in the prescribed required intake of the second liquid 8 into the body thereof. In this state, the partition wall 226 separates the storage area 222a and the storage area 222b by maintaining a closed state to prevent the second liquid 8 in the storage area 222b from being discharged.

Also in the thirteenth modification, as described above, the capsule endoscope 4 and the first liquid 7, and the second liquid 8 are stored in the plurality of the storage areas 221, 222 of the package 220 respectively as intake materials of the subject 2 and intake materials are allowed to be fed to the subject 2 in specific order based on numbers marked on the package 220 and therefore, an effect similar to that of the eighth embodiment can be achieved. The first liquid 7 and the second liquid 8 are divided and stored in the plurality of the storage areas 221a to 221c and the storage areas 222a and 222b respectively before required intakes thereof being allowed to discharge to the outside and therefore, intake materials of proper intakes can be fed to the subject it necessary. For the subject of the average physique, the required total intake is 500 ml (fed, for example, by dividing the liquids in three storage areas 100 ml, 200 ml, and 200 ml) or so. If the subject 2 is large, it is preferable to allow feeding of up to 1000 ml of intake materials such as liquids to the subject 2 using the capsule storing device 206, which is configured to have storage areas to be able to store intake materials of up to 1000 ml.

Ninth Embodiment

Figure 52:
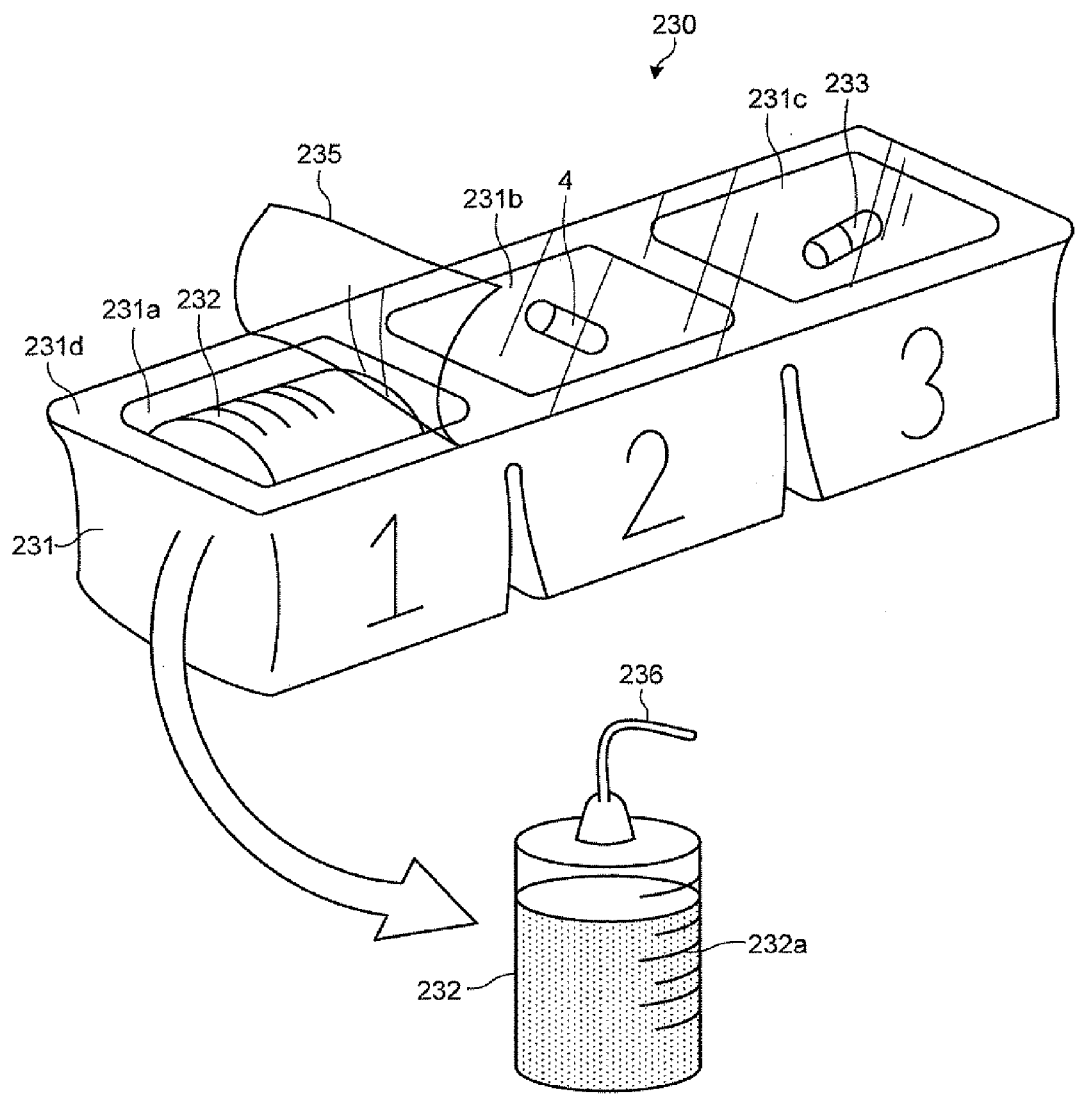
FIG. 52 is a perspective view showing the configuration of a capsule storing device in a ninth embodiment of the present invention.
Figure 53:
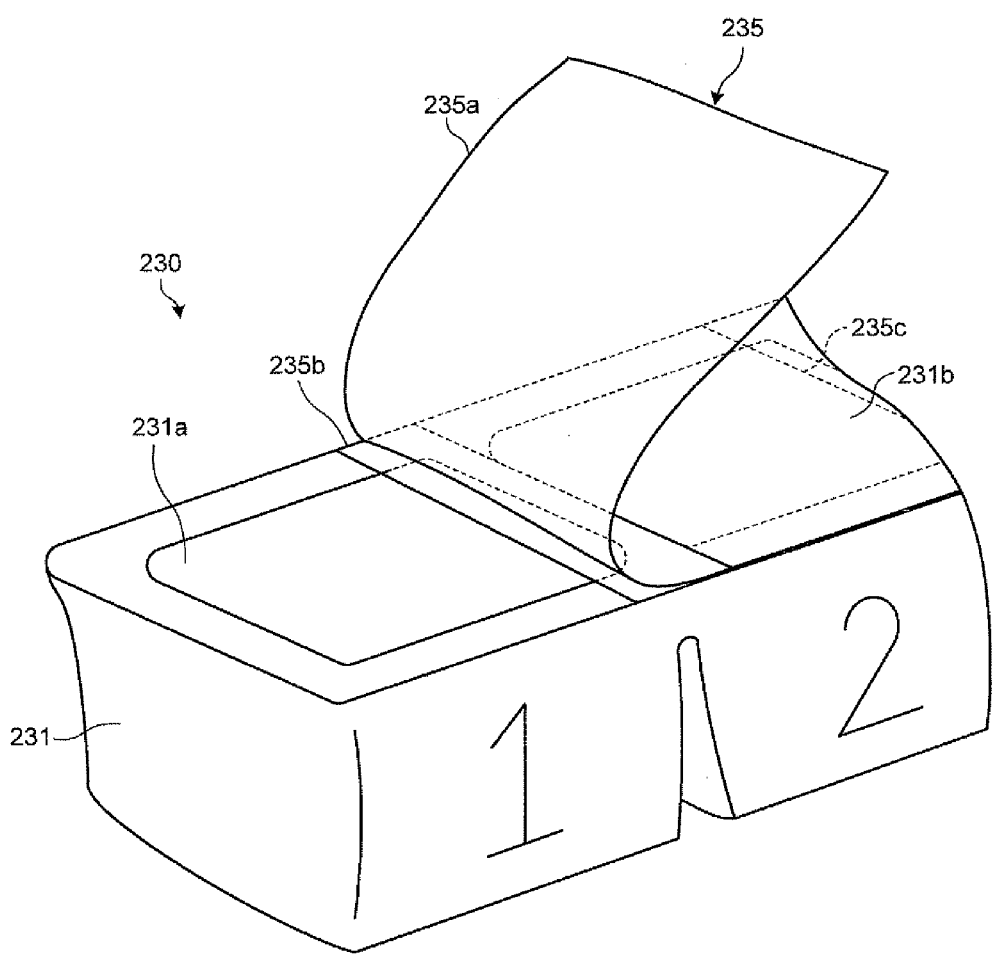
FIG. 53 is a partially enlarged view partially enlarging a portion of FIG. 52.

FIG. 52 is a perspective view showing the configuration of a capsule storing device in a ninth embodiment for storing intake materials to be taken in by a subject. FIG. 53 is a partially enlarged view partially enlarging a portion of FIG. 52. In FIG. 52 and FIG. 53, a capsule storing device 230 comprises a blister pack 231 as a storage unit having storage areas 231a to 231c for storing a liquid, the capsule endoscope 4, and a foaming agent respectively, and a sterilized seal 235 provided on an upper surface of each opening of the blister pack 231. The blister pack 231 has the storage areas 231a to 231c whose cross section is concave and formed into three box shapes and is formed by linking these box shapes in a row at the upper surface of openings. A sealing surface 231d for closing each opening by heat sealing of the sterilized seal 235 is provided on the upper surface of the openings. The sealing surface 231d is formed by surrounding an outer circumference on the upper surface of the openings of the storage areas 231a to 231c arranged in a row in an endless form.

A liquid is stored in the storage area 231a and a "1" is marked on the side of the blister pack 231 where the storage area 231a is formed to notify the subject 2 of the swallowing order. This liquid consists of water whose specific gravity is 1 and is stored in the storage area 231a, for example, with a straw 236 inserted from above and housed in a cylindrical bottle 232 with graduations 232a from which the total volume of the liquid and the intake of the subject 2 are recognizable at a glance. The storage area 231b has the capsule endoscope 4 having the same configuration as that in the eighth embodiment whose specific gravity is set a little less than the specific gravity 1 stored therein, and "2" is marked on the side of the blister pack 231 where the storage area 231b is formed to notify the subject 2 of the order in the same manner. The storage area 231c has a foaming agent for extending the stomach 3 of the subject 2 stored therein and "3" is marked on the side of the blister pack 231 where the storage area 231c is formed to notify the subject 2 of the order in the same manner. The foaming agent is stored, for example, in a state housed in a housing case 233.

The sterilized seal 235 is sealed a little longer than the sealing surface 231d on the edge side of, for example, the storage area 231a, and this one sterilized seal 235 closes the upper surface of openings of the blister pack 231. The sterilized seal 235 may be made tearable from the storage area 231a side by tearing off the sterilized seal 235 from the blister pack 231 by holding a protruding tongue-like portion. The sterilized seal 235 may consist of three sterilized seals 235a, 235b, and 235c corresponding to the three storage areas 231a, 231b, and 231c. As shown, for example, in the enlarged view of FIG. 53, sterilized seal 235a and 235b may close the upper surface of openings respectively with portions of the adjacent storage areas 235a and 235b overlapping. In this case, the upper surface of the opening is first closed by the sterilized seal 235c of the storage area 231c whose order of being swallowed by the subject 2 is later, and the upper surface of the opening is lastly closed by the sterilized seal 235a of the storage area 231a whose order of being swallowed is earliest. An edge of a sterilized seal in later order is sealed to cover the storage area of the order just before a little. In this case, it is preferable to make adhesive strength between a sterilized seal and the sealing surface 231d stronger than that between seals to prevent each sterilized seal from being peeled successively.

Therefore, when the sterilized seal 235a of the storage area 231a with the number "1" marked is torn off from the blister pack 231, as shown in FIG. 53, the bottle 232 in which water is stored and an edge of the sterilized seal 235b of the second storage area 231b appear, making the sterilized seal 235b of the next storage area 231b tearable. The subject 2 is enabled to take out the bottle 232 to drink an amount of liquid (for example, water) required for the body. Since the bottle 232 has the graduations 232a indicating the volume of water, the subject 2 drinks the amount of water in accordance with the size of body of the subject through the straw 236 while referring to the graduations 232a. The intake of water to be taken in by the subject 2 may be determined from information of the weight, height, chest circumference and the like of the subject 2 measured in advance or from information of the size of stomach acquired from X rays or ultrasound scanning of the abdomen.

Next, when the subject 2 tears off the sterilized seal 235b of the storage area 231b with the number "2" marked from the blister pack 231, the capsule endoscope 4 and an edge of the sterilized seal 235c of the third storage area 231c appear, making the sterilized seal 235c of the next storage area 231c tearable. The subject 2 picks up and swallows the capsule endoscope 4. Accordingly, the subject 2 is enabled to swallow water and the capsule endoscope 4 into the body and the swallowed water and capsule endoscope 4 are inserted into the stomach 3. The capsule endoscope 4 is activated in the same manner as in the eighth embodiment.

Then, when the sterilized seal 235c of the storage area 231c with the number "3" marked is torn off from the blister pack 231, the housing case 233 in which a foaming agent is stored appears. The subject 2 picks up the housing case 233 to swallow the foaming agent. At this point, water to allow reaction (foaming) with the foaming agent may also be taken in. If the foaming agent is taken in, pressure inside the stomach rises, making belching more likely. However, belching must be stifled for examinations and thus, it is difficult to take in a liquid or capsule endoscope after taking in a foaming agent. Consequently, from this standpoint, it is desirable for the subject to take in the foaming agent at the end. If an observation should be made by dropping a capsule endoscope into the stomach extended by a foaming agent or liquid, the capsule endoscope (or any other liquid) may be swallowed after taking in the foaming agent if necessary.

Figure 54:
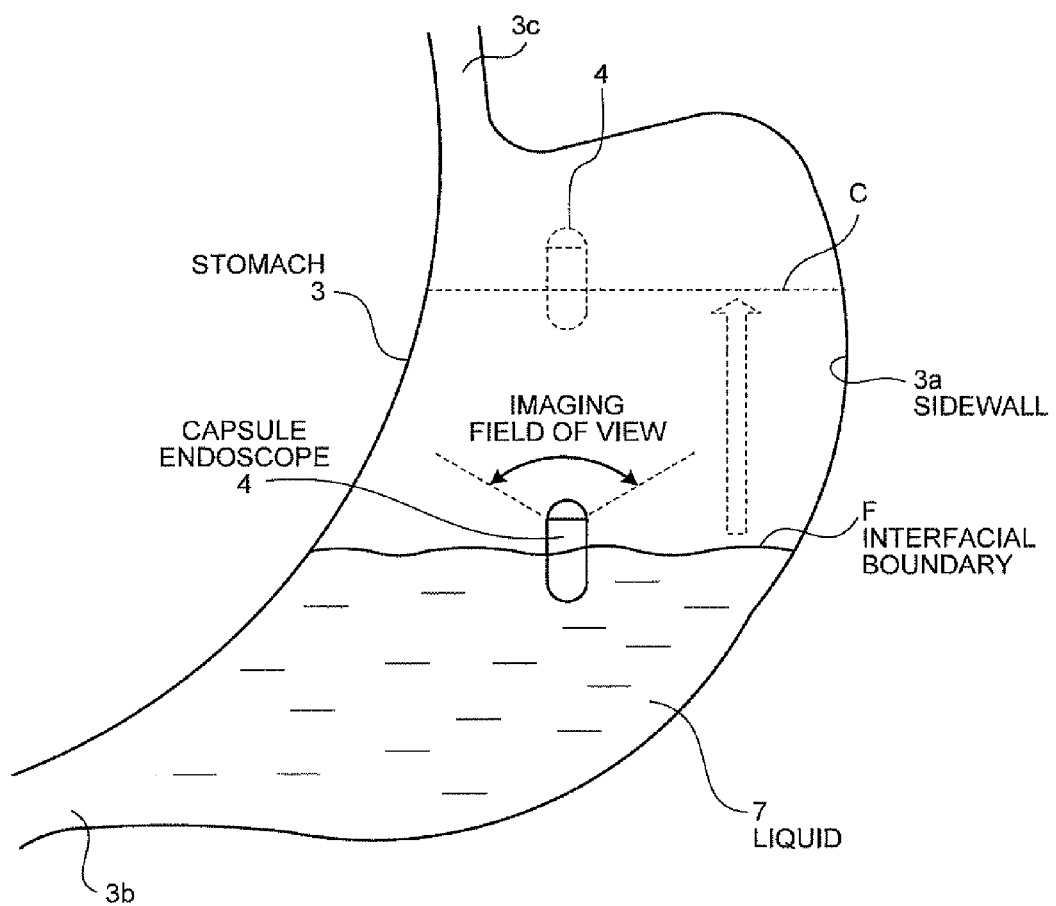
FIG. 54 is a schematic front view showing the appearance of the stomach during observation in the ninth embodiment of the present invention.

When the capsule endoscope 4, the liquid, and the foaming agent are inserted into the stomach 3, the stomach 3 is extended by the foaming agent and, as shown in FIG. 54, an interfacial boundary F is formed by the liquid 7 and air space due to a difference in specific gravity and the capsule endoscope 4 whose specific gravity is smaller than that of the liquid 7 floats positioned at the interfacial boundary F. Since the balance of the capsule endoscope 4 in the front-back direction is changed so that the front-end side is made relatively lighter, the capsule endoscope 4 will float by stabilizing in the standing state (vertical state) in which the front-end side to be the imaging direction at the interfacial boundary F is directed upward in the gravity direction. The capsule endoscope 4 acquires images of the sidewall 3a by imaging the upper side of the stomach 3 in such a stable standing state and transmits the acquired images to the receiving apparatus 6 and, as a result, an observation of the stomach 3 can be started.

Also in the ninth embodiment, observations inside the stomach 3 can be caused to be made with the floating position in the gravity direction of the capsule endoscope 4 inside the stomach 3 set at an arbitrary position by causing the height position of the interfacial boundary F to change by changing an intake of the first liquid 7 into the stomach 3. That is, after starting an observation by swallowing the capsule endoscope 4 together with a predetermined amount of the first liquid 7, the sidewall 3a can be observed successively from the lower part (pyloric part of stomach) 3b toward the upper part (cardiac part of stomach) 3c of the stomach 3 by the first liquid 7 additionally being drunk if necessary to successively increase the intake of the first liquid 7 inside the stomach 3 so that the position of the interfacial boundary F gradually rises, for example, from a solid line position to a dotted line position. Also in this case, the imaging region by the capsule endoscope 4 can be changed only by changing the position of the interfacial boundary F inside the stomach 3 in combination with a posture change of the subject 2 itself each time the first liquid 7 is added so that imaging inside the stomach 3 can be made without omission. Also when the balance is changed in the front-back direction to make the front-end side of the capsule endoscope 4 relatively heavier so that the lower side in the gravity direction can be imaged by the imaging optical system, like the above case, the imaging region by the capsule endoscope 4 can be changed only by changing the position of the interfacial boundary F inside the stomach 3 so that imaging inside the stomach 3 can be made without omission. Accordingly, a plurality of images picked up randomly can be combined based on correlations of between images after an examination so that it becomes possible to create an overall image of the stomach 3 and when the image is presented to a physician or the like, to make an efficient diagnosis.

In the ninth embodiment, as described above, a plurality of intake materials such as a liquid, the capsule endoscope 4, and a foaming agent are stored in the partitioned storage areas 231a to 231c of the blister pack 231 and the sterilized seal 235 is peeled in specific order based on numbers marked on the blister pack 231 to allow feeding of each intake material to the subject 2 in the specific order and therefore, the subject 2 is enabled to take in a plurality of intake materials needed for examination correctly and easily in specific order. Since some types of capsule medical apparatus in a capsule shape are dissolved in a liquid, deformation and deterioration of individual intake materials can be prevented, like the ninth embodiment, by storing each intake material separately in each storage area.

A liquid or foaming agent may not be taken in for examinations inside the body cavity by the capsule endoscope 4. In such a case, it is also possible to store the capsule endoscope 4 and a foaming agent, or a liquid and the capsule endoscope 4 separately in the storage areas of the blister pack 231 and to peel the sterilized seal 235 in specific order based on numbers marked on the blister pack 231 to enable the subject 2 to take in the capsule endoscope 4 and the foaming agent, or the liquid and the capsule endoscope 4 in this order. Since water to allow intake of a foaming agent may be necessary, it is also possible, in consideration of the above case, to store the water in a storage area of the blister pack 231 so that the subject can take in the capsule endoscope 4, a foaming agent, and the water in this order. Depending on storage or transportation characteristics, only a liquid and foaming agent, or a portion thereof may be stored in the storage areas of the blister pack 231.

The capsule endoscope 4 may contain a first magnetic body (permanent magnet) that can be guided from outside the subject 2 to cause the capsule endoscope 4, for example, to move in the horizontal direction or to swing on the spot by adding a magnetic field by a magnetic body (permanent magnet or electromagnet) to the capsule endoscope 4 from outside the subject. Here, if the magnetic body outside the subject 2 to be used for guidance is a permanent magnet, a new storage area is formed at the end of the blister pack 231 to store, like other intake materials, the permanent magnet therein to define the order of using the permanent magnet. Then, it is also possible to allow intake or acquisition by the subject, for example, in the order of a liquid, the capsule endoscope 4, and a permanent magnet, in the order of the capsule endoscope 4, a foaming agent, and a permanent magnet, in the order of a liquid, the capsule endoscope 4, a foaming agent and a permanent magnet, or in the order of the capsule endoscope 4, a foaming agent, water and a permanent magnet. In this case, the blister pack 231 is preferably constructed of a magnetic closed circuit to block a magnetic field of the stored magnet.

Further, if the position of a magnet outside the subject is indicated by using a template, a new storage area to store the template is formed at the first position of the blister pack 231 to store, like other intake materials, the template therein. Then, it is also possible to allow intake or acquisition by the subject, for example, in the order of a template, a liquid, the capsule endoscope 4, and a permanent magnet, in the order of a template, the capsule endoscope 4, a foaming agent, and a permanent magnet, in the order of a template, a liquid, the capsule endoscope 4, a foaming agent and a permanent magnet, or in the order of a template, the capsule endoscope 4, a foaming agent, water and a permanent magnet.

The subject 2 may also take in a remover (such as Gascon, dimethylpolysiloxane, pronase, proctase and sodium hydrogen carbonate) to remove foams by a foaming agent or mucus inside the stomach, or mucus itself before taking in a liquid. In this case, a new storage area to store a remover may be formed at the first position of the blister pack 231 or the remover may be caused to mix with a liquid stored in a storage area. Then, it is also possible to allow intake by the subject 2, for example, in the order of a remover, a liquid, and the capsule endoscope 4, in the order of a remover, the capsule endoscope 4, and a foaming agent, in the order of a remover, a liquid, the capsule endoscope 4, and a foaming agent, or in the order of a remover, the capsule endoscope 4, a foaming agent, and a liquid. In addition, antispastics (such as a peppermint solution, oxethazaine, scopolia extract, and timepidium bromide) may be fed in specific order to enable the subject 2 to take in such antispastics.

Fourteenth Modification

Figure 55:
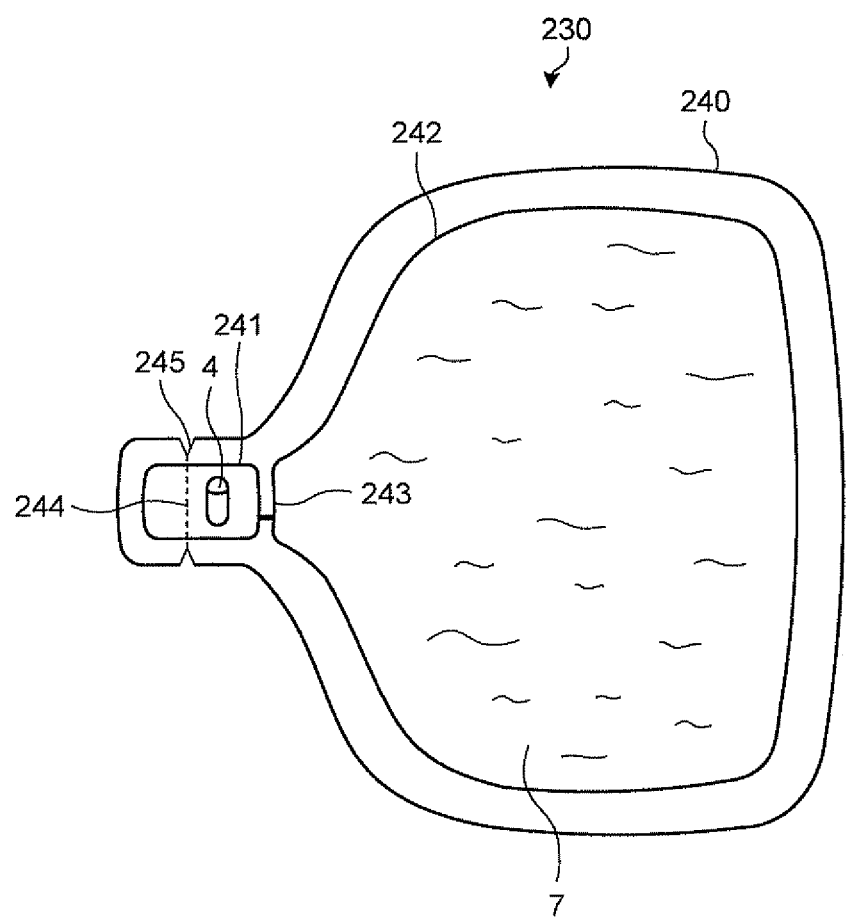
FIG. 55 is a front view showing the configuration of a fourteenth modification of the capsule storing device.

FIG. 55 is a front view showing the configuration of a fourteenth modification of the capsule storing device 230 according to the ninth embodiment shown in FIG. 52. In FIG. 55, the capsule storing device 230 according to the fourteenth modification comprises a package 240 as a storage unit having storage areas 241, 242 storing the capsule endoscope 4 and the liquid 7 respectively and a partition wall 243 provided between the storage areas 241, 242 to penetrably separate the storage areas 241, 242. The package 240 is formed of, for example, a resin material in an approximately cylindrical bag shape and has the two-part storage areas 241, 242 provided therein. The fourteenth modification is intended to store each intake material separately in each storage area and thus, defined as a modification of the ninth embodiment.

The storage areas 241, 242 are formed in an approximately cylindrical shape to store the capsule endoscope 4 and the liquid 7 separately. For example, the capsule endoscope 4 is stored in the storage area 241 and the liquid 7 used by the subject 2 to swallow the capsule endoscope 4 is stored in the storage area 242. The partition wall 243 to separate the storage areas 241, 242 is allocated between the storage areas 241, 242. The partition wall 243 acts to separate the both storage areas 241, 242 against pressure from the storage area 241 direction (pressure applied from the storage area 241 side) and acts to allow penetration between the both storage areas 241, 242 against pressure from the storage area 242 direction (pressure applied from the storage area 242 side) in the same manner, for example, like a check valve.

A mouth 244 is provided at one end of the storage area 241 to allow intake materials inside the storage areas 241, 242 to discharge. The mouth 244 is formed normally to block the storage area 241 from outside and formed in such a way that the storage area 241 and the outside can be made to communicate when the subject 2 cuts a portion of the mouth 244 before the capsule endoscope 4 being swallowed. A slit 245 may also be provided in the package 240 near the mouth 244 so that a portion of the mouth 244 can easily be cut.

In the fourteenth modification, the subject first cuts a portion of the mouth 244, takes out the capsule endoscope 4 from the storage area 241 and then, applies pressure to the package 240 on an outer circumference of the storage area 242 to cause the liquid in the storage area 242 to discharge into the mouth of the subject.

In the fourteenth modification, as described above, a liquid and the capsule endoscope 4 are stored separately in the storage areas and a portion of the mouth 244 is cut to allow feeding of each intake material to the subject 2 in specific order and therefore, like the ninth embodiment, the subject 2 is enabled to take in a plurality of intake materials needed for examination correctly and easily in specific order, and deformation and deterioration of individual intake materials can be prevented.

The fourteenth modification is described by taking the capsule endoscope 4 as an example, but instead of the capsule endoscope 4, for example, a solid or powder foaming agent may also be stored in the storage area 241. In this case, the foaming agent deforms or deteriorates due to moisture content and thus, deformation and deterioration of the foaming agent before being swallowed by the subject 2 can be prevented by storing the foaming agent separately from the liquid. Then, it is also possible, after the capsule endoscope 4 being swallowed, to enable the subject 2 to take in the foaming agent and water in this order.

Tenth Embodiment

Figure 56:
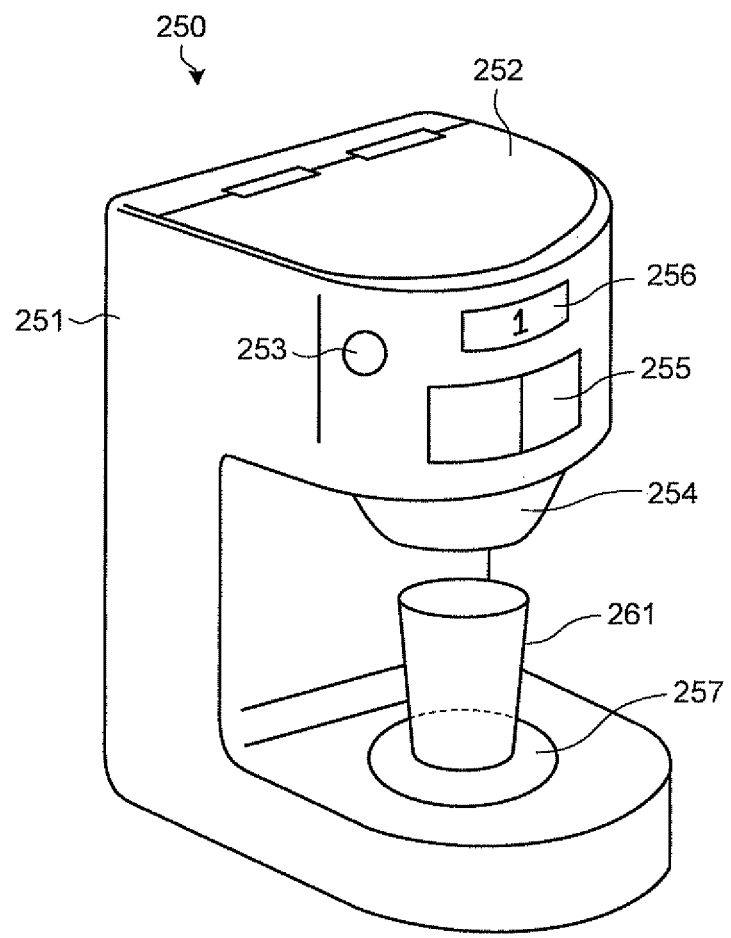
FIG. 56 is a perspective view showing the configuration of a capsule storing device according to a tenth embodiment of the present invention.
Figure 57:
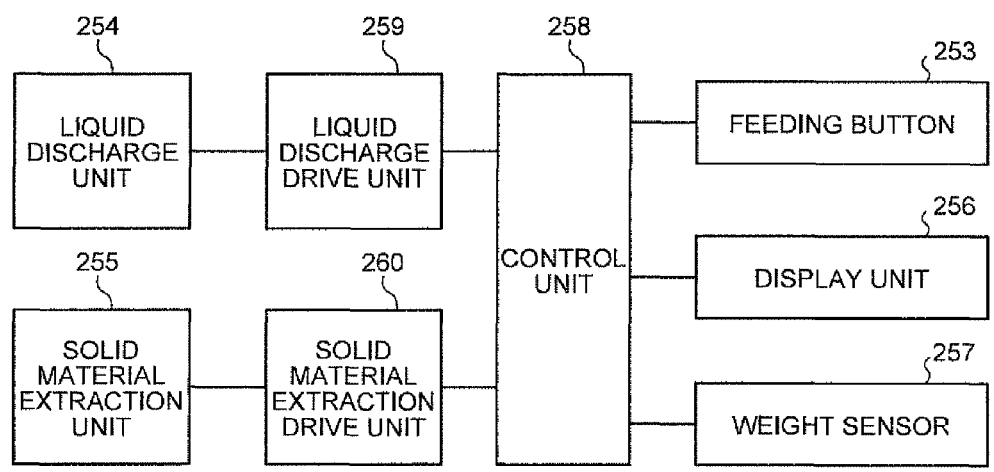
FIG. 57 is a block diagram showing the internal configuration of a drive controlling system of the capsule storing device shown in FIG. 56.

FIG. 56 is a perspective view showing the configuration of a capsule storing device 250 according to a tenth embodiment for storing intake materials to be taken in by a subject, and FIG. 57 is a block diagram showing the internal configuration of a drive controlling system of the capsule storing device 250 shown in FIG. 56. In the tenth embodiment, in contrast to the above-described packages or blister packs, a plurality of intake materials to be taken in by the subject is fed in order mechanically and actively. In FIG. 56 and FIG. 57, the capsule storing device 250 comprises an enclosure main body 251 as a storage unit whose side view is in a one-side open square shape, a covering device 252 covering an upper surface of an opening of the enclosure main body 251, a feeding button 253 for instructing feeding of intake material, a liquid discharge unit 254 provided in an upper part of the enclosure main body 251 to serve as a storage area for storing and discharging first and second liquids, a solid material extraction unit 255 provided in the upper part of the enclosure main body 251 to serve as a storage area for storing, among the capsule endoscope 4 and intake materials, the capsule endoscope 4 and solid materials such as a foaming agent and from which the capsule endoscope 4 and solid materials are extracted, a display unit 256 provided in the upper part of the enclosure main body 251 to indicate the examination order or specific acquisition order of a plurality of intake materials, and a weight sensor 257 provided in an lower part of the enclosure main body 251 to detect a container placed such as a cup 261.

The liquid discharge unit 254 is disposed at the underside of the upper part of the enclosure main body 251 and discharges the first and second liquids stored therein in the direction of the weight sensor 257 below under drive control of a liquid discharge drive unit 259. In the liquid discharge unit 254, the first and second liquids are stored in separate storage areas and discharged separately based on specific order.

The solid material extraction unit 255 is disposed on the side surface of the upper part of the enclosure main body 251 and causes the capsule endoscope 4 and a foaming agent to be transported in a lateral direction of the enclosure main body 251 under drive control of a solid material extraction drive unit 260 so that the subject 2 can extract the capsule endoscope 4 and the foaming agent stored therein. The solid material extraction unit 255 may be constructed so that both intake materials, the capsule endoscope 4 and the foaming agent, are transported simultaneously or separately. These intake materials can be replenished by replenishing the liquid discharge unit 254 and the solid material extraction unit 255 with intake materials from above after opening the covering device 252 covering the upper surface of the opening of the enclosure main body 251.

Figure 58:
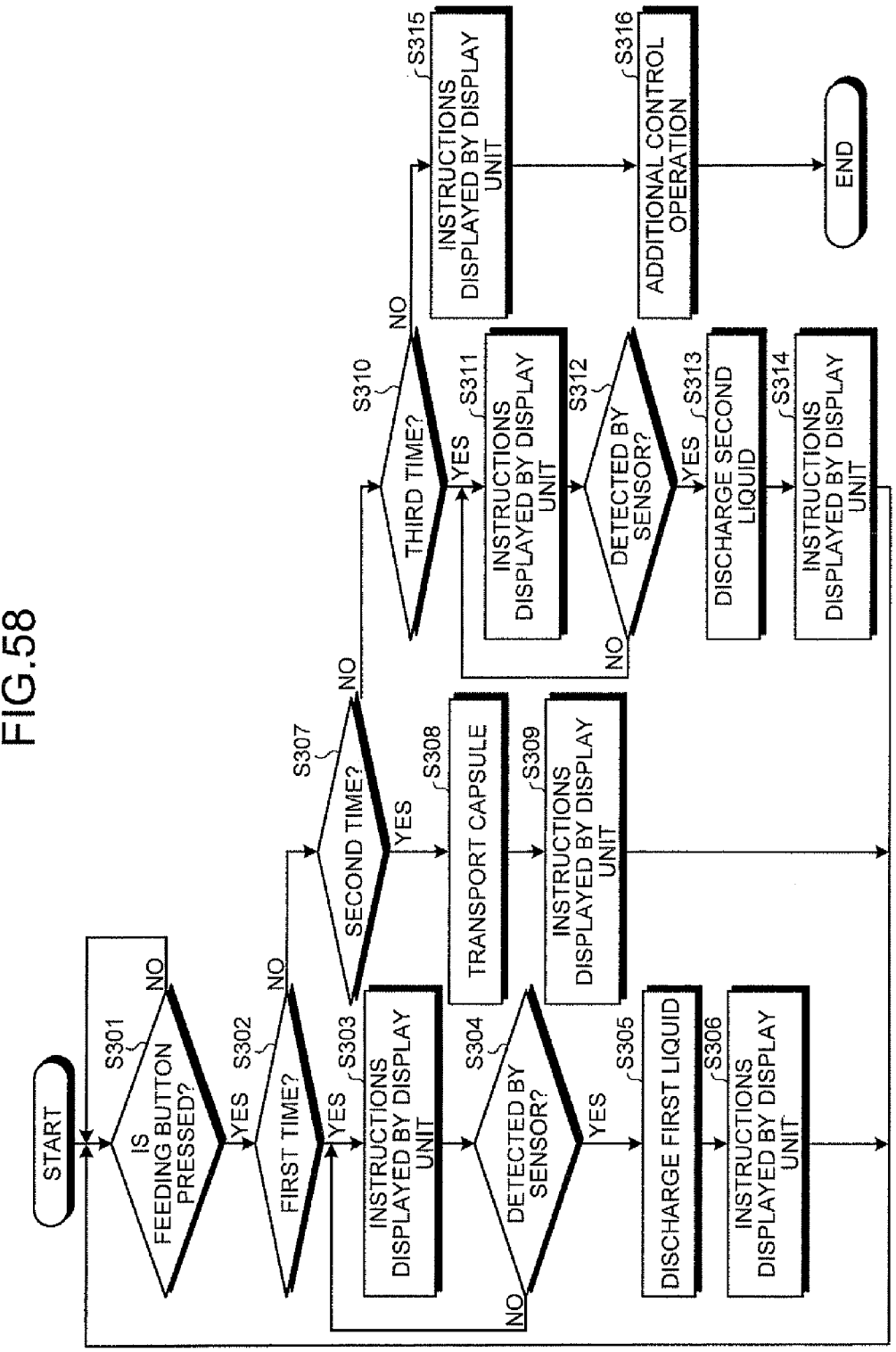
FIG. 58 is a flow chart illustrating operations of the drive controlling system.

The display unit 256 consists of, for example, a display unit of LCD and displays the next step to be taken by the subject 2 when the feeding button 253 is pressed. The weight sensor 257 detects the weight of the placed cup 261 and when the cup 261 reaches a certain weight with a flow of liquid, notifies a control unit 258 of detection information that the cup 261 has reached a certain weight. The control unit 258 performs display and drive control of the display unit 256, the liquid discharge drive unit 259r and the solid material extraction drive unit 260 in accordance with instruction information from the feeding button 253 and detection information from the weight sensor 257. Operations of the display and drive control by the control unit 258 will be described below using a flow chart in FIG. 58.

First, when the subject 2 to be examined presses the feeding button 253 (step S301, S302), the control unit 258 causes the display unit 256 under display control to display "1" indicating specific order and a message "Liquid will come out. Please place a cup." in a screen of the display unit 256 (step S303). When the cup 261 is placed on the weight sensor 257, the weight sensor 257 detects that a cup has been placed (step S304) and the control unit 258 causes the liquid discharge drive unit 259 under drive control to discharge the first liquid 7 from the liquid discharge unit 254 in accordance with a detection signal from the weight sensor 257 (step S305). The capsule storing device 250 has an input unit of information, and the control unit 258 determines the type of liquid and an intake required for the examination based on subject information (such as the physique of the subject, stomach size, and examination conditions on that day) input through the input unit from outside in advance or transferred from a hospital-wide network or the like and causes the liquid discharge drive unit 259 to feed a liquid of the determined type and intake.

When the discharged first liquid 7 gathers in the cup 261 and the weight sensor 257 detects a certain weight, the control unit 258 causes the liquid discharge drive unit 254 to stop discharging of the first liquid 7 from the liquid discharge unit 254 and the display unit 256 to display "2" indicating specific order and a message "Please drink the liquid. When you finish drinking, please press the feeding button." in the screen of the display unit 256 (step S306). The subject 2 drinks the first liquid 7 according to this display and presses the feeding button 253 (step S307, S307).

When the feeding button 253 is pressed again, the control unit 258 causes the solid material extraction drive unit 260 under drive control to transport the capsule endoscope 4 from the solid material extraction unit 255 out of the capsule storing device 250 (step S308). Then, the control unit 258 causes the display unit 256 to display "3" indicating specific order and a message "Please swallow the capsule. When you finish swallowing, please press the feeding button." in the screen of the display unit 256 (step S309). The capsule endoscope 4 is already activated when being transported from the solid material extraction unit 255. The capsule storing device 250 has an electromagnet for capsule activation provided in the solid material extraction unit 255 and the capsule endoscope 4 is caused to activate by turning on a magnetic switch inside the capsule endoscope 4 by causing the electromagnet to generate a magnetic field.

Next, when the feeding button 253 is pressed (step S301, S310), the control unit 258 causes the display unit 256 to display "4" indicating specific order and a message "Liquid will come out. Please place a cup." in the screen of the display unit 256 (step S311). When the cup 261 is placed on the weight sensor 257 (step S312), the control unit 258 causes the liquid discharge drive unit 259 to discharge the second liquid 8 from the liquid discharge unit 254 in accordance with a detection signal from the weight sensor 257 (step S313). When a certain amount of the second liquid 8 gathers in the cup 261, the control unit 258 causes the liquid discharge drive unit 259 to stop discharging of the second liquid 8 from the liquid discharge unit 254 and the display unit 256 to display "5" indicating specific order and a message "Please drink the liquid." in the screen of the display unit 256 (step S314). The subject 2 drinks the second liquid 8 according to this display and presses the feeding button 253 (step S301).

Then, the capsule storing device 250 continues to provide examination instructions to make the subject 2 additionally drink the first liquid 7 to control the floating position of the capsule endoscope 4 inside the stomach 3. In this case, the control unit 258 causes the display unit 256 to display information of the examination instructions. That is, the examination instructions are provided in the form of message display such as "Please additionally drink the first liquid." in the screen of the display unit 256 after the feeding button 253 being pressed (step S315) and the control unit 258 performs an additional control operation (step S316).

In the tenth embodiment, like the eighth embodiment, the stomach can be caused to extend by drinking a liquid and therefore, sufficient space can be secured inside organs required for observation by the capsule endoscope 4, the inner wall of organs can be imaged more closely, and observations inside the stomach can be made without omission. The capsule endoscope 4 floats at an interfacial boundary (a liquid-liquid interfacial boundary by the first and second liquids or a gas-liquid interfacial boundary by the first liquid and a gas) rocking randomly only by changing the position of the interfacial boundary inside the stomach in combination with posture changes of the subject 2 itself. With the capsule endoscope 4 rocking randomly, imaging regions inside the stomach to be imaged by the capsule endoscope 4 can be caused to change and thus, inside the stomach can be observed more thoroughly without omission. As a result, a plurality of images picked up randomly can be combined based on correlations of between images after an examination so that it becomes possible to create an overall image inside the stomach and when the image is presented to a physician or the like, to make an efficient diagnosis.

In the tenth embodiment, as described above, intake materials are mechanically and actively fed based on specific order and therefore, the subject can be enabled to take in a plurality of intake materials required for an examination correctly and easily in specific order. Since the order of intake becomes correct, as described above, anybody can deal with the capsule storing device easily so that the examination is made easier. Accordingly, a probability that the subject 2 takes in intake materials in incorrect order is reduced and examinations advance smoothly so that prevention of incorrect examinations and more efficient examination times can be promoted. Also in the tenth embodiment, the order of feeding intake materials and intakes can arbitrarily adjusted in accordance with the physique of the subject and examination purposes and therefore, flexibility in feeding intake materials is improved and examination can be made with still higher precision. Moreover, examinations of a plurality of subjects can be dealt with by one capsule storing device, leading to more efficient examinations.

In the capsule storing device 250 according to the tenth embodiment, for example, a function to mix a plurality of liquids or a liquid and a solid such as powder inside the capsule storing device 250 for feeding may be provided. With this mixing function provided, concentrations of liquid can be adjusted and optimal liquids fitted to each subject can be fed and thus, examinations can be made with still higher precision. Further, the temperature of liquid to be fed can be adjusted. Accordingly, the specific gravity of liquid can be adjusted by concentrations or the temperature to control the floating state of the capsule endoscope in the liquid. If the liquid is water, for example, the specific gravity increases as the temperature drops, making the capsule endoscope more likely to float in liquids. The specific gravity of liquid taken in can be caused to change by first drinking cold (for example, at temperature of 10° C. or so) water and then gradually raising the temperature thereof by body temperature.

When the capsule storing device 250 is replenished with liquids, the capsule storing device 250 may be constructed so that intake materials to be replenished that are stored in a package like in the eighth and ninth embodiments can be set to the capsule storing device 250 to allow replenishment of intake materials that need to be taken in by the subject at a time.

Further, the capsule storing device 250 according to the tenth embodiment may be constructed so that necessary intake materials are fed in accordance with a pass time in the body of the capsule endoscope 4 (an example of the capsule medical apparatus) taken in by the subject 2 or other states (the position, posture, or movement speed of the capsule endoscope 4 or a state of observation images or illumination emission) concerning the capsule endoscope 4. In this case, the capsule storing device 250 comprises a state detector for detecting the pass time in the body of such a capsule medical apparatus or other states concerning the capsule endoscope 4, and determines a state (such as the above-described pass time in the body, position and the like) of the capsule medical apparatus based on the state detector.

Figure 59:
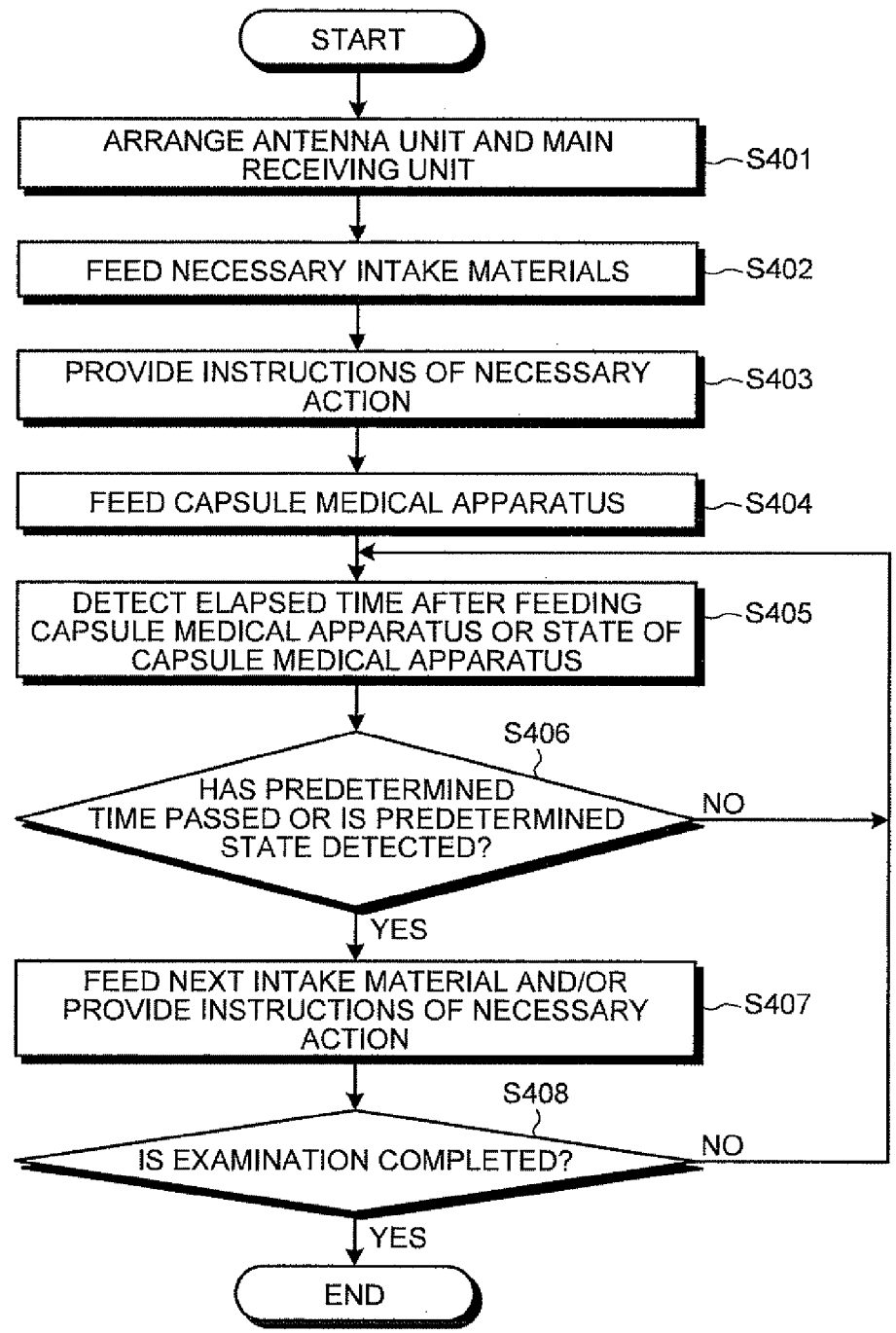
FIG. 59 is an outline flow chart showing another procedure for the feeding method of an intake material using the capsule storing device according to the tenth embodiment of the present invention.

FIG. 59 is an outline flow chart showing another procedure for the feeding method of an intake material using the capsule storing device according to the tenth embodiment of the present invention. As shown in FIG. 59, before feeding intake materials to be fed to the subject 2, the antenna unit 6c having the antennas A1 to An for reception for receiving a radio signal from the capsule endoscope 4 is arranged at a predetermined position of the subject 2 and also the main receiving unit 6d is arranged near the subject 2 (step S401).

Next, the feeding button 253 of the capsule storing device 250 is operated to feed intake materials currently needed for the subject 2 (step S402). In this case, in response to this operation of the feeding button 253, the capsule storing device 250 feeds an intake material such as a cleaning agent (remover) to clean digestive tracts of the subject 2. More specifically, such an intake material is discharged from the liquid discharge unit 254 into the cup 261 before being fed to the subject 2.

Subsequently, the capsule storing device 250 provides instructions of action necessary for the subject 2 when such an intake material is fed (step S403). At step S403, for example, the capsule storing device 250 provides instructions to the subject 2 to take in the intake material such as a remover fed at step S402 before a capsule medical apparatus such as the capsule endoscope 4 through, for example, instruction display by the display unit 256. In this case, the capsule storing device 250 may provide instructions to the subject 2 taking in such an intake material to change the posture to one appropriate for intake of the intake material if necessary.

Subsequently, the feeding button 253 of the capsule storing device 250 is operated again to feed a capsule medical apparatus the subject 2 is made to take in (step S404). In this case, in response to this operation of the feeding button 253, the capsule storing device 250 feeds the capsule medical apparatus (part of intake materials) such as the capsule endoscope 4 the subject 2 is made to take in from the solid material extraction unit 255 to the subject 2. The capsule medical apparatus fed by the capsule storing device 250 is taken in by the subject 2.

Next, the capsule storing device 250 detects an elapsed time after the capsule medical apparatus being fed (or after the capsule medical apparatus being taken in by the subject 2) or a state of the capsule medical apparatus inside the subject 2 using the state detector (not shown) or the like (step S405). In this case, the capsule storing device 250 (more specifically, the state detector) detects such an elapsed time or a state (the position, posture, or movement speed of the capsule medical apparatus or a state of observation images or illumination emission) concerning the capsule medical apparatus taken in by the subject 2.

If such an elapsed time or state of the capsule medical apparatus detected by the capsule storing device 250 is a predetermined elapsed time or state (step S406, Yes), the capsule storing device 250 feeds the next intake material necessary for the subject 2 and/or provides instructions of action necessary for the subject 2 (step S407). In this case, the capsule storing device 250 feeds the next intake material (for example, a liquid such as water) the subject 2 is made to take in next in accordance with a detection result of the elapsed time or state of the capsule medical apparatus at step S405. The capsule storing device 250 also provides instructions of action (such as intake of the fed intake material or a change of posture to one appropriate for intake of the intake material) necessary for the subject 2 by display instruction information in the display unit 256 if necessary.

If such an elapsed time or state of the capsule medical apparatus detected by the capsule storing device 250 is not a predetermined elapsed time or state (step S406, No), the capsule storing device 250 returns to the above step S405 to repeat the processing procedures at step S405 and thereafter.

Then, if the examination of the subject 2 (that is, image pickup or observation of regions to be examined inside the subject 2) is not completed (step S408, No), the capsule storing device 250 returns to the above step S405 to repeat the processing procedures at step S405 and thereafter. If, on the other hand, the examination of the subject 2 is completed (step S408, Yes), the capsule storing device 250 terminates the present processing to feed intake materials of the subject 2.

A concrete example of feeding of intake materials depending on an elapsed time inside the body of the capsule endoscope 4 will be shown below. The capsule storing device 250 feeds a cleaning agent (remover) to clean digestive tracts before the capsule endoscope 4 to have the fed cleaning agent taken in by the subject 2. To make the cleaning of digestive tracts more reliable, the capsule storing device 250 may provide instructions to the subject 2 to change the posture by means of instruction display in the display unit 256 if necessary.

The capsule storing device 250 feeds the capsule endoscope 4 when a predetermined time passes after feeding the cleaning agent or providing instructions to change the posture. The fed capsule endoscope 4 is taken in by the subject 2. The capsule storing device 250 stores an intake time of the capsule endoscope 4 (or a feeding time of the capsule endoscope 4). The capsule storing device 250 feeds a liquid after, for example, five minutes from the time (the intake time or feeding time) and prompts the subject or the like to take in the fed liquid by means of instruction display by the display unit 256 or the like.

Further, the capsule storing device 250 feeds an intake material such as another liquid, a foaming agent, a remover, or an antispastic each time a predetermined time passes if necessary, and provides instructions to take in the fed intake material by means of instruction display by the display unit 256 or the like. The capsule storing device 250 may also provide instructions to change the posture after taking in (or feeding) each intake material or the like.

Next, a concrete example of feeding intake materials depending on the region reached in the body by the capsule endoscope 4 (the position of the capsule endoscope 4) and the state of the capsule endoscope 4 will be shown below. The capsule storing device 250 first feeds the capsule endoscope 4 with a specific gravity that floats the capsule endoscope 4 in a liquid. The fed capsule endoscope 4 moves through digestive tracts after being taken in by the subject 2.

After the capsule endoscope 4 being taken in, the capsule storing device 250 confirms that the capsule endoscope 4 has reached the stomach of the subject 2 by means of a position detector (an example of the above state detector) and then, feeds a certain liquid (for example, 200 ml of water), which is the next intake material the subject 2 is made to take in. Based on images acquired by the capsule endoscope 4, the position detector of the capsule storing device 250 determines the distance between the capsule endoscope 4 and the wall of stomach from brightness of images or the like. If, as a result of state determination processing by the position detector, the distance is insufficient (too far away), suitable observations inside the stomach cannot be made and the capsule storing device 250 further feeds 100 ml of water based on the result of state determination processing. Additional feeding processing of water by the capsule storing device 250 continues until the position detector determines that the distance between the capsule endoscope 4 and the wall of stomach has become suitable. As a result, a suitable amount of water for the subject 2 can be fed by the capsule storing device 250.

The capsule storing device 250 may also feed a foaming agent to promote extension of the stomach, if necessary. Further, the capsule storing device 250 may provide instructions to change the posture necessary for stomach observation or the like by means of instruction display by the display unit 256 or the like.

If the subject 2 should be observed closely, the capsule storing device 250 feeds a magnet (a permanent magnet or electromagnet) to guide the capsule endoscope 4 inserted into the body of the subject from outside the body. The capsule endoscope 4 inside the body is guided by the fed magnet and also picks up images inside the organ successively and, as a result, close observation inside the body of the subject 2 can be made.

If, after the stomach is observed, arrival of the capsule endoscope 4 at the duodenum is confirmed by the position detector, the capsule storing device 250 feeds 1000 ml of a liquid (such as nonabsorbable irrigation water for intestinal lavage) to promote advancement of the capsule endoscope 4. In this case, the capsule storing device 250 may also provide a drug such as a purgative. Then, if the capsule storing device 250 can confirm that the capsule endoscope 4 inside the body is positioned at a boundary between the jejunum and the ileum after such a liquid or purgative being taken in, the capsule storing device 250 further feeds a liquid or drug for promoting advancement. The capsule storing device 250 may comprise a speed detector (an example of the state detector) for detecting the movement speed of the capsule endoscope 4 inside the body so that a liquid or purgative for promoting advancement is further fed in accordance with the movement speed of the capsule endoscope 4 detected by the speed detector, that is, when the movement speed slows down.

Subsequently, if arrival of the capsule endoscope 4 inside the body at the large intestine is detected by the position detector, the capsule storing device 250 feeds an intake material (such as a liquid or purgative) for promoting advancement and also provides instructions to the subject 2 to take a lie position by means of instruction display by the display unit 256 or the like. In this case, the capsule storing device 250 may also provide instructions to change the posture of the subject 2 in accordance with the region (such as the ascending colon, transverse colon, descending colon, and sigmoid colon) of the large intestine in which the capsule endoscope 4 is positioned. Lastly, the capsule storing device 250 feeds a purgative (suppository) for promoting elimination of the capsule endoscope 4 inside the large intestine.

The position detector for detecting the position of the capsule endoscope 4 may be one that determines the position of the capsule endoscope 4 based on features or the amount of change of images picked up by the capsule endoscope 4, one that detects the position or posture of the capsule endoscope 4 by detecting a magnetic field generated by a magnetic field generator (such as a permanent magnet, coil, and electromagnet) mounted on the capsule endoscope 4 from outside the body, or one that detects the position of the capsule endoscope 4 based on received electric-field strength when radio waves sent from the capsule endoscope 4 are received outside the body. Also, the position detector may be arranged outside the body of the subject 2 without being contained in the capsule storing device and information communication between the position detector and the capsule storing device may be performed by wire or by radio. From what is described above, action such as feeding of necessary intake materials and posture change instructions is taken at necessary timing and, as a result, examinations inside the body of the subject 2 can be made more reliably.

Fifteenth Modification

Figure 60:
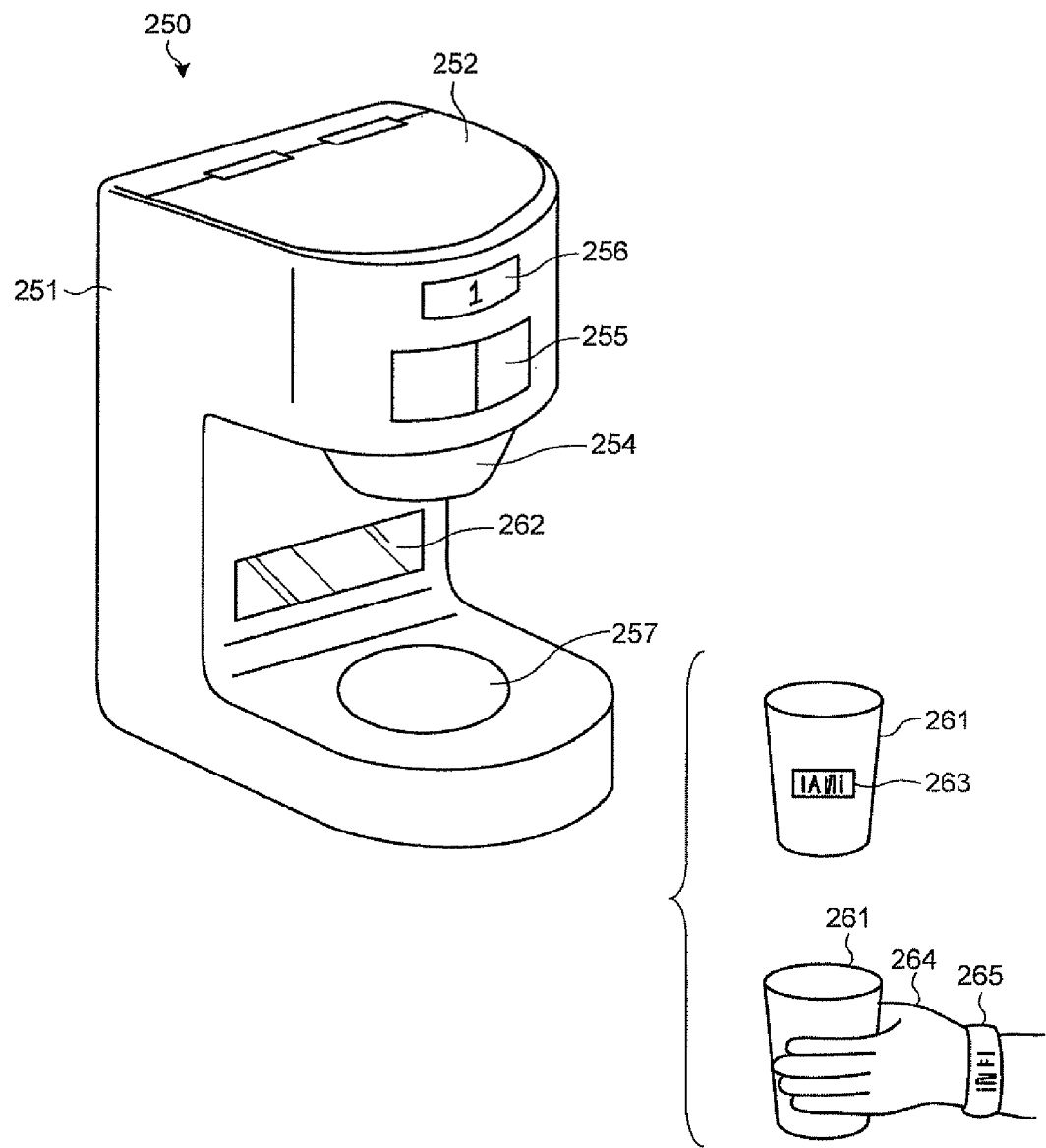
FIG. 60 is a perspective view showing the configuration of a fifteenth modification of the capsule storing device.

FIG. 60 is a perspective view showing the configuration of a fifteenth modification of the capsule storing device 250 according to the tenth embodiment shown in FIG. 56. In the fifteenth modification, an ID reader 262 for optically reading identification information is provided on the side surface of the enclosure main body 251 and the capsule storing device 250 (the control unit 258) determines what kind of examination the subject 2 will take and in which order to feed liquids, the capsule endoscope 4, and a foaming agent to the subject 2 by reading ID information (ID information such as black and white pattern information and character information) 263, 265 affixed to wrist bands attached to, for example, the cup 261 and an arm 264 of the subject 2. That is, the control unit 258 is caused to store identification information for identifying the subject 2 and examination as ID information and also to store the order of examination based on the ID information and when the relevant ID information is read by the ID reader 262, the control unit 258 controls the liquid discharge unit 254, the solid material extraction unit 255, and the display unit 256 based on storage content to feed a plurality of intake materials in specific order. Amounts of intake materials can be fed after making adjustments fitting to the subject or examination. Other components in the fifteenth modification are the same as those in the tenth embodiment and, for example, the feeding button 253 may not be used or may be used in combination with ID reading.

In the fifteenth modification, as described above, ID information of the subject is detected by using an ID reader and feeding of intake materials in specific order in accordance with the ID information is enabled and therefore, like the tenth embodiment, the subject can be enabled to take in a plurality of intake materials required for an examination correctly and easily in specific order, and also the order in which intake materials are fed can arbitrarily be set and therefore, the order in which liquids and a capsule endoscope are fed can be changed depending on examination content, improving flexibility to feed intake materials.

Sixteenth Modification

Figure 61:
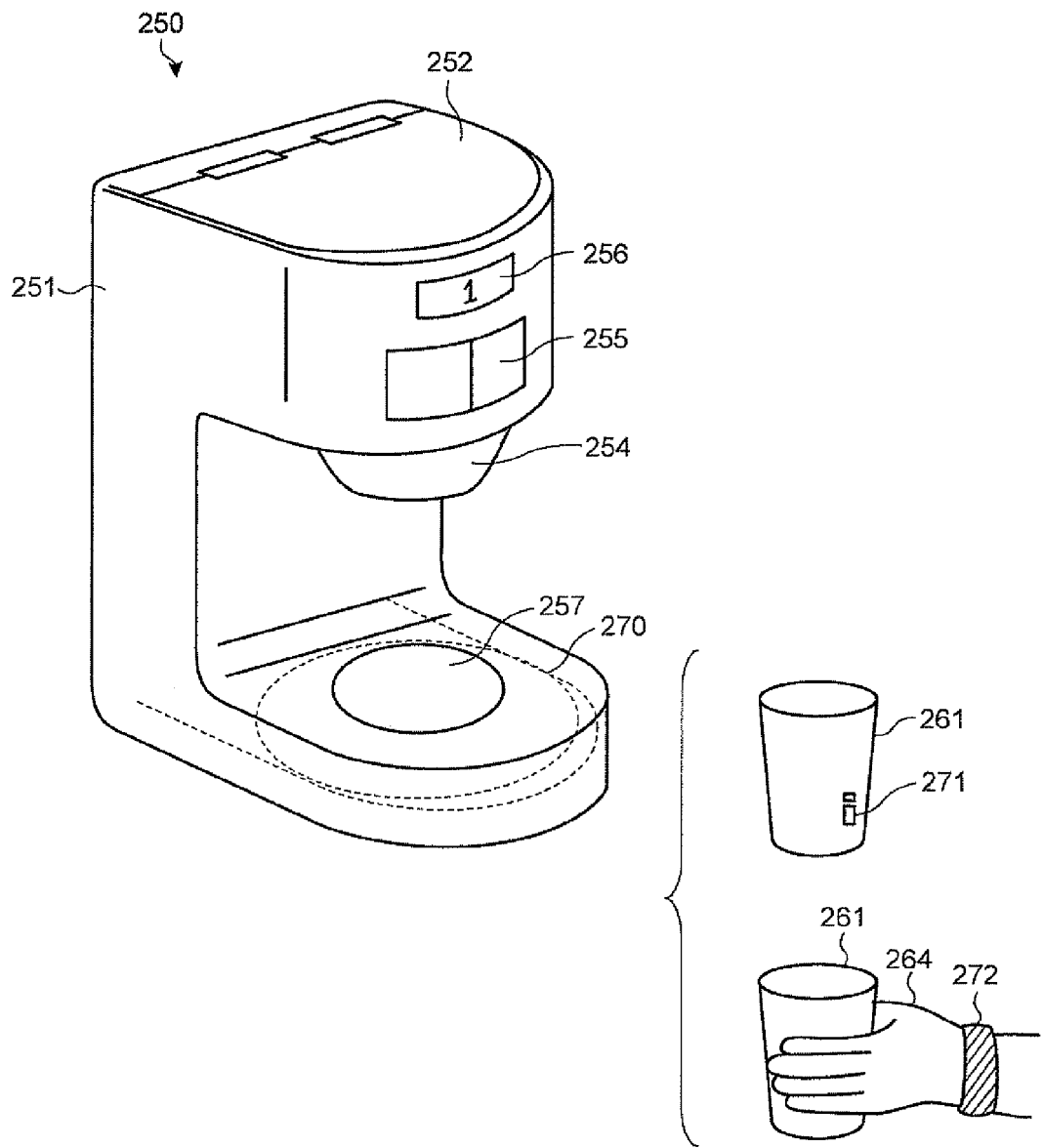
FIG. 61 is a perspective view showing the configuration of a sixteenth modification of the capsule storing device.

FIG. 61 is a perspective view showing the configuration of a sixteenth modification of the capsule storing device according to the tenth embodiment shown in FIG. 56. In the sixteenth modification, instead of the optical ID reader, a magnetic ID reader 270 for reading ID information from wireless ID tags by means of radio waves or electromagnetic waves is provided in the capsule storing device 250. Also in this case, the capsule storing device 250 (the control unit 258) determines what kind of examination the subject 2 will take and in which order to feed liquids, the capsule endoscope 4, and a foaming agent to the subject 2 by reading ID information from wireless ID tags 271, 272 affixed to wrist bands attached to, for example, the cup 261 and the arm 264 of the subject 2.

In the sixteenth modification, as described above, ID information of the subject is detected by using an ID reader and feeding of intake materials in specific order in accordance with the ID information is enabled and therefore, like the tenth embodiment, the subject can be enabled to take in a plurality of intake materials required for an examination correctly and easily in specific order, and also the order in which intake materials are fed and amounts of intake materials can arbitrarily be set and therefore, the order in which liquids and a capsule endoscope are fed can be changed depending on examination content, improving flexibility to feed intake materials.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An intra-subject observation system, comprising:
   a first liquid inserted into a desired organ of a subject;
   a second liquid inserted into the organ to be in contact with the first liquid via an interfacial boundary without being mixed with the first liquid due to a specific gravity lighter than that of the first liquid; and
   a capsule medical apparatus inserted into the organ with an intermediate specific gravity between the specific gravity of the first liquid and that of the second liquid to acquire intra-subject information, which is output out of the subject by radio,
   wherein the first liquid, second liquid, and capsule medical apparatus are independently inserted into the organ.

2. The intra-subject observation system according to claim 1, wherein the capsule medical apparatus is a capsule endoscope for picking up intra-subject images.

3. The intra-subject observation system according to claim 2, wherein the capsule endoscope is a monocular capsule endoscope capable of imaging only in a front-end direction, a perspective direction on a front-end side, or a circumferential direction on the front-end side.

4. The intra-subject observation system according to claim 3, wherein the capsule endoscope is a capsule endoscope in which a center of gravity is decentered by changing a balance of weight in a front-back direction.

5. The intra-subject observation system according to claim 4, wherein the capsule endoscope is a capsule endoscope in which the front-end side is relatively heavier.

6. The intra-subject observation system according to claim 4, wherein the capsule endoscope is a capsule endoscope in which the front-end side is relatively lighter.

7. The intra-subject observation system according to claim 2, wherein the capsule endoscope is a binocular capsule endoscope capable of imaging in a front-end direction and a back-end direction.

8. The intra-subject observation system according to claim 7, wherein the capsule endoscope is a capsule endoscope in which a center of gravity is decentered by changing a balance of weight in a front-back direction.

9. The intra-subject observation system according to claim 8, wherein the capsule endoscope is a capsule endoscope in which the front-end side is relatively heavier.

10. The intra-subject observation system according to claim 8, wherein the capsule endoscope is a capsule endoscope in which the front-end side is relatively lighter.

11. The intra-subject observation system according to claim 2, wherein the capsule endoscope is a capsule endoscope having a wider-angle imaging optical system.

12. The intra-subject observation system according to claim 11, wherein the capsule endoscope is a capsule endoscope in which a center of gravity is decentered by changing a balance of weight in a front-back direction.

13. The intra-subject observation system according to claim 12, wherein the capsule endoscope is a capsule endoscope in which the front-end side is relatively heavier.

14. The intra-subject observation system according to claim 12, wherein the capsule endoscope is a capsule endoscope in which the front-end side is relatively lighter.

15. The intra-subject observation system according to claim 2, wherein the first liquid and the second liquid are transparent to light of wavelengths of the imaging optical system of the capsule endoscope.

16. The intra-subject observation system according to claim 1, wherein the first liquid is drinking water and the second liquid is edible oil.

17. The intra-subject observation system according to claim 1, wherein the first liquid and/or the second liquid is changeable in an amount of insertion into the organ.

18. The intra-subject observation system according to claim 17, wherein the amount of insertion of the first liquid into the organ is gradually increased.

19. The intra-subject observation system according to claim 1, wherein the desired organ of the subject is a stomach.

20. The intra-subject observation system according to claim 19, further comprising a receiving apparatus arranged outside the subject to receive intra-subject information transmitted by radio from the capsule medical apparatus inside the organ.

21. The intra-subject observation system according to claim 20, further comprising a posture change apparatus for changing a posture of the subject having the first liquid, the second liquid, and the capsule medical apparatus inserted into the desired organ.

22. The intra-subject observation system according to claim 20, comprising a detector for detecting a floating position and/or floating posture of the capsule medical apparatus at an interfacial boundary.

23. The intra-subject observation system according to claim 22, comprising a combination processing unit for combining a plurality of pieces of intra-subject information acquired by the capsule medical apparatus by referring to information of the floating position and/or floating posture of the capsule medical apparatus detected by the detector when acquiring the intra-subject information.

24. The intra-subject observation system according to claim 20, wherein the detector is contained in the capsule medical apparatus.

25. The intra-subject observation method according to claim 20, wherein a binocular capsule endoscope capable of imaging in a front-end direction and a back-end direction is used as the capsule endoscope.

26. An intra-subject observation method comprising:
    inserting a first liquid into a desired organ of a subject;
    inserting a second liquid, which does not mix with the first liquid due to a specific gravity lighter than that of the first liquid, into the organ;
    inserting a capsule medical apparatus, which has an intermediate specific gravity between the specific gravity of the first liquid and that of the second liquid, into the organ; and
    acquiring intra-subject information by the capsule medical apparatus inserted into the organ and floating at an interfacial boundary between the first liquid and the second liquid to output the intra-subject information out of the subject by radio.

27. The intra-subject observation method according to claim 26, wherein a capsule endoscope for picking up intra-subject images is used as the capsule medical apparatus.

28. The intra-subject observation method according to claim 27, wherein a monocular capsule endoscope capable of imaging only in a front-end direction, a perspective direction on a front-end side, or a circumferential direction on the front-end side is used as the capsule endoscope.

29. The intra-subject observation method according to claim 27, wherein a capsule endoscope having a wider-angle imaging optical system is used as the capsule endoscope.

30. The intra-subject observation method according to claim 27, wherein a capsule endoscope in which a center of gravity is decentered by changing a balance of weight in a front-back direction is used as the capsule endoscope.

31. The intra-subject observation method according to claim 30, wherein a capsule endoscope in which the front-end side is relatively heavier is used as the capsule endoscope.

32. The intra-subject observation method according to claim 30, wherein a capsule endoscope in which the front-end side is relatively lighter is used as the capsule endoscope.

33. The intra-subject observation method according to claim 27, wherein the first liquid and the second liquid are transparent to light of wavelengths of the imaging optical system of the capsule endoscope.

34. The intra-subject observation method according to claim 26, wherein the first liquid is drinking water and the second liquid is edible oil.

35. The intra-subject observation method according to claim 26, further comprising changing an amount of insertion into an organ of the first liquid and/or the second liquid.

36. The intra-subject observation method according to claim 35, wherein the changing the amount of insertion into an organ includes gradually increasing the amount of insertion of the first liquid.

37. The intra-subject observation method according to claim 26, further comprising changing an interfacial boundary position between the first liquid and the second liquid inserted into the organ by changing a posture of the subject.

38. The intra-subject observation method according to claim 26, further comprising detecting a floating position and/or floating posture at the interfacial boundary of the capsule medical apparatus when acquiring the intra-subject information.

39. The intra-subject observation method according to claim 38, further comprising combining a plurality of pieces of intra-subject information acquired by the capsule medical apparatus by referring to information of the detected floating position and/or floating posture of the capsule medical apparatus.

40. The intra-subject observation method according to claim 26, wherein a desired organ of the subject is a stomach.

* * * * *